US010428140B2

(12) United States Patent
Taguchi et al.

(10) Patent No.: US 10,428,140 B2
(45) Date of Patent: Oct. 1, 2019

(54) ANTI-EPHA4 ANTIBODY

(71) Applicant: EISAI R&D MANAGEMENT CO., LTD., Tokyo (JP)

(72) Inventors: Ryota Taguchi, Kobe (JP); Toshio Imai, Kobe (JP); Eiji Inoue, Kobe (JP); Akio Yamada, Kobe (JP); Aki Nakatani, Kobe (JP); Toshifumi Hirayama, Kobe (JP); Yuichi Ono, Kobe (JP); Shunsuke Ito, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 15/753,611

(22) PCT Filed: Sep. 6, 2016

(86) PCT No.: PCT/JP2016/076102
§ 371 (c)(1),
(2) Date: Feb. 20, 2018

(87) PCT Pub. No.: WO2017/043466
PCT Pub. Date: Mar. 16, 2017

(65) Prior Publication Data
US 2019/0077860 A1   Mar. 14, 2019

(30) Foreign Application Priority Data
Sep. 8, 2015  (JP) .................. 2015-177081

(51) Int. Cl.
  *A61K 39/00*   (2006.01)
  *A61P 21/02*   (2006.01)
  *A61P 25/28*   (2006.01)
  *C07K 16/28*   (2006.01)
  *C12N 15/62*   (2006.01)

(52) U.S. Cl.
  CPC .............. *C07K 16/28* (2013.01); *A61P 21/02* (2018.01); *A61P 25/28* (2018.01); *C07K 16/2866* (2013.01); *C12N 15/62* (2013.01); *A61K 2039/505* (2013.01); *C07K 2317/24* (2013.01); *C07K 2317/33* (2013.01); *C07K 2317/34* (2013.01); *C07K 2317/52* (2013.01); *C07K 2317/54* (2013.01); *C07K 2317/55* (2013.01); *C07K 2317/565* (2013.01); *C07K 2317/76* (2013.01); *C07K 2317/92* (2013.01)

(58) Field of Classification Search
  CPC ............... C07K 16/2866; C07K 16/24; C07K 2317/24; C07K 2317/56; C07K 16/28; A61K 39/00; A61P 21/02; A61P 21/28
  See application file for complete search history.

(56) References Cited

U.S. PATENT DOCUMENTS

| 2005/0013819 A1 | 1/2005 | Kinch et al. |
| 2008/0213250 A1 | 9/2008 | Hopf et al. |
| 2009/0142788 A1 | 6/2009 | Inoue |
| 2009/0191211 A1 | 7/2009 | Nakatsuru et al. |
| 2009/0275049 A1 | 11/2009 | Inoue et al. |
| 2013/0288278 A1 | 10/2013 | Inoue |
| 2014/0080146 A1 | 3/2014 | Obara et al. |

FOREIGN PATENT DOCUMENTS

| JP | 2007-522096 A | 8/2007 |
| JP | 2009-531273 A | 9/2009 |
| JP | 2010-285413 A | 12/2010 |
| WO | WO 2006/056467 | 6/2006 |
| WO | WO 2008/150010 | 8/2008 |
| WO | WO 2009/069808 | 6/2009 |
| WO | WO 2010/141974 | 12/2010 |
| WO | WO 2012/081502 | 6/2012 |
| WO | WO 2012/147798 | 11/2012 |
| WO | WO 2012/156351 | 11/2012 |
| WO | WO 2016/019280 | 2/2016 |

OTHER PUBLICATIONS

[No Author Listed], "KANAb014, Anti-EphA4 antagonistic antibody for amyotrophic lateral sclerosis," Kan Research Institute, Eisai Co., Ltd., Non-Confidential Deck, 5 pages.
[No Author Listed], "New AD Therapeutic Drug. Synapse Protection—Suppresses Reductions in Cognitive Function," Chemical Daily, Jun. 18, 2015, 3 pages (English Translation).
[No Author Listed], "Proteomics analysis of γ-secretase substrates for development of Alzheimer's Disease therapeutic drug," Article disclosed in Zikken Igaku, Experimental Medicine, (Separate Volume): Proteomics Analysis for Drug Development and Protein Investigation (YODOSHA): publication date Jul. 15, 2010, 14 pages (English Translation).
[No Author Listed], Eisai Scientific Day (New York)—Jun. 29, 2016, 141 pages.
[No Author Listed], Information Meeting 2015—Mar. 6, 2015, Eisai Co., Ltd., 36 pages.
[No Author Listed], Information Meeting 2016—Mar. 4, 2016, Eisai Co., Ltd., 55 pages.

(Continued)

*Primary Examiner* — Kimberly Ballard
*Assistant Examiner* — Stacey N MacFarlane
(74) *Attorney, Agent, or Firm* — Fish & Richardson P.C.

(57) ABSTRACT

It is intended to provide an anti-EphA4 antibody or an EphA4-binding fragment thereof which is capable of binding to EphA4 and inhibiting the binding between EphA4 and its ligand, and a pharmaceutical composition comprising the anti-EphA4 antibody or the EphA4-binding fragment thereof as an active ingredient. A mouse anti-EphA4 antibody having binding affinity for EphA4 was obtained, and the sequences of complementarity-determining regions (CDRs) of the mouse anti-EphA4 antibody were identified. This allowed for preparation of a humanized antibody comprising the CDR sequences of the mouse anti-EphA4 antibody in heavy chain variable region and light chain variable region.

80 Claims, 19 Drawing Sheets
Specification includes a Sequence Listing.

(56) References Cited

OTHER PUBLICATIONS

[No Author Listed], Information Meeting 2017—Mar. 10, 2017, Eisai Co., Ltd., 48 pages.
[No Author Listed], Press Conference 2015—Mar. 5, 2015, Eisai Co., Ltd., 36 pages.
[No Author Listed], Press Conference 2016—Mar. 3, 2016, Eisai Co., Ltd., 55 pages.
[No Author Listed], Press Conference 2017—Mar. 9, 2017, Eisai Co., Ltd., 48 pages.
[No Author Listed], Slides used in Wako Workshop held on Nov. 22, 2011, 26 pages.
[No Author Listed], Slides used in Advanced Medical Center Image Research Conference held on Nov. 27, 2012, 38 pages.
[No Author Listed], Slides used in Japan Neuroscience Society Conference held on Sep. 15, 2011, 11 pages.
[No Author Listed], Slides used in Japan Society for Dementia Research Conference held on Nov. 11, 2011, 38 pages (English Translation).
Goldshmit et al., "EphA4 Blockers Promote Axonal Regeneration and Functional Recovery Following Spinal Cord Injury in Mice," PloS One, 6(9):e24636, pp. 1-12 (Sep. 2011).
Inoue et al., "Synaptic activity prompts γ-secretase-mediated cleavage of EphA4 and dendritic spine formation," Journal of Cell Biology, 185(3):551-564 (May 2009).
Inoue, "EphA4/γ-secretase signal changes in Alzheimer's Disease," Medical Science Digest, Jun. 2016, 11 pages (English Translation).
Inoue, "Proteomic Analysis of γ-secretase Substrates," Kan Research Institute, slides used in Proteome Organization Conference held on Jul. 27, 2009, 19 pages.
Matsui et al., "Involvement of the γ-Secretase-Mediated EphA4 Signaling Pathway in Synaptic Pathogenesis of Alzheimer's Disease," Brain Pathology, 22(6):776-87 (Nov. 2012).
Swaminathan, "Research Highlights: Decoding Alzheimer's: γ-secretase targets EphA4," Nature Cell Biology, 11(6):684 (Jun. 2009).
Office Action in Columbia Application No. NC2018/0000652, 4 pages (English Translation).
Office Action in Pakistan Application No. 538/2016, dated Nov. 13, 2017, 2 pages (English Translation).
Spanevello et al., "Acute Delivery of EphA4-Fc Improves Functional Recovery after Contusive Spinal Cord Injury in Rats," Journal of Neurotrauma, 30:1023-1034, Jun. 2013.
Van Hoecke et al., "EPHA4 is a disease modifier of amyotrophic lateral sclerosis in animal models in humans," Nature Medicine, 18(9):1418-1422 (Sep. 2012).
Wiedemann, "Research Highlights: Signalling growth," Nature Reviews Neuroscience, 10:472 (Jul. 2009).
[No Author Listed], "Eisai Scientific Meeting 2019," Presentation, Eisai Co., Ltd., Presented on Apr. 23, 2019, 137 pages.
[No Author Listed], "FY2009 Product Creation Meeting," Presentation, Eisai Co., Ltd, Presented on Dec. 18, 2009, 121 pages.
European Extended Search Report in European Patent Application No. 16844327.3, dated Apr. 1, 2019, 8 pages.
Robberecht, "Progress report of the research group of Prof dr. Wim Robberecht," Queen Elisabeth Medical Foundation, Report 2014, Mar. 30, 2015, pp. 97-103.

[FIG. 1]
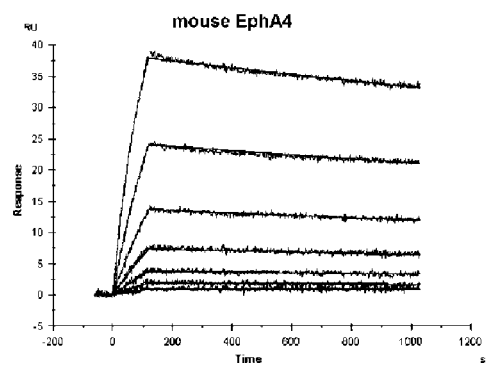
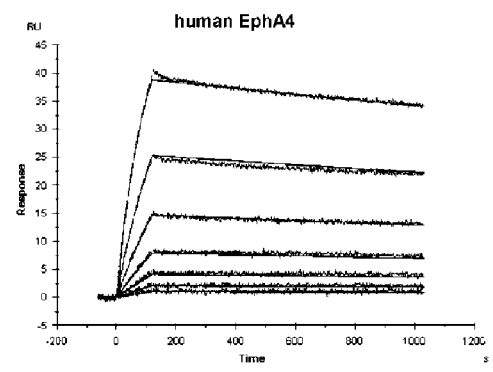

[FIG. 2]
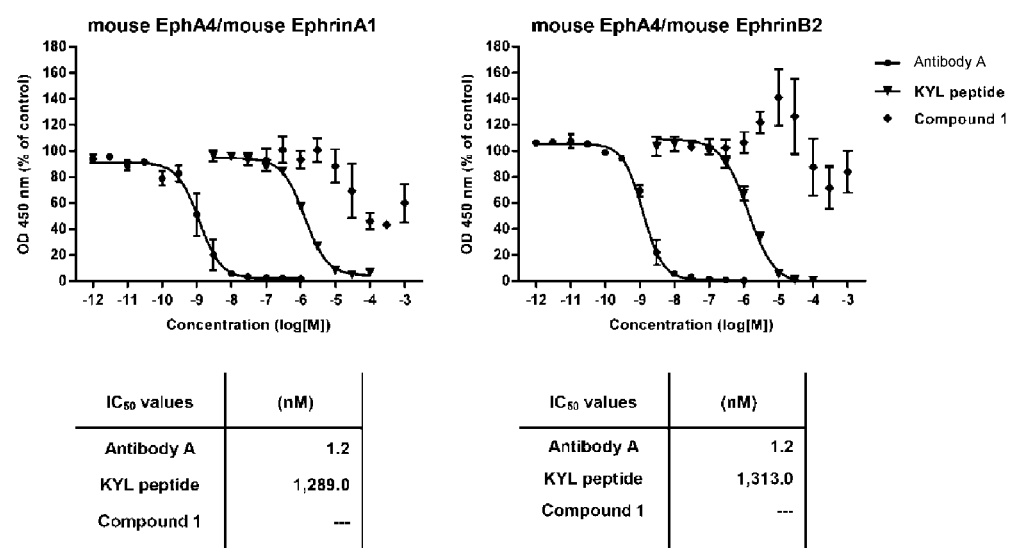

[FIG. 3]
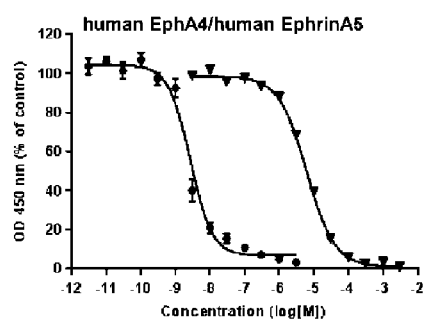
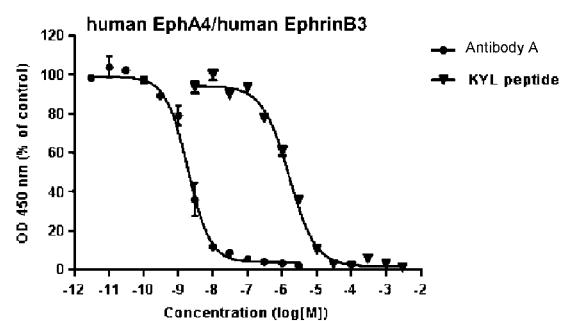

[FIG. 4A]
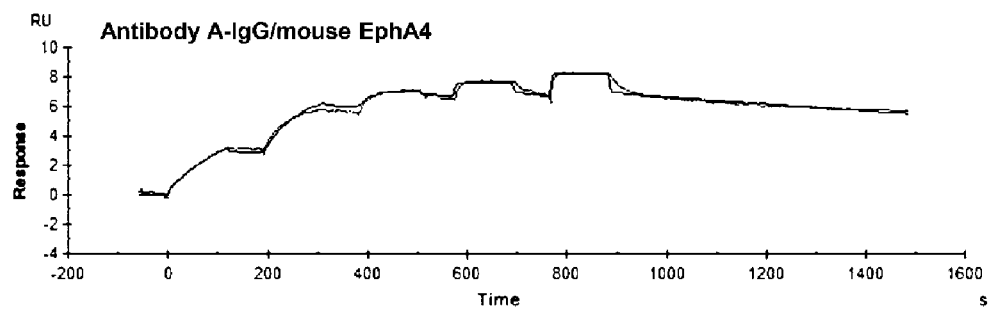
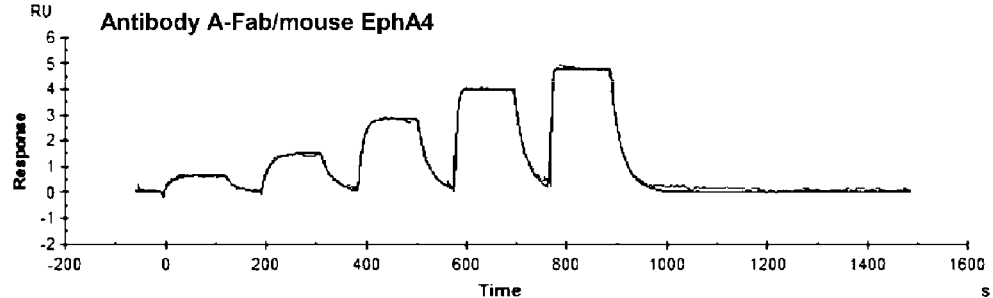
| Sample | ka (1/Ms) | Kd (1/s) | KD (M) | Rmax1 (RU) | Chi² (RU²) |
|---|---|---|---|---|---|
| antibody A-IgG | 2.88E+06 | 4.23E-04 | 1.47E-10 | 6.8 | 0.034 |
| antibody A-Fab | 9.31E+05 | 4.20E-02 | 4.51E-08 | 4.7 | 0.012 |

[FIG. 4B]
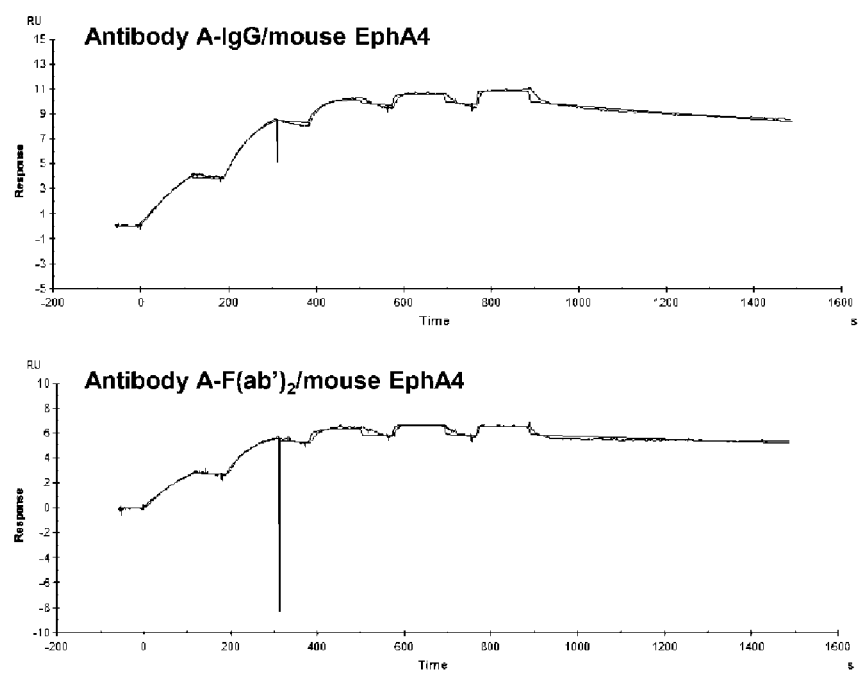

[FIG. 4C]
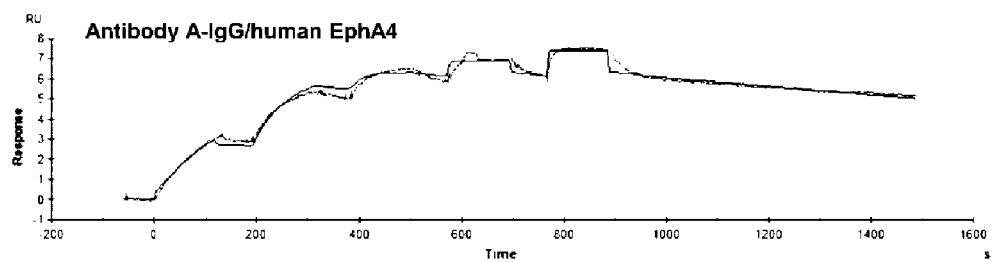
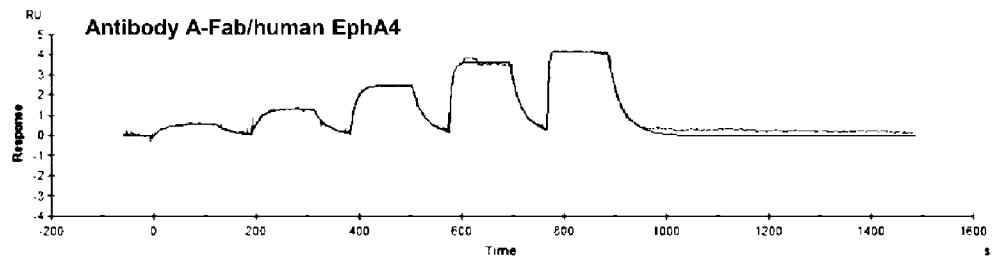
| Sample | ka (1/Ms) | Kd (1/s) | KD (M) | Rmax1 (RU) | Chi² (RU²) |
|---|---|---|---|---|---|
| antibody A-IgG | 2.70E+06 | 3.89E-04 | 1.44E-10 | 6.3 | 0.042 |
| antibody A-Fab | 9.21E+05 | 3.73E-02 | 4.04E-08 | 4.0 | 0.024 |

[FIG. 4D]
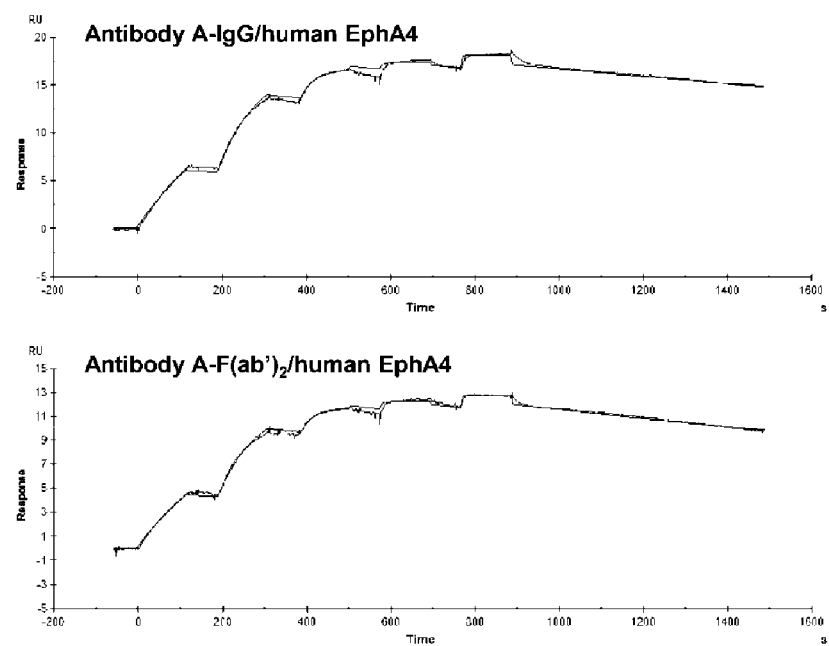

[FIG. 5]
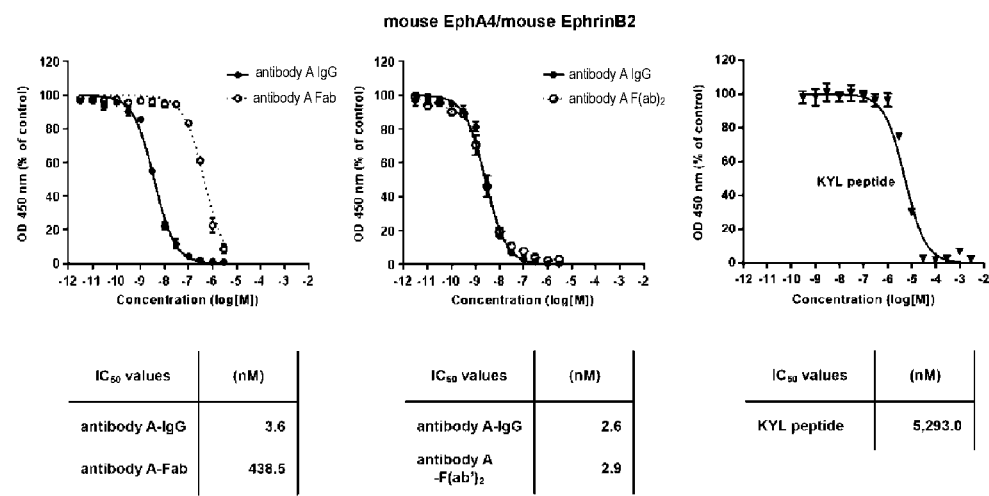

[FIG. 6]
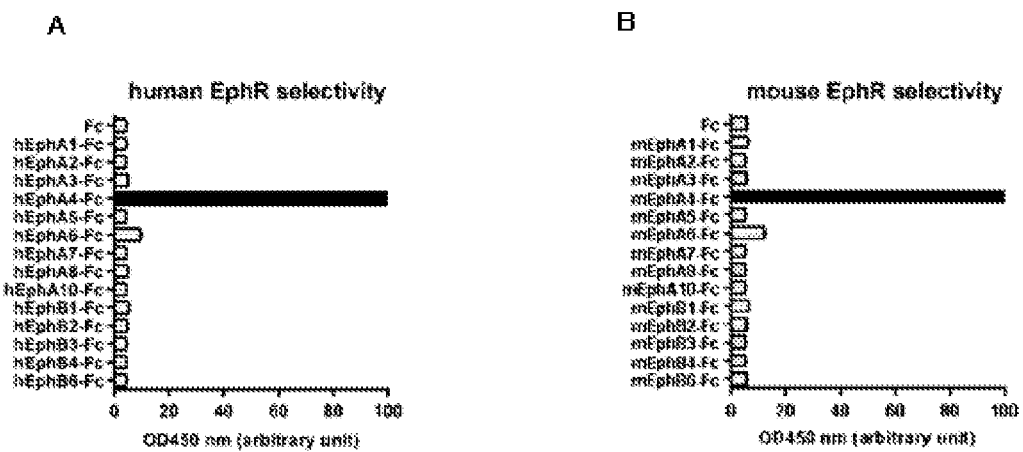

[FIG. 7]
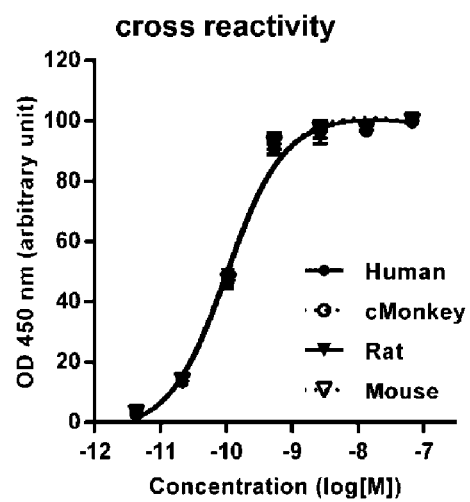

[FIG. 8]
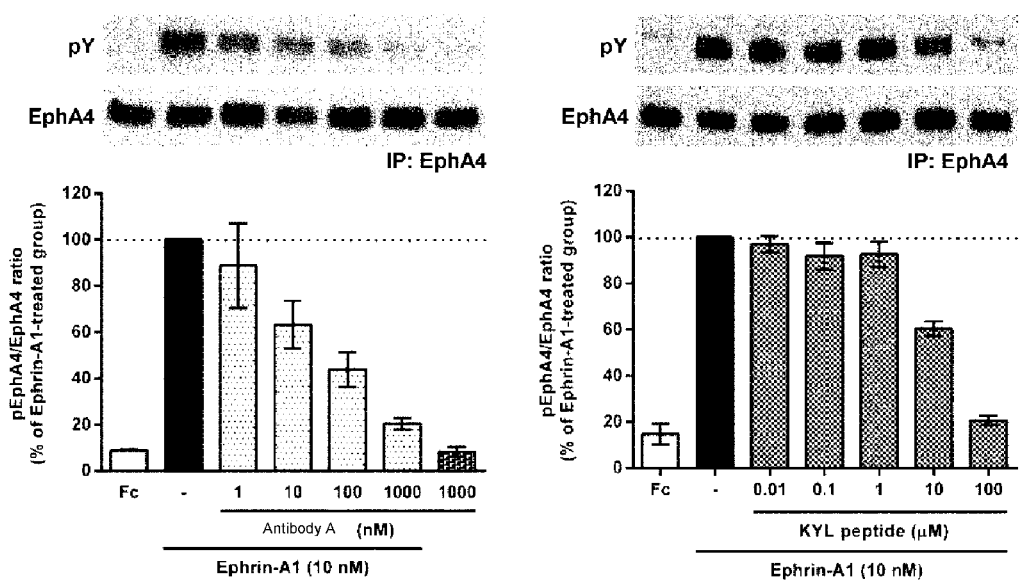

[FIG. 9]
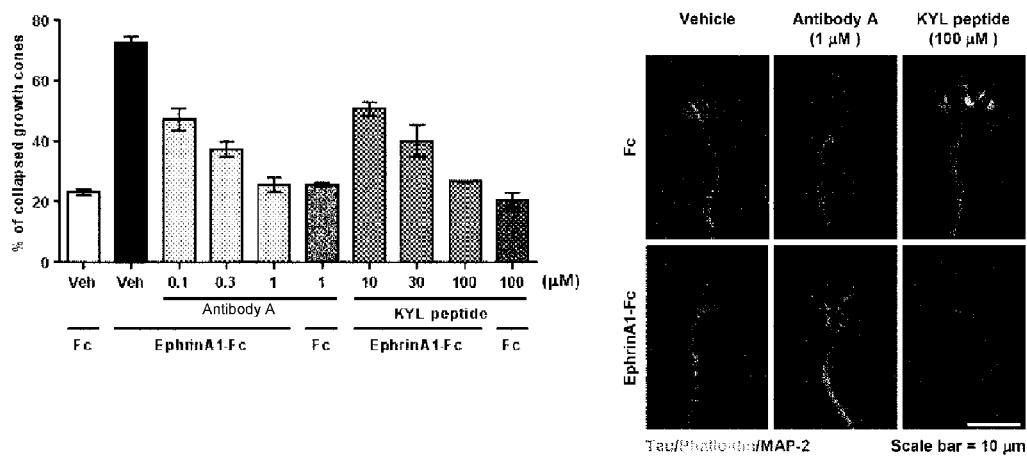

[FIG. 10]
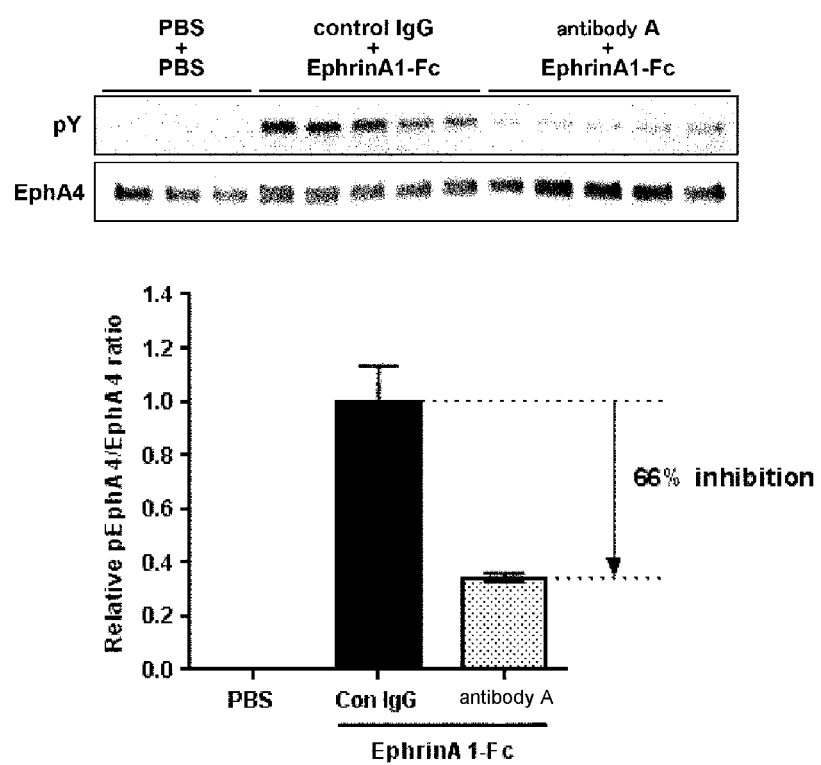

[FIG. 11]
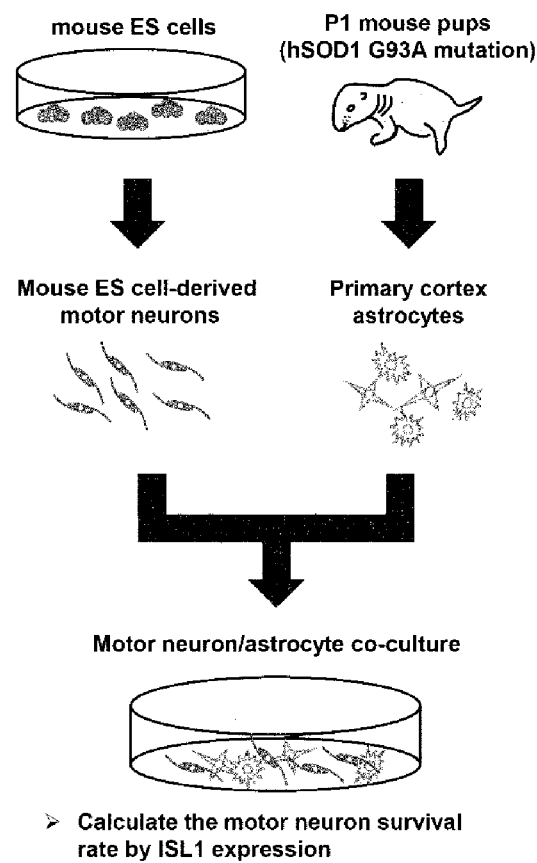

[FIG. 12]
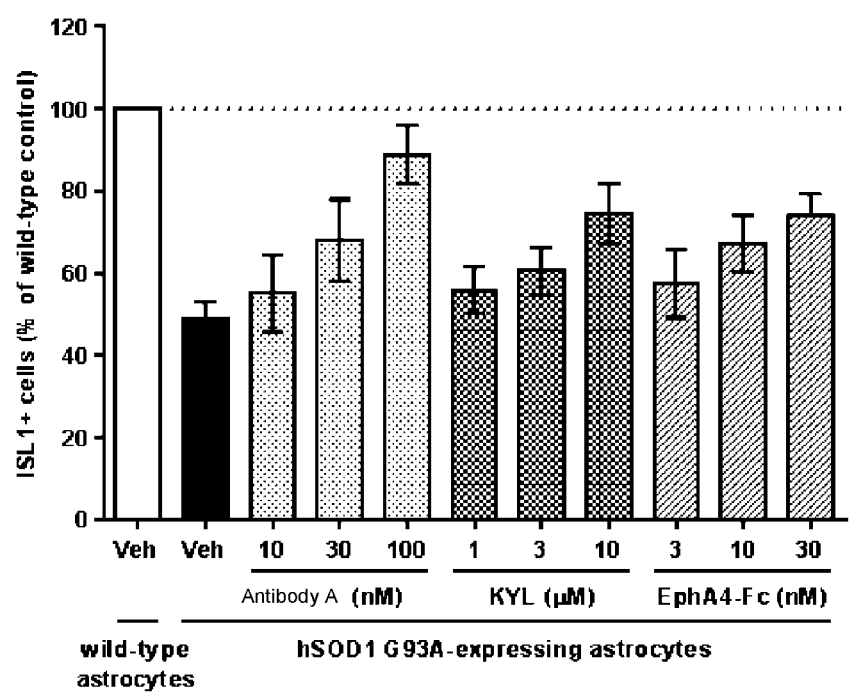

[FIG. 13]
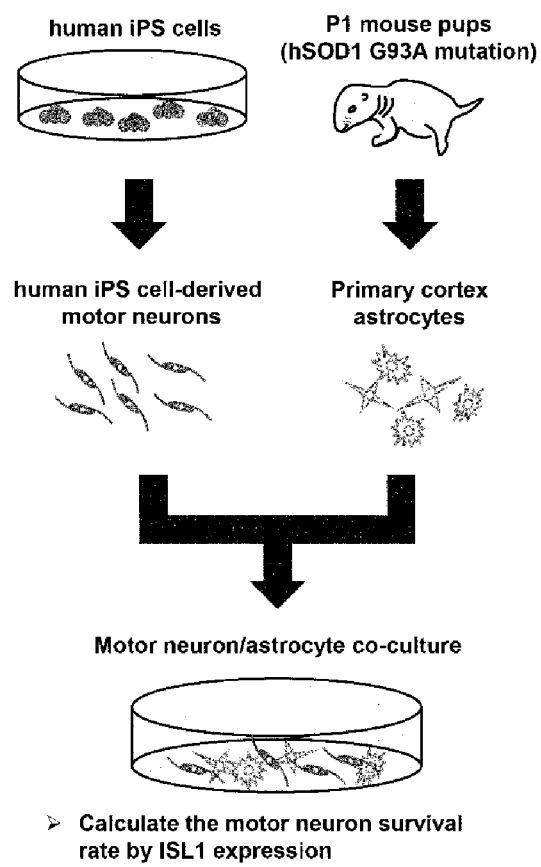

[FIG. 14]
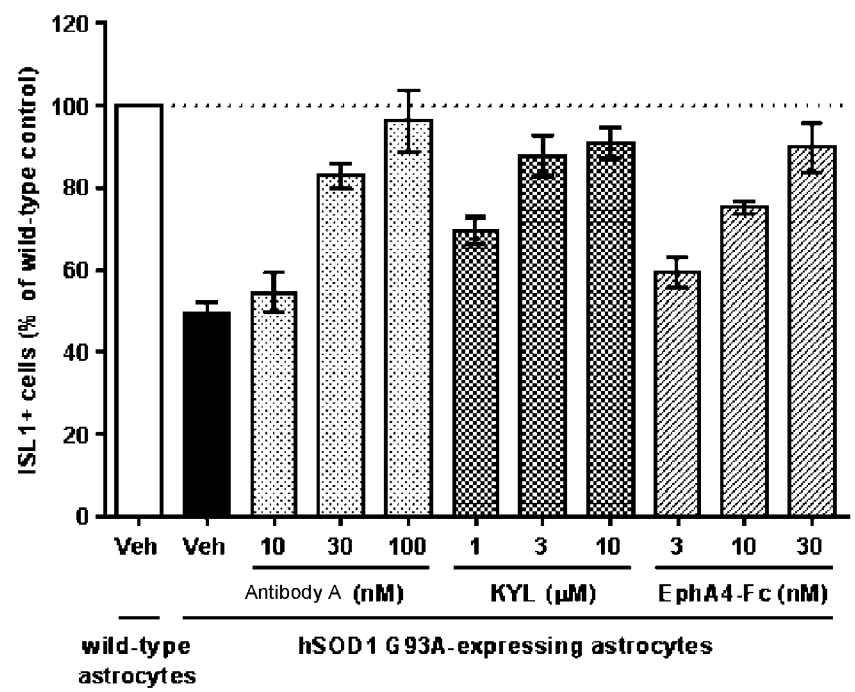

[FIG. 15]
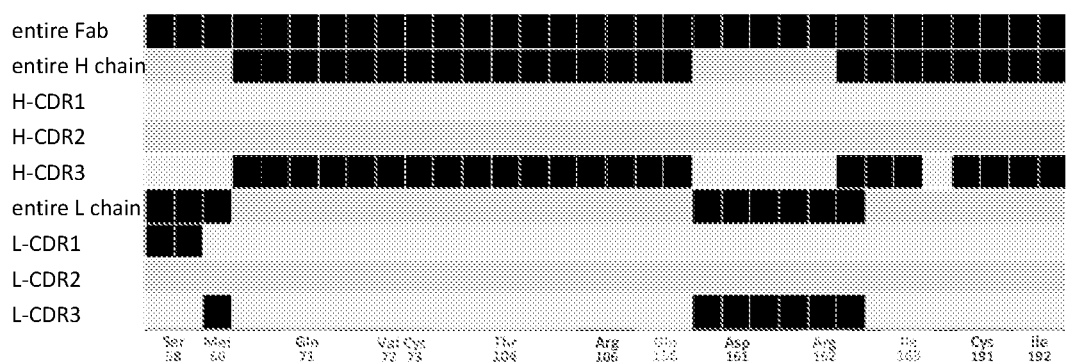

[FIG. 16]
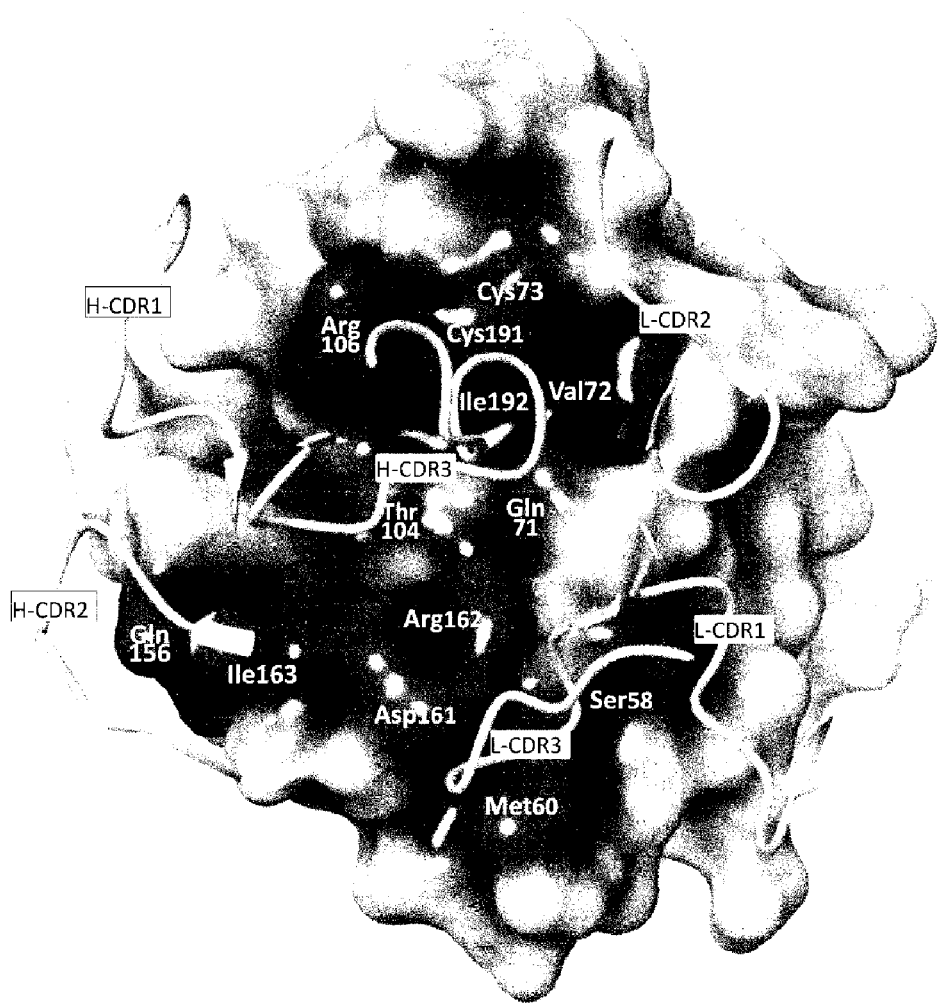

ANTI-EPHA4 ANTIBODY

FIELD OF THE INVENTION

The present invention relates to an antibody binding to EphA4.

BACKGROUND OF THE INVENTION

EphA4 is a member of the receptor tyrosine kinase family. Ephrin type A and type B are known as ligands of EphA4. Upon binding of EphA4 to its ligand ephrin, deadhesion signals are induced. EphA4 is expressed in motor neurons and regulates correct axonal guidance through ephrin expressed in non-projective regions of the motor neurons in the spinal cord during a neural network formation stage.

Previous studies suggest that the functional inhibition of EphA4 is an effective therapeutic procedure for neurodegenerative diseases such as amyotrophic lateral sclerosis (hereinafter, also referred to as "ALS") and Alzheimer's disease, and spinal cord injury.

The EphA4 gene has been reported to adjust the phenotype of ALS (Patent Literature 1; and Non-Patent Literature 1). Genetic defect of EphA4 or antagonism by EphA4-Fc or the like has been found to promote axonal elongation or functional recovery at the time of spinal cord injury in mice or rats (Non-Patent Literature 2; and Non-Patent Literature 3).

KYL peptide and compound 1 are known as existing EphA4 signaling inhibitors (Patent Literature 1; Non-Patent Literature 1; and Non-Patent Literature 2). However, there has been no report on an antibody having neutralizing activity.

PRIOR ART

Patent Literature 1: WO2012/156351 A1
Non-Patent Literature 1: Van Hoecke et al., Nature Medicine, vol. 18: 1418-1422, 2012
Non-Patent Literature 2: Goldschmit et al., PLoS one, vol. 6: e24636, 2011
Non-Patent Literature 3: Spanevello et al., Journal of Neurotrauma, vol. 30: 1023-1034, 2013

SUMMARY OF INVENTION

An object of the present invention is to provide an anti-EphA4 antibody or an EphA4-binding fragment thereof which is capable of binding to EphA4 and inhibiting the binding between EphA4 and its ligand, and a pharmaceutical composition comprising the anti-EphA4 antibody or the EphA4-binding fragment thereof as an active ingredient.

The present inventors have conducted diligent studies to attain the object and consequently completed the present invention by obtaining an anti-EphA4 antibody capable of binding to EphA4 and inhibiting the binding between EphA4 and its ligand.

Specifically, in one embodiment, the present invention relates to the following inventions.

(1) An anti-EphA4 antibody or an EphA4-binding fragment thereof, comprising
  (a) CDR-H1 comprising the amino acid sequence represented by SEQ ID NO: 26 or SEQ ID NO: 27;
  (b) CDR-H2 comprising the amino acid sequence represented by SEQ ID NO: 28 or SEQ ID NO: 29;
  (c) CDR-H3 comprising the amino acid sequence represented by SEQ ID NO: 30;
  (d) CDR-L1 comprising the amino acid sequence represented by SEQ ID NO: 31;
  (e) CDR-L2 comprising the amino acid sequence represented by SEQ ID NO: 32; and
  (f) CDR-L3 comprising the amino acid sequence represented by SEQ ID NO: 33.

(2) The anti-EphA4 antibody or the EphA4-binding fragment thereof according to (1), wherein
  the antibody or the EphA4-binding fragment thereof is humanized.

(3) The anti-EphA4 antibody or the EphA4-binding fragment thereof according to (1) or (2), wherein
  the antibody or the EphA4-binding fragment thereof specifically binds to EphA4 and inhibits the binding between EphA4 and ephrin.

(4) The anti-EphA4 antibody or the EphA4-binding fragment thereof according to any one of (1) to (3), wherein
  the antibody or the EphA4-binding fragment thereof comprises a heavy chain and a light chain, and
  the constant region of the heavy chain and the constant region of the light chain each comprise a human antibody-derived sequence.

(5) The anti-EphA4 antibody or the EphA4-binding fragment thereof according to (4), wherein
  the constant region of the heavy chain is derived from human IgG.

(6) The anti-EphA4 antibody or the EphA4-binding fragment thereof according to (5), wherein
  the human IgG is human $IgG_1$ or human $IgG_2$.

(7) The anti-EphA4 antibody or the EphA4-binding fragment thereof according to any one of (4) to (6), wherein
  the constant region of the light chain is derived from human Igκ.

(8) The anti-EphA4 antibody or the EphA4-binding fragment thereof according to any one of (1) to (7), wherein
  the EphA4-binding fragment is selected from the group consisting of Fab, Fab', $F(ab')_2$, and Fv.

(9) The anti-EphA4 antibody or the EphA4-binding fragment thereof according to (8), wherein
  the EphA4-binding fragment is $F(ab')_2$.

(10) A pharmaceutical composition comprising
  an anti-EphA4 antibody or an EphA4-binding fragment thereof according to any one of (1) to (9).

(11) The pharmaceutical composition according to (10) further comprising
  a pharmaceutically acceptable carrier.

(12) The pharmaceutical composition according to (10) or (11), wherein
  the pharmaceutical composition is used for the treatment of amyotrophic lateral sclerosis (ALS).

In another embodiment, the present invention also relates to the following inventions.

(1') An anti-EphA4 antibody or an EphA4-binding fragment thereof, comprising a heavy chain and a light chain, wherein
  a variable region of the heavy chain comprises the amino acid sequence represented by SEQ ID NO: 66, 68, 70, 72, 74 or 76, or an amino acid sequence derived from said sequence by substitution, addition, and/or deletion of one or more amino acids,
  a variable region of the light chain comprises the amino acid sequence represented by SEQ ID NO: 78, 80, 82 or 84, or an amino acid sequence derived from said sequence by the substitution, addition, and/or deletion of one or more amino acids, and the anti-EphA4 antibody or the EphA4-binding fragment thereof specifically binds to EphA4 and inhibits the binding between EphA4 and ephrin.

(2') An anti-EphA4 antibody or an EphA4-binding fragment thereof, comprising a heavy chain and a light chain, wherein
a variable region of the heavy chain comprises the amino acid sequence represented by SEQ ID NO: 66, 68, 70, 72, 74 or 76, and
a variable region of the light chain comprises the amino acid sequence represented by SEQ ID NO: 78, 80, 82 or 84.

(3') An anti-EphA4 antibody or an EphA4-binding fragment thereof according to (1') or (2'), wherein
a variable region of the heavy chain comprises the amino acid sequence represented by SEQ ID NO: 66, and
a variable region of the light chain comprises the amino acid sequence represented by SEQ ID NO: 78.

(4') An anti-EphA4 antibody or an EphA4-binding fragment thereof according to (1') or (2'), wherein
a variable region of the heavy chain comprises the amino acid sequence represented by SEQ ID NO: 68, and
a variable region of the light chain comprises the amino acid sequence represented by SEQ ID NO: 78.

(5') An anti-EphA4 antibody or an EphA4-binding fragment thereof according to (1') or (2'), wherein
a variable region of the heavy chain comprises the amino acid sequence represented by SEQ ID NO: 70, and
a variable region of the light chain comprises the amino acid sequence represented by SEQ ID NO: 78.

(6') An anti-EphA4 antibody or an EphA4-binding fragment thereof according to (1') or (2'), wherein
a variable region of the heavy chain comprises the amino acid sequence represented by SEQ ID NO: 72, and
a variable region of the light chain comprises the amino acid sequence represented by SEQ ID NO: 78.

(7') An anti-EphA4 antibody or an EphA4-binding fragment thereof according to (1') or (2'), wherein
a variable region of the heavy chain comprises the amino acid sequence represented by SEQ ID NO: 74, and
a variable region of the light chain comprises the amino acid sequence represented by SEQ ID NO: 78.

(8') An anti-EphA4 antibody or an EphA4-binding fragment thereof according to (1') or (2'), wherein
a variable region of the heavy chain comprises the amino acid sequence represented by SEQ ID NO: 76, and
a variable region of the light chain comprises the amino acid sequence represented by SEQ ID NO: 78.

(9') An anti-EphA4 antibody or an EphA4-binding fragment thereof according to (1') or (2'), wherein
a variable region of the heavy chain comprises the amino acid sequence represented by SEQ ID NO: 66, and
a variable region of the light chain comprises the amino acid sequence represented by SEQ ID NO: 80.

(10') An anti-EphA4 antibody or an EphA4-binding fragment thereof according to (1') or (2'), wherein
a variable region of the heavy chain comprises the amino acid sequence represented by SEQ ID NO: 68, and
a variable region of the light chain comprises the amino acid sequence represented by SEQ ID NO: 80.

(11') An anti-EphA4 antibody or an EphA4-binding fragment thereof according to (1') or (2'), wherein
a variable region of the heavy chain comprises the amino acid sequence represented by SEQ ID NO: 70, and
a variable region of the light chain comprises the amino acid sequence represented by SEQ ID NO: 80.

(12') An anti-EphA4 antibody or an EphA4-binding fragment thereof according to (1') or (2'), wherein
a variable region of the heavy chain comprises the amino acid sequence represented by SEQ ID NO: 72, and
a variable region of the light chain comprises the amino acid sequence represented by SEQ ID NO: 80.

(13') An anti-EphA4 antibody or an EphA4-binding fragment thereof according to (1') or (2'), wherein
a variable region of the heavy chain comprises the amino acid sequence represented by SEQ ID NO: 74, and
a variable region of the light chain comprises the amino acid sequence represented by SEQ ID NO: 80.

(14') An anti-EphA4 antibody or an EphA4-binding fragment thereof according to (1') or (2'), wherein
a variable region of the heavy chain comprises the amino acid sequence represented by SEQ ID NO: 76, and
a variable region of the light chain comprises the amino acid sequence represented by SEQ ID NO: 80.

(15') An anti-EphA4 antibody or an EphA4-binding fragment thereof according to (1') or (2'), wherein
a variable region of the heavy chain comprises the amino acid sequence represented by SEQ ID NO: 66, and
a variable region of the light chain comprises the amino acid sequence represented by SEQ ID NO: 82.

(16') An anti-EphA4 antibody or an EphA4-binding fragment thereof according to (1') or (2'), wherein
a variable region of the heavy chain comprises the amino acid sequence represented by SEQ ID NO: 68, and
a variable region of the light chain comprises the amino acid sequence represented by SEQ ID NO: 82.

(17') An anti-EphA4 antibody or an EphA4-binding fragment thereof according to (1') or (2'), wherein
a variable region of the heavy chain comprises the amino acid sequence represented by SEQ ID NO: 70, and
a variable region of the light chain comprises the amino acid sequence represented by SEQ ID NO: 82.

(18') An anti-EphA4 antibody or an EphA4-binding fragment thereof according to (1') or (2'), wherein
a variable region of the heavy chain comprises the amino acid sequence represented by SEQ ID NO: 72, and
a variable region of the light chain comprises the amino acid sequence represented by SEQ ID NO: 82.

(19') An anti-EphA4 antibody or an EphA4-binding fragment thereof according to (1') or (2'), wherein
a variable region of the heavy chain comprises the amino acid sequence represented by SEQ ID NO: 74, and
a variable region of the light chain comprises the amino acid sequence represented by SEQ ID NO: 82.

(20') An anti-EphA4 antibody or an EphA4-binding fragment thereof according to (1') or (2'), wherein
a variable region of the heavy chain comprises the amino acid sequence represented by SEQ ID NO: 76, and
a variable region of the light chain comprises the amino acid sequence represented by SEQ ID NO: 82.

(21') An anti-EphA4 antibody or an EphA4-binding fragment thereof according to (1') or (2'), wherein
a variable region of the heavy chain comprises the amino acid sequence represented by SEQ ID NO: 66, and
a variable region of the light chain comprises the amino acid sequence represented by SEQ ID NO: 84.

(22') An anti-EphA4 antibody or an EphA4-binding fragment thereof according to (1') or (2'), wherein
a variable region of the heavy chain comprises the amino acid sequence represented by SEQ ID NO: 68, and
a variable region of the light chain comprises the amino acid sequence represented by SEQ ID NO: 84.

(23') An anti-EphA4 antibody or an EphA4-binding fragment thereof according to (1') or (2'), wherein
a variable region of the heavy chain comprises the amino acid sequence represented by SEQ ID NO: 70, and
a variable region of the light chain comprises the amino acid sequence represented by SEQ ID NO: 84.

(24') An anti-EphA4 antibody or an EphA4-binding fragment thereof according to (1') or (2'), wherein
a variable region of the heavy chain comprises the amino acid sequence represented by SEQ ID NO: 72, and
a variable region of the light chain comprises the amino acid sequence represented by SEQ ID NO: 84.

(25') An anti-EphA4 antibody or an EphA4-binding fragment thereof according to (1') or (2'), wherein
a variable region of the heavy chain comprises the amino acid sequence represented by SEQ ID NO: 74, and
a variable region of the light chain comprises the amino acid sequence represented by SEQ ID NO: 84.

(26') An anti-EphA4 antibody or an EphA4-binding fragment thereof according to (1') or (2'), wherein
a variable region of the heavy chain comprises the amino acid sequence represented by SEQ ID NO: 76, and
a variable region of the light chain comprises the amino acid sequence represented by SEQ ID NO: 84.

(27') An anti-EphA4 antibody or an EphA4-binding fragment thereof according to any one of (1') to (26'), wherein
the antibody or the EphA4-binding fragment thereof specifically binds to EphA4 and inhibits the binding between EphA4 and ephrin.

(28') An anti-EphA4 antibody or an EphA4-binding fragment thereof according to any one of (1') to (27'), wherein
the constant region of the heavy chain and the constant region of the light chain each comprise a human antibody-derived sequence.

(29') The anti-EphA4 antibody or the EphA4-binding fragment thereof according to (28'), wherein
the constant region of the heavy chain is derived from human IgG.

(30') The anti-EphA4 antibody or the EphA4-binding fragment thereof according to (29'), wherein
the human IgG is human IgG consisting of human IgG$_2$ or a combination of human IgG$_1$ and human IgG$_2$.

(31') The anti-EphA4 antibody or the EphA4-binding fragment thereof according to (30'), wherein
the human IgG is human IgG$_2$.

(32') The anti-EphA4 antibody or the EphA4-binding fragment thereof according to (31'), wherein
the human IgG$_2$ has a C131S, C219S, V234A and/or G237A mutation under Eu numbering, and does not have a lysine residue at the carboxy terminal.

(33') The anti-EphA4 antibody or the EphA4-binding fragment thereof according to (32'), wherein
the human IgG$_2$ comprises the amino acid sequence represented by SEQ ID NO: 62.

(34') The anti-EphA4 antibody or the EphA4-binding fragment thereof according to (30'), wherein
the human IgG is human IgG consisting of a combination of human IgG$_1$ and human IgG$_2$.

(35') The anti-EphA4 antibody or the EphA4-binding fragment thereof according to (34'), wherein
in the human IgG consisting of a combination of human IgG$_1$ and human IgG$_2$, a CH1 region and a hinge region are human IgG$_1$, and a CH2 region and a CH3 region are human IgG$_2$.

(36') The anti-EphA4 antibody or the EphA4-binding fragment thereof according to (35'), wherein
the human IgG consisting of a combination of human IgG$_1$ and human IgG$_2$ has a V234A and/or a G237A mutation under Eu numbering, and does not have a lysine residue at the carboxy terminal.

(37') The anti-EphA4 antibody or the EphA4-binding fragment thereof according to (36'), wherein
the human IgG consisting of a combination of human IgG$_1$ and human IgG$_2$ comprises the amino acid sequence represented by SEQ ID NO: 60.

(38') The anti-EphA4 antibody or the EphA4-binding fragment thereof according to any one of (28') to (37'), wherein
the constant region of the light chain is derived from human Igκ.

(39') The anti-EphA4 antibody or the EphA4-binding fragment thereof according to any one of (1') to (38'), wherein
the EphA4-binding fragment is selected from the group consisting of Fab, Fab', F(ab')$_2$, and Fv.

(40') The anti-EphA4 antibody or the EphA4-binding fragment thereof according to (39'), wherein
the EphA4-binding fragment is F(ab')$_2$.

(41') A pharmaceutical composition comprising
an anti-EphA4 antibody or an EphA4-binding fragment thereof according to any one of (1') to (40').

(42') The pharmaceutical composition according to (41') further comprising
a pharmaceutically acceptable carrier.

(43') The pharmaceutical composition according to (41') or (42'), wherein
the pharmaceutical composition is used for the treatment of amyotrophic lateral sclerosis (ALS).

One of or any combination of two or more of the aspects of the present invention mentioned above is also included in the scope of the present invention.

The present invention provides an anti-EphA4 antibody or an EphA4-binding fragment thereof which is capable of binding to EphA4 and inhibiting the binding between EphA4 and its ligand, and a pharmaceutical composition comprising the anti-EphA4 antibody or the EphA4-binding fragment thereof as an active ingredient.

BRIEF DESCRIPTION OF THE DRAWINGS

FIG. 1 shows the binding affinity of an anti-EphA4 monoclonal antibody (antibody A) for human EphA4 and mouse EphA4.

FIG. 2 shows inhibition of the binding of mouse EphA4 to mouse Ephrin A1 and mouse Ephrin B2 by the anti-EphA4 monoclonal antibody (antibody A), KYL peptide, and compound 1.

FIG. 3 shows inhibition of the binding of human EphA4 to human Ephrin A5 and human Ephrin B3 by the anti-EphA4 monoclonal antibody (antibody A), and KYL peptide.

FIG. 4A shows the binding affinity of antibody A-IgG (antibody A) and antibody A-Fab for mouse EphA4.

FIG. 4B shows the binding affinity of antibody A-IgG (antibody A) and antibody A-F(ab')$_2$ for mouse EphA4.

FIG. 4C shows the binding affinity of antibody A-IgG (antibody A) and antibody A-Fab for human EphA4.

FIG. 4D shows the binding affinity of antibody A-IgG (antibody A) and antibody A-F(ab')$_2$ for human EphA4.

FIG. 5 shows the inhibition of the binding between mouse EphA4 and mouse Ephrin B2 by antibody A-IgG (antibody A), antibody A-F(ab')$_2$, antibody A-Fab, and KYL peptide.

FIG. 6 shows the binding specificity of antibody A for human Eph receptor (FIG. 6A) and mouse Eph receptor (FIG. 6B).

FIG. 7 shows the binding activity of antibody A against mouse, rat, monkey, and human EphA4.

FIG. 8 shows that antibody A suppresses, in a concentration-dependent manner, EphA4 autophosphorylation induced by Ephrin A1 in hippocampal neurons. The pY in FIG. 8 exhibit phosphorylated EphA4.

FIG. 9 shows that antibody A suppresses, in a concentration-dependent manner, growth cone collapse induced by Ephrin A1 in hippocampal neurons.

FIG. 10 shows that antibody A suppresses EphA4 autophosphorylation induced by Ephrin A1 in the mouse newborn brain. The pY in FIG. 10 exhibit phosphorylated EphA4.

FIG. 11 shows a schematic view of an evaluation system carried out in Example 13.

FIG. 12 shows that antibody A protects motor neurons in in vitro ALS models using mouse ES cells.

FIG. 13 shows a schematic view of an evaluation system carried out in Example 14.

FIG. 14 shows that antibody A protects motor neurons in in vitro ALS models using human iPS cells.

FIG. 15 shows the amino acids of EphA4 Ligand-Binding Domain (EphA4-LBD) on the abscissa and the structural region of Fab on the ordinate. The black bits depict the points of intersection of combinations having an interaction. A plurality of bits presenting for one amino acid correspond to the types of the interaction (hydrogen bond, surface contact, etc.). An amino acid having a larger number of bits means that the amino acid binds to Fab with diverse interactions.

FIG. 16 shows the surface structure of EphA4 Ligand-Binding Domain (EphA4-LBD). In FIG. 16, the dark color regions correspond to Fab-binding regions. In this figure, the names and the residue numbers of amino acids contained in the binding regions are shown at the corresponding positions, and the H chain and L chain CDRs of Fab to be bound are indicated by ribbon models.

DETAILED DESCRIPTION OF THE INVENTION

The present invention relates to an anti-EphA4 antibody which binds to EphA4.

The anti-EphA4 antibody used in the present invention is an antibody that can recognize and bind to EphA4. As mentioned below, the antibody may be an intact antibody or may be an antigen-binding fragment thereof or a synthetic antibody (e.g., a recombinant antibody, a chimeric antibody, and a humanized antibody) as long as it has binding affinity for EphA4. In the present invention, it can be understood that EphA4 refers to human-, mouse-, rat-, or monkey-derived EphA4. The human-, mouse-, rat-, or monkey-derived EphA4 can be obtained from a public database in which sequence information is registered, such as GenBank provided by National Center for Biotechnology Information (USA). Alternatively, primers are designed on the basis of nucleotide sequence information on EphA4 of an animal species closely related thereto, and sequence information on the EphA4 gene can be obtained by cloning from RNA extracted from the desired animal species. For example, nucleotide sequence information on human, mouse, rat, or monkey EphA4 is registered under GenBank Accession Nos. NM_004438.4, NM_007936.3, NM_001162411.1, and NM_001260870, respectively, on the database.

In one aspect of the present invention, EphA4 comprises the amino acid sequence represented by SEQ ID NO: 1 or an amino acid sequence derived from the amino acid sequence by the substitution, addition, and/or deletion of one or more amino acids, or the amino acid sequence represented by SEQ ID NO: 3 or an amino acid sequence derived from the amino acid sequence by the substitution, addition, and/or deletion of one or more amino acids. In the present invention, the term "or more" used as to EphA4 is not limited as long as the resulting sequence maintains functional characteristics equivalent to the original sequence. The term "or more" is 2 to 100, for example, 2 to 90, 2 to 80, 2 to 70, 2 to 60, 2 to 50, 2 to 40, 2 to 30, 2 to 20, 2 to 10, or 2 to 5 or is within 10%, for example, within 9%, within 8%, within 7%, within 6%, or within 5% of the number of amino acids in the amino acid sequence.

In one aspect of the present invention, the anti-EphA4 antibody or the EphA4-binding fragment thereof is an antibody specifically binding to EphA4. The term "specific binding" is a term well known to those skilled in the art, and a method for determining the specific binding of an antibody or an antigen-binding fragment thereof to an antigen or an epitope is also well known. In one embodiment of the present invention, it is understood that the "specific binding" means that the anti-EphA4 antibody or the EphA4-binding fragment thereof is capable of binding to EphA4 through immunological reaction more rapidly and/or for a duration of a longer time with larger binding affinity and larger binding activity as compared with its binding to other target molecules. In this context, the specific binding to other targets of an antibody or an antigen-binding fragment thereof specifically binding to one target is not excluded. In another embodiment of the present invention, the "specific binding" can be indicated by an antibody having KD of at least approximately $10^{-7}$ M, at least approximately $10^{-8}$ M, at least approximately $10^{-9}$ M, at least approximately $10^{-10}$ M, at least approximately $10^{-11}$ M, or at least approximately $10^{-12}$ M or greater for EphA4. In a further alternative embodiment of the present invention, it is understood that the "specific binding" is binding to EphA4 through immunological reaction, but not substantially binding to other subclasses and subtypes of Eph receptors.

In one aspect of the present invention, the anti-EphA4 antibody or the EphA4-binding fragment thereof of the present invention is an antibody binding to the extracellular region of EphA4. The anti-EphA4 antibody or the EphA4-binding fragment thereof of the present invention can be, for example, an antibody or an antigen-binding fragment that comprises the amino acid sequence represented by SEQ ID NO: 2 or an amino acid sequence derived from the amino acid sequence by the substitution, addition, and/or deletion of one or more amino acids, or comprises the amino acid sequence represented by SEQ ID NO: 4 or an amino acid sequence derived from the amino acid sequence by the substitution, addition, and/or deletion of one or more amino acids, and binds to any site in the EphA4 extracellular region. In the present invention, the term "or more" used as to the extracellular region of EphA4 is, but is not limited to, 2 to 50, for example, 2 to 45, 2 to 40, 2 to 35, 2 to 30, 2 to 25, 2 to 20, 2 to 15, 2 to 10, or 2 to 5, or within 10%, for example, within 9%, within 8%, within 7%, within 6%, or within 5% of the number of amino acids in the amino acid sequence.

In one aspect of the present invention, the anti-EphA4 antibody or the EphA4-binding fragment thereof can specifically bind to EphA4 and inhibit the binding between EphA4 and ephrin.

In one embodiment of the present invention, the anti-EphA4 antibody or the EphA4-binding fragment thereof can specifically bind to at least one of human EphA4, mouse EphA4, rat EphA4, and monkey EphA4 and inhibit the binding thereof to their ligands. In a preferred embodiment of the present invention, the anti-EphA4 antibody or the EphA4-binding fragment thereof can specifically bind to two or more of human EphA4, mouse EphA4, rat EphA4, and monkey EphA4 and inhibit the binding thereof to their ligands. In another preferred embodiment of the present invention, the anti-EphA4 antibody or the EphA4-binding fragment thereof can specifically bind to all of human EphA4, mouse EphA4, rat EphA4, and monkey EphA4 and inhibit the binding thereof to their ligands.

A method generally known to those skilled in the art can be used as a method for measuring the antigen-binding properties (e.g., binding affinity and interspecies cross-reactivity) of the antibody or the antigen-binding fragment thereof. For example, the binding affinity can be measured by use of Biacore(R) biosensor, KinExA biosensor, scintillation proximity assay, ELISA, ORIGEN immunoassay (IGEN International), flow cytometry, fluorescence quenching, fluorescence transfer, yeast display, and/or immunostaining, though the method is not limited thereto. The neutralizing activity of the antibody or the antigen-binding fragment thereof against the binding between EphA4 and its ligand can be measured by use of Biacore(R) biosensor, ELISA, and/or flow cytometry, though the method is not limited thereto.

The anti-EphA4 antibody or the EphA4-binding fragment thereof of the present invention can be any of a monoclonal antibody, a polyclonal antibody, and an EphA4-binding fragment thereof as long as it binds to EphA4, preferably, specifically binds to EphA4.

In the present invention, the anti-EphA4 antibody or the EphA4-binding fragment thereof of the present invention can be of any class such as IgG, IgA or IgM (or subclass thereof) and is not limited by a particular class. Immunoglobulins are classified into different classes depending on the antibody amino acid sequences of their heavy chain (also called H chain) constant regions. There are five main immunoglobulin classes: IgA, IgD, IgE, IgG, and IgM, some of which can be further divided into subclasses (isotypes) of, for example, $IgG_1$, $IgG_2$, $IgG_3$, $IgG_4$, $IgA_1$, and $IgA_2$. The heavy chain constant regions corresponding to different classes of immunoglobulins are respectively called α, δ, ε, γ, and μ. The light chain (also called L chain) types of antibodies are λ, and κ chains.

The anti-EphA4 antibody or the EphA4-binding fragment thereof of the present invention may be an IgG antibody and may be, for example, an $IgG_1$ antibody or an $IgG_2$ antibody. Also, the anti-EphA4 antibody or the EphA4-binding fragment thereof of the present invention may be a monomer, a dimer, or a multimer in some cases.

In one aspect of the present invention, the anti-EphA4 antibody or the EphA4-binding fragment thereof of the present invention may be a combination of IgG antibodies derived from different subclasses, such as IgG antibody consisting of a combination of $IgG_1$ antibody and $IgG_2$ antibody.

In the present specification, the antigen-binding fragment of the antibody is not particularly limited as long as the antigen-binding fragment is a functional and structural fragment of the antibody and maintains binding activity against the antigen to which the antibody can bind. Examples of the antigen-binding fragment of the antibody include, but are not limited to, Fab, Fab', $F(ab')_2$, Fv, and single-chain Fv (scFv), their variants, fusion proteins comprising an antibody moiety, and other modified structures of immunoglobulin molecules comprising an antigen recognition site. In one aspect, the binding fragment of the antibody of the present invention is $F(ab')_2$.

The antigen-binding fragment of the antibody can be obtained, for example, via the protein digestion of the whole antibody with a protease such as papain or pepsin, or may be produced directly by recombinant host cells (e.g., eukaryotes such as yeast cells, plant cells, insect cells, or mammalian cells, or prokaryotes such as E. coli). For example, Fab'-SH fragments can be recovered directly from E. coli and chemically bonded to form a $F(ab')_2$ fragment. Alternatively, $F(ab')_2$ may be formed using leucine zipper GCN4, which promotes the assembly of $F(ab')_2$ molecules. In the case of producing scFv by a chemical synthesis technique, an automatic synthesizer can be used. In the case of producing scFv by a gene recombination technique, an appropriate plasmid containing a polynucleotide encoding scFv can be transferred to appropriate host cells (e.g., eukaryotes such as yeast cells, plant cells, insect cells, or mammalian cells, or prokaryotes such as E. coli). The polynucleotide encoding scFv of interest may be prepared by a well known operation such as polynucleotide ligation. The resulting scFv may be isolated by use of a standard protein purification technique known in the art.

In the present invention, the variable region of the antibody may mean a variable region of an antibody light chain and/or a variable region of an antibody heavy chain, and the constant region of the antibody may mean a constant region of an antibody light chain and/or a constant region of an antibody heavy chain. The heavy chain variable region and the light chain variable region are each composed of four framework regions (FRs) connected via three CDRs also known as hypervariable regions. The CDRs in each chain are held in close proximity by FRs and contribute, together with CDRs in the other chain, to the formation of the antigen-binding site of the antibody. Examples of techniques for determining CDRs include, but are not limited to: (1) an approach based on cross-species sequence variability (e.g., Kabat et al., Sequences of Proteins of Immunological Interest, 5th ed., 1991, National Institutes of Health, Bethesda Md.); and (2) an approach based on the crystallographic study of an antigen-antibody complex (Al-lazikani et al., 1997 J. Molec. Biol. 273: 927-948). These approaches or other approaches may be used in combination. The constant region of the heavy chain is composed of tree domains, i.e., CH1, CH2 and CH3, and a hinge region, and they are positioned from the amino terminus (N-terminus) to carboxy terminus (C-terminus) in order of CH1, a hinge region, CH2 and CH3. The constant region of the light chain is composed of one domain CL.

In the present invention, the monoclonal antibody may mean an antibody that is obtained from a population of substantially homogeneous antibodies. Specifically, individual antibodies contained in the population are identical except for natural mutants that might be present to some extent. The monoclonal antibody is directed to a single antigen site and is very specific. Moreover, in contrast to a typical polyclonal antibody targeting different antigens or different epitopes, each monoclonal antibody targets a single epitope in an antigen. The modifier "monoclonal" denotes the characteristics of the antibody that is obtained from a population of substantially homogeneous antibodies, and should not be restrictively interpreted as requiring the production of the antibody by a particular method.

The anti-EphA4 antibody or the EphA4-binding fragment thereof of the present invention may be a chimeric antibody, a humanized antibody, a human antibody, a nonhuman mammal (e.g., monkey, mouse, rat, rabbit, bovine, horse, or goat) antibody, or an EphA4-binding fragment thereof. The chimeric antibody is, for example, an antibody comprising the variable regions of a nonhuman (e.g., mouse or rat) antibody joined to the constant regions of a human antibody, and may refer to, for example, an antibody having nonhuman antibody-derived variable regions and human antibody-derived constant regions. The humanized antibody is, for example, an antibody comprising the hypervariable regions (also referred to as complementarity-determining regions (CDRs)) of a nonhuman antibody introduced in a human antibody, and may refer to, for example, an antibody having nonhuman antibody-derived CDRs and the other antibody regions derived from a human antibody. However, in the present invention, the distinction between the chimeric antibody and the humanized antibody is not necessarily required to be clear, and the antibody may be in a form that may be regarded as both of the chimeric antibody and the humanized antibody. A preferred aspect of the humanized antibody according to the present invention is an antibody having rodent antibody-derived CDRs and the other antibody regions derived from a human antibody, particularly preferably an antibody having mouse antibody-derived CDRs and the other antibody regions derived from a human antibody. The humanization can be performed by use of a CDR grafting method (Kontermann and Dubel, Antibody Engineering, Springer Lab Manual (2001); and Tsurushita et al., Methods 36: 69-83 (2005)) and can also be performed by a method known in the art (see e.g., Jones et al., Nature 321: 522-525 (1986); Riechmann et al., Nature 332: 323-327 (1988); and Verhoeyen et al., Science 239: 1534-1536 (1988)) which involves replacing CDR sequences for the corresponding sequences of a human antibody. The humanized antibody is typically a human antibody, some CDR residues and, optionally, some FR residues of which are replaced with residues derived from the analogous sites of a nonhuman antibody.

For reducing antigenicity, it can be important to select the use of human variable regions in both of the light chain and the heavy chain in the preparation of the humanized antibody. According to a "best-fit" method, the whole library of known human FR sequences is screened for the sequences of variable regions of a rodent antibody. Next, human sequences most similar to the rodent sequences are accepted as human FRs of the humanized antibody. See, for example, Sims et al., J. Immunol. 151: 2296-2308 (1993) and Chothia et al., J. Mol. Biol. 196: 901-917 (1987). In another method, particular frameworks derived from common sequences of all human antibodies as to particular light chain or heavy chain subgroups are used. The same frameworks can be used for some different humanized antibodies. See, for example, Carter et al., Proc. Natl. Acad. Set USA 89: 4285-4289 (1992) and Presta et al., J. Immunol. 151: 2623-2632 (1993).

Moreover, it is generally desirable that the humanized antibody should maintain high binding affinity for the antigen and other preferred biological properties. In order to attain this goal, according to one method, the humanized antibody is prepared by the step of analyzing parent sequences and various conceptual humanized products using three-dimensional models of the parent sequences and humanized sequences. In general, a three-dimensional immunoglobulin model can be utilized and is known to those skilled in the art. A computer program that illustrates and indicates potential three-dimensional conformations of selected candidate immunoglobulin sequences can be utilized These indications can be studied to analyze the possible roles of residues in the functions of the candidate immunoglobulin sequences, i.e., to analyze residues that influence the ability of the candidate immunoglobulins to bind to the antigen. By this method, FR residues can be selected from a recipient sequence and an import sequence and combined so as to achieve desirable antibody characteristics such as enhanced binding affinity for one or more target antigens (e.g., EphA4 or a fragment thereof).

Needless to say, the antibody of the present invention also includes an antibody derived from the chimeric antibody or the humanized antibody exemplified above by appropriate engineering (e.g., the modification of the antibody or the partial substitution, addition, and/or deletion of the amino acid sequence of the antibody) such that the antibody maintains its functions (or a function is imparted to the antibody or a function of the antibody is improved). More specifically, an antibody lacking lysine (Lys) positioned at the carboxy terminus (C-terminus) of the heavy chain by an artificial method such as genetic engineering in order to reduce the heterogeneity of antibodies produced by antibody-producing cells is also included in the scope of the present invention. Also, an antibody having a modified amino acid sequences in the constant region for modifying an effector function of antibody, such as an antibody in which valine (Val) at the position 234 of human $IgG_2$ antibody under Eu numbering has been substituted with alanine (Ala), and glycine (Gly) at the position 237 has been substituted with alanine (Ala) so as to reduce the activity of antibody-dependent cell-mediated cytotoxicity (ADCC) and/or of antibody-dependent cell-mediated phagocytosis (ADCP) is also included in the scope of the present invention. Furthermore, a bispecific antibody (Kontermann (2012), mAbs 4, 182-97) which has, along with an antibody-binding region having CDR sequences of the antibody of the present invention, an antigen-binding region which binds to another antigen, is also included in the scope of the present invention.

The anti-EphA4 antibody or the EphA4-binding fragment thereof of the present invention may be modified, if desired. The modification of the anti-EphA4 antibody or the EphA4-binding fragment thereof of the present invention may be a modification that changes (a) the three-dimensional structure of an amino acid sequence in a modification region, such as sheet or helix conformation; (b) the electric charge or hydrophobic status of the molecule at a target site; or (c) the effects of a modification on the maintenance of side chain volume, or may be a modification by which these changes are not clearly observed.

The modification of the anti-EphA4 antibody or the EphA4-binding fragment thereof of the present invention may be achieved by, for example, the substitution, deletion, and/or addition of a constituent amino acid residue(s).

In the present specification, the amino acid is used in the broadest sense thereof and includes not only natural amino acids, for example, serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro) but non-natural amino acids such as amino acid variants and derivatives. Those skilled in the art naturally understand, by taking this wide definition into consideration, that examples of the amino acid in the present specification include: L-amino acids; D-amino acids; chemically modified amino acids such as amino acid variants and amino acid derivatives; amino acids, such as norleucine, β-alanine, and ornithine, which do not serve as materials constituting proteins in vivo; and chemically synthesized compounds having the characteristics of amino acids generally known to those skilled in the art. Examples of the non-natural amino acids include α-methylamino acids (α-methylalanine, etc.), D-amino acids (D-aspartic acid, D-glutamic acid, etc.), histidine-like amino acids (2-amino-histidine, β-hydroxy-histidine, homohistidine, α-fluoromethyl-histidine, α-methyl-histidine, etc.), amino acids having extra methylene in their side chains ("homo" amino acids), and amino acids in which a carboxylic acid functional group in the side chain is replaced with a sulfonic acid group (cysteic acid, etc.).

Naturally occurring amino acid residues can be classified into, for example, the following groups based on general side chain characteristics:
(1) hydrophobic residues: Met, Ala, Val, Leu, and Ile;
(2) neutral hydrophilic residues: Cys, Ser, and Thr;
(3) acidic residues: Asp and Glu;
(4) basic residues: Asn, Gln, His, Lys, and Arg;
(5) residues influencing chain orientation: Gly and Pro; and
(6) aromatic residues: Trp, Tyr, and Phe.

The non-conservative substitution of an amino acid sequence constituting the antibody or the antigen-binding fragment thereof may be performed by replacing an amino acid belonging to one of these groups with an amino acid belonging to any of the other groups. More conservative substitution may be performed by replacing an amino acid belonging to one of these groups with another amino acid belonging to the same group thereas. Likewise, the deletion or the substitution in an amino acid sequence may be appropriately performed.

The modification of amino acid(s) constituting the antibody or the antigen-binding fragment thereof may be, for example, a posttranslational modification such as glycosylation with a sugar, acetylation, or phosphorylation. The antibody may be glycosylated at a conserved position in its constant region. The glycosylation of the antibody is usually of N-linked or O-linked type. The N-linked glycosylation means the binding of a carbohydrate moiety to the side chain of an asparagine residue. Tripeptide sequences asparagine-X-serine, asparagine-X-threonine, and asparagine-X-cysteine (wherein X is any amino acid other than proline) are recognition sequences for enzymatically adding a carbohydrate moiety to the asparagine side chain. Any of these tripeptide sequences are present in the antibody or the antigen-binding fragment thereof so that a potential glycosylation site is present. The O-linked glycosylation may be the binding of N-acetylgalactosamine, galactose, or xylose to a hydroxyamino acid (e.g., serine or threonine), or may be the binding thereof to 5-hydroxyproline or 5-hydroxylysine in some cases. Those skilled in the art can appropriately select the glycosylation conditions (in the case of performing the glycosylation by use of a biological approach, for example, host cells and the type and pH of a cell medium) according to the purpose.

The anti-EphA4 antibody or the EphA4-binding fragment thereof of the present invention can be further modified by using other modification methods alone or in combination on the basis of the technical common sense generally known to those skilled in the art.

The anti-EphA4 antibody or the EphA4-binding fragment thereof of the present invention can be produced by a method well known to those skilled in the art. For example, a hybridoma producing the anti-EphA4 antibody or the EphA4-binding fragment thereof of the present invention may be used to produce an antibody, or a gene encoding the anti-EphA4 antibody or the EphA4-binding fragment thereof of the present invention may be integrated into an expression vector, which can then be transferred to E. coli cells, monkey COS cells, Chinese hamster ovary (CHO) cells, or the like to produce an antibody. The gene encoding the anti-EphA4 antibody or the EphA4-binding fragment thereof of the present invention preferably has DNA encoding a signal sequence and more preferably has DNA encoding a signal sequence at each of the 5' ends of DNA encoding the heavy chain variable region and DNA encoding the light chain variable region. The signal sequence is amino acid residues located at the N-terminus of a protein, which are required for a secretory protein or an integral membrane protein to pass through the lipid bilayer after being synthesized on the ribosome. The signal sequence according to the present invention is not particularly limited as long as the sequence has this function. Examples of the signal sequence that may be contained in the anti-EphA4 antibody or the EphA4-binding fragment thereof of the present invention include signal sequences derived from a human, a mouse, a rat, a rabbit, a donkey, a goat, a horse, a chicken, a dog, a cat, a yeast, and the like. A specific aspect of the signal sequence includes a peptide comprising the amino acid sequence represented by SEQ ID NO: 10 or SEQ ID NO: 55 as the signal sequence for the heavy chain, and a peptide comprising the amino acid sequence represented by SEQ ID NO: 12 or SEQ ID NO: 58 as the signal sequence for the light chain. The amino acid sequence represented by SEQ ID NO: 10, the amino acid sequence represented by SEQ ID NO: 55, the amino acid sequence represented by SEQ ID NO: 12 or the amino acid sequence represented by SEQ ID NO: 58 may have the substitution, addition, and/or deletion of one or more (e.g., 2, 3, 4, or 5) amino acids as long as the resulting sequence is functionally equivalent thereto.

The anti-EphA4 antibody or the EphA4-binding fragment thereof of the present invention may be isolated or purified according to a method generally known to those skilled in the art. In this context, the term "isolated" or "purified" means being artificially isolated or purified from a natural state. When a naturally occurring molecule or composition is altered or removed from its original environment, or both, the molecule or the composition is "isolated" or "purified". Examples of the isolation or purification method include electrophoretic, molecular biological, immunological, and chromatographic approaches and specifically include, but are not limited to, ion-exchange chromatography, hydrophobic chromatography, reverse-phase HPLC chromatography, and isoelectric focusing electrophoresis.

In an alternative preferred embodiment of the present invention, the anti-EphA4 antibody or the EphA4-binding fragment thereof has the following CDRs:
(a) CDR-H1 comprising the amino acid sequence represented by SEQ ID NO: 26 or SEQ ID NO: 27;
(b) CDR-H2 comprising the amino acid sequence represented by SEQ ID NO: 28 or SEQ ID NO: 29;
(c) CDR-H3 comprising the amino acid sequence represented by SEQ ID NO: 30;
(d) CDR-L1 comprising the amino acid sequence represented by SEQ ID NO: 31;
(e) CDR-L2 comprising the amino acid sequence represented by SEQ ID NO: 32; and (f) CDR-L3 comprising the amino acid sequence represented by SEQ ID NO: 33.

In one embodiment of the present invention, the anti-EphA4 antibody or the EphA4-binding fragment thereof is a humanized antibody or a chimeric antibody, preferably a humanized antibody.

In an alternative preferred embodiment of the present invention, the anti-EphA4 antibody or the EphA4-binding fragment thereof has the following CDRs:

(a) CDR-H1 comprising the amino acid sequence represented by SEQ ID NO: 26;

(b) CDR-H2 comprising the amino acid sequence represented by SEQ ID NO: 28;

(c) CDR-H3 comprising the amino acid sequence represented by SEQ ID NO: 30;

(d) CDR-L1 comprising the amino acid sequence represented by SEQ ID NO: 31;

(e) CDR-L2 comprising the amino acid sequence represented by SEQ ID NO: 32; and (f) CDR-L3 comprising the amino acid sequence represented by SEQ ID NO: 33.

In an alternative preferred embodiment of the present invention, the anti-EphA4 antibody or the EphA4-binding fragment thereof has the following CDRs:

(a) CDR-H1 comprising the amino acid sequence represented by SEQ ID NO: 27;

(b) CDR-H2 comprising the amino acid sequence represented by SEQ ID NO: 29;

(c) CDR-H3 comprising the amino acid sequence represented by SEQ ID NO: 30;

(d) CDR-L1 comprising the amino acid sequence represented by SEQ ID NO: 31;

(e) CDR-L2 comprising the amino acid sequence represented by SEQ ID NO: 32; and (f) CDR-L3 comprising the amino acid sequence represented by SEQ ID NO: 33.

In an alternative preferred embodiment of the present invention, the anti-EphA4 antibody or the EphA4-binding fragment thereof comprises a heavy chain and a light chain, a variable region of the heavy chain comprises the amino acid sequence represented by SEQ ID NO: 11 or an amino acid sequence derived from the sequence by the substitution, addition, and/or deletion of one or more amino acids, and a variable region of the light chain comprises the amino acid sequence represented by SEQ ID NO: 13 or an amino acid sequence derived from the sequence by the substitution, addition, and/or deletion of one or more amino acids.

In an alternative preferred embodiment of the present invention, the anti-EphA4 antibody or the EphA4-binding fragment thereof comprises a heavy chain and a light chain, wherein a variable region of the heavy chain comprises the amino acid sequence represented by SEQ ID NO: 66, 68, 70, 72, 74 or 76, or an amino acid sequence derived from said sequence by substitution, addition, and/or deletion of one or more amino acids, and a variable region of the light chain comprises the amino acid sequence represented by SEQ ID NO: 78, 80, 82 or 84, or an amino acid sequence derived from said sequence by the substitution, addition, and/or deletion of one or more amino acids.

In this context, the term "or more" used as to the heavy chain variable region or the light chain variable region in the anti-EphA4 antibody or the EphA4-binding fragment thereof of the present invention is not limited as long as it maintains binding affinity for EphA4 and inhibits the binding between EphA4 and ephrin. The term "or more" is 2 to 15, more preferably 2 to 10, for example, 9, 8, 7, 6, 5, 4, 3, or 2 or is within 10%, for example, within 9%, within 8%, within 7%, within 6%, within 5%, within 4%, within 3%, within 2%, or within 1% of the number of amino acids in the amino acid sequence.

In an alternative preferred embodiment of the present invention, the anti-EphA4 antibody or the EphA4-binding fragment thereof comprises a heavy chain variable region and a light chain variable region, the heavy chain variable region comprises the amino acid sequence represented by of SEQ ID NO: 11, and the light chain variable region comprises the amino acid sequence represented by SEQ ID NO: 13.

In an alternative preferred embodiment of the present invention, the anti-EphA4 antibody or the EphA4-binding fragment thereof comprises a heavy chain variable region and a light chain variable region, wherein said heavy chain variable region comprises the amino acid sequence represented by SEQ ID NO: 66, 68, 70, 72, 74 or 76, and said light chain variable region comprises the amino acid sequence represented by SEQ ID NO: 78, 80, 82 or 84.

In an alternative preferred embodiment of the present invention, the anti-EphA4 antibody or the EphA4-binding fragment thereof comprises a heavy chain variable region and a light chain variable region, wherein said heavy chain variable region comprises the amino acid sequence represented by SEQ ID NO: 66, and said light chain variable region comprises the amino acid sequence represented by SEQ ID NO: 78, or said heavy chain variable region comprises the amino acid sequence represented by SEQ ID NO: 68, and said light chain variable region comprises the amino acid sequence represented by SEQ ID NO: 78, or said heavy chain variable region comprises the amino acid sequence represented by SEQ ID NO: 70, and said light chain variable region comprises the amino acid sequence represented by SEQ ID NO: 78, or said heavy chain variable region comprises the amino acid sequence represented by SEQ ID NO: 72, and said light chain variable region comprises the amino acid sequence represented by SEQ ID NO: 78, or said heavy chain variable region comprises the amino acid sequence represented by SEQ ID NO: 74, and said light chain variable region comprises the amino acid sequence represented by SEQ ID NO: 78, or said heavy chain variable region comprises the amino acid sequence represented by SEQ ID NO: 76, and said light chain variable region comprises the amino acid sequence represented by SEQ ID NO: 78.

In an alternative preferred embodiment of the present invention, an anti-EphA4 antibody or an EphA4-binding fragment thereof comprises a heavy chain variable region and a light chain variable region, wherein said heavy chain variable region comprises the amino acid sequence represented by SEQ ID NO: 66, and said light chain variable region comprises the amino acid sequence represented by SEQ ID NO: 80, or said heavy chain variable region comprises the amino acid sequence represented by SEQ ID NO: 68, and said light chain variable region comprises the amino acid sequence represented by SEQ ID NO: 80, or said heavy chain variable region comprises the amino acid sequence represented by SEQ ID NO: 70, and said light chain variable region comprises the amino acid sequence represented by SEQ ID NO: 80, or said heavy chain variable region comprises the amino acid sequence represented by SEQ ID NO: 72, and said light chain variable region comprises the amino acid sequence represented by SEQ ID NO: 80, or said heavy chain variable region comprises the amino acid sequence represented by SEQ ID NO: 74, and said light chain variable region comprises the amino acid sequence represented by SEQ ID NO: 80, or said heavy chain variable region comprises the amino acid sequence represented by SEQ ID NO: 76, and said light chain variable region comprises the amino acid sequence represented by SEQ ID NO: 80.

In an alternative preferred embodiment of the present invention, an anti-EphA4 antibody or an EphA4-binding fragment thereof comprises a heavy chain variable region and a light chain variable region, wherein said heavy chain variable region comprises the amino acid sequence represented by SEQ ID NO: 66, and said light chain variable region comprises the amino acid sequence represented by SEQ ID NO: 82, or said heavy chain variable region comprises the amino acid sequence represented by SEQ ID NO: 68, and said light chain variable region comprises the amino acid sequence represented by SEQ ID NO: 82, or said heavy chain variable region comprises the amino acid sequence represented by SEQ ID NO: 70, and said light chain variable region comprises the amino acid sequence represented by SEQ ID NO: 82, or said heavy chain variable region comprises the amino acid sequence represented by SEQ ID NO: 72, and said light chain variable region comprises the amino acid sequence represented by SEQ ID NO: 82, or said heavy chain variable region comprises the amino acid sequence represented by SEQ ID NO: 74, and said light chain variable region comprises the amino acid sequence represented by SEQ ID NO: 82, or said heavy chain variable region comprises the amino acid sequence represented by SEQ ID NO: 76, and said light chain variable region comprises the amino acid sequence represented by SEQ ID NO: 82.

In an alternative preferred embodiment of the present invention, an anti-EphA4 antibody or an EphA4-binding fragment thereof comprises a heavy chain variable region and a light chain variable region, wherein said heavy chain variable region comprises the amino acid sequence represented by SEQ ID NO: 66, and said light chain variable region comprises the amino acid sequence represented by SEQ ID NO: 84, or said heavy chain variable region comprises the amino acid sequence represented by SEQ ID NO: 68, and said light chain variable region comprises the amino acid sequence represented by SEQ ID NO: 84, or said heavy chain variable region comprises the amino acid sequence represented by SEQ ID NO: 70, and said light chain variable region comprises the amino acid sequence represented by SEQ ID NO: 84, or said heavy chain variable region comprises the amino acid sequence represented by SEQ ID NO: 72, and said light chain variable region comprises the amino acid sequence represented by SEQ ID NO: 84, or said heavy chain variable region comprises the amino acid sequence represented by SEQ ID NO: 74, and said light chain variable region comprises the amino acid sequence represented by SEQ ID NO: 84, or said heavy chain variable region comprises the amino acid sequence represented by SEQ ID NO: 76, and said light chain variable region comprises the amino acid sequence represented by SEQ ID NO: 84.

In a specific embodiment of the present invention, an anti-EphA4 antibody or an EphA4-binding fragment thereof has a constant region of human $IgG_2$. Preferably, said human $IgG_2$ constant region has at least one amino acid mutation selected from C131S, C219S, V234A and G237A (EU numbering). In one embodiment, said human $IgG_2$ constant region has a combination of C131S and C219S amino acid mutations. In one embodiment, said human $IgG_2$ constant region has a combination of V234A and G237A amino acid mutations. In another embodiment, said human $IgG_2$ constant region has all amino acid mutations of C131S, C219S, V234A and G237A. In a further alternative embodiment, said human $IgG_2$ constant region does not have a lysine residue at the C-terminus.

In a preferred embodiment of the present invention, human $IgG_2$ constant region comprise the amino acid sequence represented by SEQ ID NO: 62.

In a specific embodiment of the present invention, an anti-EphA4 antibody or an EphA4-binding fragment thereof has human IgG constant region consisting of a combination of human $IgG_1$ and human $IgG_2$. Preferably, in said human IgG constant region, CH1 and a hinge region are human $IgG_1$, and CH2 and CH3 are human $IgG_2$. In one embodiment, said human IgG constant region has V234A or G237A (Eu numbering) amino acid mutation. In another aspect, said human IgG constant region has V234A and G237A amino acid mutations. In a further alternative aspect, said human IgG constant region does not have a lysine residue at the C-terminus.

In a preferred embodiment of the present invention, the human IgG constant region consisting of a combination of human $IgG_1$ and human $IgG_2$ comprises the amino acid sequence represented by SEQ ID NO: 60.

In one aspect, the present invention relates to a pharmaceutical composition comprising the anti-EphA4 antibody or the EphA4-binding fragment thereof of the present invention.

The pharmaceutical composition comprising the anti-EphA4 antibody or the EphA4-binding fragment thereof of the present invention may further comprise a pharmaceutically acceptable carrier, excipient, and/or stabilizer in the form of an aqueous or dry preparation. Examples of the acceptable carrier, excipient and/or stabilizer include: physiological saline; buffer solutions of phosphate, citrate, or other organic acids; antioxidants including ascorbic acid; low-molecular-weight polypeptides; proteins (e.g., serum albumin, gelatin, and immunoglobulins); hydrophilic polymers such as polyvinylpyrrolidone; amino acids; monosaccharides, disaccharides, and other carbohydrates, including glucose, mannose, and dextrins; chelating agents such as EDTA; sugar alcohols such as mannitol and sorbitol; salt-forming counterions such as sodium; and nonionic surfactants such as TWEEN (trademark), PLURONICS (trademark), and PEG.

The pharmaceutical composition comprising the anti-EphA4 antibody or the EphA4-binding fragment thereof of the present invention may be enclosed in, for example, a microcapsule, a colloidal drug delivery system (e.g., a liposome, an albumin microsphere, a microemulsion, a nanoparticle, or a nanocapsule), or a microemulsion. When the sustained-release administration of the antibody is desired for a preparation having release properties suitable for any disease in need of the administration of the antibody, the antibody may be intended to be microencapsulated. Examples of the sustained-release matrix include polyester, hydrogels (e.g., poly(2-hydroxyethyl-methacrylate) and poly(vinyl alcohol)), polylactic acids, copolymers of L-glutamic acid and γ-ethyl-L-glutamate, non-degradable ethylene-vinyl acetate, degradable lactic acid-glycolic acid copolymers (microspheres for injection constituted by a lactic acid-glycolic acid copolymer and leuprolide acetate) such as LUPRON DEPOT (trademark), and poly-D-(-)-3-hydroxybutyric acid.

In one aspect, the anti-EphA4 antibody or the EphA4-binding fragment thereof of the present invention can inhibit the binding between EphA4 and its ligand. Therefore, the pharmaceutical composition comprising the anti-EphA4 antibody or the EphA4-binding fragment thereof of the present invention may be useful in the treatment of ALS. Specifically, an alternative aspect of the present invention encompasses a method for treating ALS, comprising the step of administering a therapeutic effective amount of the anti-EphA4 antibody or the EphA4-binding fragment thereof of the present invention to a subject. An alternative aspect of the present invention encompasses use of the anti-EphA4 antibody or the EphA4-binding fragment thereof of the present invention for producing a therapeutic drug for ALS. An alternative aspect of the present invention encompasses the anti-EphA4 antibody or the EphA4-binding fragment thereof for use in a method for treating ALS.

The anti-EphA4 antibody or the EphA4-binding fragment thereof of the present invention can be used alone or in combination with an additional drug or composition in the treatment method. For example, the anti-EphA4 antibody or the EphA4-binding fragment thereof of the present invention may be administered at the same time or at different times with an additional drug. Such combination therapy includes combined administration (two or more drugs are contained in the same preparation or separate preparations) and separated administration (e.g., concurrent or continuous). In the case of separately administering two or more drugs, the anti-EphA4 antibody or the EphA4-binding fragment thereof of the present invention can be administered prior to or following the concomitant treatment method.

The subject for administrating the pharmaceutical composition comprising the anti-EphA4 antibody or the EphA4-binding fragment thereof of the present invention is not limited, and the pharmaceutical composition of the present invention can be used for, for example, a human or a nonhuman mammal (a monkey, a mouse, a rat, a rabbit, cattle, a horse, a goat, etc.).

The method for administering the pharmaceutical composition comprising the anti-EphA4 antibody or the EphA4-binding fragment thereof of the present invention to the subject (administration route, dose, the number of doses per day, the timing of administration, etc.) is not limited and can be appropriately determined by those skilled in the art (e.g., a physician) according to the health condition of the subject, the severity of the disease, the type of a drug to be used in combination therewith, etc.

Those skilled in the art should understand that the present invention may be carried out by any one of or appropriate combination of two or more of all aspects described in the present specification unless a technical contradiction arises. Further, those skilled in the art should understood that the present invention can be preferably carried out by an appropriate combination of all preferable or advantageous aspects described in the present specification unless a technical contradiction arises.

Literatures cited in the present specification should be interpreted as being clearly incorporated herein by reference in their entirety. Those skilled in the art can understand related contents disclosed in these literatures by reference as a part of the present specification without departing from the spirits and scope of the present invention according to the context of the present specification.

Literatures cited in the present specification are provided merely for the purpose of disclosing related techniques before the filing date of the present application. It should not be understood that the present inventors admit to having no right preceding such disclosure due to the prior inventions or any other reasons. All statements of these literatures are based on information which has been available by the present applicant, and there is no admission that the contents of these statements are accurate.

The terms in the present specification are used for illustrating particular embodiments and are not intended to limit the invention.

The term "comprise" used in the present specification means that described items (members, steps, factors, numbers, etc.) are present and the presence of the other items (members, steps, factors, numbers, etc.) is not excluded therefrom, unless the context evidently requires different interpretation. The term "consist of" encompasses aspects described by the terms "consist of" and/or "consist essentially of".

The term "neutralizing activity" used in the present specification means the activity of inhibiting the binding between EphA4 and its ligand and/or the activity of inhibiting signal transduction or the molecular expression response or functional change of cells induced by the binding between EphA4 and its ligand in the living body of a human.

All terms (including technical terms and scientific terms) used herein have the same meanings as those understood in a broad sense by those skilled in the art to which the present invention belongs, unless otherwise defined. The terms used herein should be interpreted as having meanings consistent with meanings in the present specification and related technical fields and should not be interpreted in an idealized or excessively formal sense, unless otherwise defined.

Terms such as "first" or "second" are used for expressing various factors. However, these factors are understood to be not limited by these terms themselves. These terms are used merely for differentiating one factor from the other factors. For example, the first factor may be described as the second factor, and vice versa, without departing from the scope of the present invention.

In the present specification, it should be understood that numerical values used for indicating component contents, numerical ranges, etc., are modified with the term "approximately" unless otherwise specified. For example, "4° C." is interpreted as meaning "approximately 4° C." unless otherwise specified. Those skilled in the art can naturally understand the extent thereof rationally according to the technical common sense and the context of the present specification.

It should be understood that each aspect indicated in a singular form used in the present specification and claims may be in a plural form, and vice versa, unless the context evidently requires different interpretation and unless a technical contradiction arises.

Hereinafter, the present invention will be described in more detail with reference to Examples. However, the present invention can be embodied by various aspects and is not intended to be limited by Examples described herein. Those skilled in the art in the related field can implement the present invention by various modifications, additions, deletions, substitutions, etc., without altering the spirit or scope of the present invention.

EXAMPLES

Example 1

Preparation of Anti-mouse EphA4 Monoclonal Antibody

Preparation of Mouse Anti-mouse EphA4 Monoclonal Antibody

In order to prepare a monoclonal antibody binding to mouse EphA4 (GenBank Accession No. NP_031962.2, SEQ ID NO: 1), a protein of a mouse EphA4 extracellular region (positions 20 to 547) (SEQ ID NO: 2) fused with secreted alkaline phosphatase (SEAP) and histidine tag (hereinafter, referred to as "mouse EphA4 extracellular region-SEAP-His protein", SEQ ID NO: 43) was prepared by the following steps.

First, a DNA sequence encoding the signal sequence (SEQ ID NO: 42) and the extracellular region (SEQ ID NO: 2) of mouse EphA4 was amplified by RT-PCR using mouse brain-derived total RNA and cloned into the SalI/NotI site of a pENTR1A vector (Invitrogen/Life Technologies) having a DNA sequence encoding SEAP and histidine tag. Next, the DNA sequence encoding the signal sequence and the extracellular region of mouse EphA4, SEAP, and histidine tag was transferred to a pcDNA3.1_rfcB vector through LR reaction using Gateway System (Invitrogen/Life Technologies) to construct a pcDNA3.1-mouse EphA4 extracellular region-SEAP-His expression vector. HEK293EBNA cells (Invitrogen/Life Technologies) were transfected with the constructed pcDNA3.1-mouse EphA4 extracellular region-SEAP-His expression vector using TransIT-LT1 (TAKARA). After incubation (5% $CO_2$, 37° C.) for 6 days, the culture supernatant was recovered. From the recovered culture supernatant, the mouse EphA4 extracellular region-SEAP-His protein (SEQ ID NO: 43) was purified using Protino column (MACHEREY-NAGEL).

20 µg of the mouse EphA4 extracellular region-SEAP-His protein was mixed with the same amount of TiterMax Gold adjuvant (TiterMax USA) or GERBU adjuvant (GERBU Biotechnik), and the mixture was subcutaneously injected to the footpad of a Balb/c mouse. Then, at days 3, 7, and 10, the mouse EphA4 extracellular region-SEAP-His protein was administered in the same way as above. In this operation, the TiterMax Gold adjuvant (TiterMax USA) was used only for day 10, and the GERBU adjuvant (GERBU Biotechnik) was used for days 3, 7, and 10. At day 13, the mouse was sacrificed, and the peripheral lymph node was recovered to prepare lymph node cells. The prepared lymph node cells and P3U1 myeloma cells (kindly provided by Kyoto University) were fused at a ratio of 5:1 in the presence of GenomONE-CF (Ishihara Sangyo Kaisha). The fused cells were cultured in a 96-well plastic plate. After incubation (5% $CO_2$, 37° C.) for 7 days, the culture supernatant was recovered.

The obtained culture supernatant was used to pick up a well having reactivity with mouse, rat, and human EphA4 and inhibitory activity against the binding between mouse EphA4 and mouse Ephrin A1.

The reactivity with mouse, rat, and human EphA4 was evaluated by ELISA using a protein of the extracellular region of mouse EphA4, the extracellular region (positions 20 to 547) of rat EphA4 (GenBank Accession No. NP_001155883.1), or the extracellular region (positions 20 to 547) (SEQ ID NO: 4) of human EphA4 (GenBank Accession No. NP_004429.1, SEQ ID NO: 3) fused with a human IgG1 Fc region and histidine tag (hereinafter, referred to as "mouse EphA4 extracellular region-Fc-His protein", "rat EphA4 extracellular region-Fc-His protein", or "human EphA4 extracellular region-Fc-His protein", respectively).

The mouse, rat, or human EphA4 extracellular region-Fc-His protein was prepared by the following steps. First, a pcDNA3.1-mouse, rat, or human EphA4 extracellular region-Fc-His expression vector was constructed. First, a DNA sequence encoding the signal sequence and the extracellular region of mouse, rat, or human EphA4 was amplified by RT-PCR using mouse, rat, or human brain-derived total RNA and cloned into the SalI/NotI site of a pENTR1A vector (Invitrogen/Life Technologies) having a DNA sequence encoding Fc and histidine tag. Next, the DNA sequence encoding the signal sequence and the extracellular region of mouse, rat, or human EphA4, Fc, and histidine tag was transferred to a pcDNA3.1_rfcB vector through LR reaction using Gateway System (Invitrogen/Life Technologies) to construct a pcDNA3.1-mouse, rat, or human EphA4 extracellular region-Fc-His expression vector. HEK293EBNA cells (Invitrogen/Life Technologies) were transfected with each of the constructed expression vectors using TransIT-LT1 (TAKARA). After incubation (5% $CO_2$, 37° C.) for 6 days, each culture supernatant was recovered.

ELISA using the mouse, rat, or human EphA4 extracellular region-Fc-His protein was conducted according to the following steps. Each well of a 96-well plate (Nunc) was coated with an anti-human IgG antibody (Jackson ImmunoResearch Laboratories). After incubation overnight at 4° C., each well was blocked with 1×BlockAce (Sumitomo Dainippon Pharma) at room temperature for 1 hour. After washing with 0.02% Tween 20/PBS (Nacalai Tesque) three times, the culture supernatant containing the mouse, rat, or human EphA4 extracellular region-Fc-His protein was added (final concentration: 1 nM) to each well and incubated at room temperature for 1 hour. After washing three times, the culture supernatant of the fused cells was added to each well. After incubation at room temperature for 1 hour and subsequent washing three times, a horseradish peroxidase-labeled anti-mouse IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well and incubated at room temperature for 5 to 20 minutes. An equal amount of a reaction stopping solution (2N $H_2SO_4$, Wako Pure Chemical Industries) was added to each well. The absorbance at 450 nm was read using a microplate reader (PerkinElmer).

The inhibitory activity against the binding between mouse EphA4 and mouse Ephrin A1 was evaluated according to the following steps. Each well of a 96-well plate (Nunc) was coated with an anti-alkaline phosphatase antibody (Seradyn). After incubation overnight at 4° C., each well was blocked with 1×BlockAce (Sumitomo Dainippon Pharma) at room temperature for 1 hour. After washing with 0.02% Tween 20/PBS (Nacalai Tesque) three times, the mouse EphA4 extracellular region-SEAP-His protein was added (final concentration: 10 nM) to each well and incubated at room temperature for 1 hour. After washing three times, Ephrin A1-Fc chimera (R&D Systems, final concentration: 20 nM) and the culture supernatant of the fused cells were added to each well. After incubation at room temperature for 1 hour and subsequent washing three times, a horseradish peroxidase-labeled anti-human IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well and incubated at room temperature for 5 to 20 minutes. An equal amount of a reaction stopping solution (2N H$_2$SO$_4$, Wako Pure Chemical Industries) was added to each well. The absorbance at 450 nm was read using a microplate reader (PerkinElmer).

From the well picked up through these steps, a hybridoma was cloned by the limiting dilution method. Finally, a hybridoma clone expressing a mouse anti-EphA4 antibody having reaction activity against mouse, rat, and human EphA4 and having inhibitory activity against the binding between mouse EphA4 and mouse Ephrin A1 was obtained.

The obtained hybridoma clone was cultured, and the anti-EphA4 antibody (antibody A) was purified from the culture supernatant using protein A (GE Healthcare). The isotype of antibody A was determined using a monoclonal antibody isotyping kit (Serotec) and was IgG1 for the heavy chain and κ for the light chain.

Sequence Analysis of Antibody A

DNA sequences encoding the heavy chain and light chain signal sequences and variable regions of antibody A were amplified by 5'-RACE (5'-rapid amplification of cDNA ends). Total RNA was prepared from the hybridoma using TRIZOL (Invitrogen/Life Technologies) and treated with DNase (Qiagen N.V., RNase free DNase set). Double-stranded cDNA was prepared from the total RNA using a cDNA synthesis kit (TAKARA). 5' adaptor obtained by the annealing of oligo DNA ad29S (ACATCACTCCGT) (SEQ ID NO: 5) and oligo DNA ad29AS (ACGGAGTGATGTC-CGTCGACGTATCTCTGCGTTGATACTTCAGCG-TAGCT) (SEQ ID NO: 6) was added to the cDNA. The obtained cDNA was amplified using 5' forward primer (5'-PCR4 primer, AGCTACGCTGAAGTATCAACGCA-GAG) (SEQ ID NO: 7) and 3' reverse primer (GCCAGTG-GATAGACTGATGG (SEQ ID NO: 8) was used for the amplification of the mouse IgG heavy chain gene, and GATGGATACAGTTGGTGCAGC (SEQ ID NO: 9) was used for the amplification of the mouse Igκ light chain gene). The amplified cDNA was inserted to a pCR2.1 vector (Invitrogen/Life Technologies). The gene sequence of antibody A was analyzed using ABI3130XL. As for the amino acid sequence encoded by the gene sequence of antibody A identified by this analysis, the heavy chain signal sequence is shown in SEQ ID NO: 10; the heavy chain variable region is shown in SEQ ID NO: 11; the light chain signal sequence is shown in SEQ ID NO: 12; and the light chain variable region is shown in SEQ ID NO: 13. As for the nucleotide sequence encoding the gene sequence of antibody A, the heavy chain signal sequence is shown in SEQ ID NO: 14, the heavy chain variable region is shown in SEQ ID NO: 15; the light chain signal sequence is shown in SEQ ID NO: 16; and the light chain variable region is shown in SEQ ID NO: 17.

The full-length sequences of the heavy chain and the light chain of antibody A were obtained by the following steps. Total RNA was prepared from the hybridoma using TRIZOL (Invitrogen/Life Technologies) and treated with DNase (Qiagen N.V., RNase free DNase set). cDNA was prepared from the total RNA using a cDNA synthesis kit (TAKARA). The obtained cDNA was used as a template in PCR to amplify the gene sequences encoding the antibody A heavy chain and light chain using 5' forward primer (GC-GAAGCTTGCCGCCACCATGGCTTGGGTGTGGACCT-TGC (SEQ ID NO: 18) was used for the amplification of the heavy chain gene, and GCGAAGCTTGCCGCCACCAT-GAGTGTGCCCACTCAGGTCC (SEQ ID NO: 19) was used for the amplification of the light chain gene) and 3' reverse primer (GCGGAATTCATCATTTACCAGGA-GAGTGGGAGAGGC (SEQ ID NO: 20) was used for the amplification of the heavy chain gene, and CGCGAAT-TCACTAACACTCATTCCTGTTGAAGCTCTTGAC (SEQ ID NO: 21) was used for the amplification of the light chain gene). The amplification products were cloned into pEE6.4 and pEE12.4 vectors (Lonza), respectively. These gene sequences were analyzed using ABI3130XL. As for the amino acid sequence encoded by the gene sequence of antibody A identified by this analysis, the heavy chain constant region is shown in SEQ ID NO: 22, and the light chain constant region is shown in SEQ ID NO: 23. As for the nucleotide sequence encoding the gene sequence of antibody A, the heavy chain constant region is shown in SEQ ID NO: 24, and the light chain constant region is shown in SEQ ID NO: 25.

CDRs of antibody A were determined by numbering the amino acid sequence of antibody A using Abysis software (UCL) according to the Kabat numbering system and identifying the CDRs according to the Kabat definition or the AbM definition method on the basis of the numbers. The CDR amino acid sequences and nucleotide sequences of antibody A are shown in Tables 1 and 2, respectively.

TABLE 1

Table 1 Amino acid sequences of CDRs of antibody A

| Name | Sequence |
|---|---|
| Heavy chain CDR 1 (Kabat definition) | DYSMH (SEQ ID NO: 26) |
| Heavy chain CDR 1 (AbM definition) | GYTFDYSMH (SEQ ID NO: 27) |
| Heavy chain CDR 2 (Kabat definition) | WINTETGEPTYADDFKG (SEQ ID NO: 28) |
| Heavy chain CDR 2 (AbM definition) | WINTETGEPT (SEQ ID NO: 29) |
| Heavy chain CDR 3 | IPLYYYGSHYWYFDV (SEQ ID NO: 30) |
| Light chain CDR 1 | RASENIYRNLA (SEQ ID NO: 31) |
| Light chain CDR 2 | AATNLAD (SEQ ID NO: 32) |
| Light chain CDR 3 | QHPNGTPWT (SEQ ID NO: 33) |

TABLE 2

Table 2 Nucleic acid sequences of CDRs of antibody A

| Name | Sequence |
|---|---|
| Heavy chain CDR 1 (Kabat definition) | GACTATTCAATGCAC (SEQ ID NO: 34) |
| Heavy chain CDR 1 (AbM definition) | GGTTATACCTTCACAGACTATTCAATGCAC (SEQ ID NO: 35) |
| Heavy Chain CDR 2 (Kabat definition) | TGGATAAACACTGAGACTGGTGAGCCAACATAT GCAGATGACTTCAAGGGA (SEQ ID NO: 36) |

TABLE 2-continued

Table 2 Nucleic acid sequences of CDRs of antibody A

| Name | Sequence |
|---|---|
| Heavy chain CDR 2 (AbM definition) | TGGATAAACACTGAGACTGGTGAGCCAACA (SEQ ID NO: 37) |
| Heavy chain CDR 3 | ATTCCCCTCTATTACTACGGTAGTAGGTAC TGGTACTTCGATGTC (SEQ ID NO: 38) |
| Light chain CDR 1 | CGAGCAAGTGAGAATATTTACAGAAATTTAGCA (SEQ ID NO: 39) |
| Light chain CDR 2 | GCTGCAACAAACTTAGCAGAT (SEQ ID NO: 40) |
| Light chain CDR 3 | CAACATTTTTGGGGTACTCCGTGGACG (SEQ ID NO: 41) |

Example 2

Binding Affinity of Anti-EphA4 Monoclonal Antibody for Mouse and Human EphA4

The binding affinity of antibody A obtained in Example 1 for mouse and human EphA4 was determined by surface plasmon resonance (SPR) using Biacore A100 (GE Healthcare). First, a rat anti-mouse $IgG_1$ antibody produced with a conventional procedure by immunizing rat with a mouse $IgG_1$ antibody was immobilized on sensor chip CM5. The immobilization of the rat anti-mouse IgG1 antibody on sensor chip CM5 was performed by the amine coupling method using N-hydroxysuccinimide (NHS) and N-ethyl-N'-(3-dimethylaminopropyl)carbodiimide hydrochloride (EDC). Ethanolamine was used in blocking (the sensor chip and the reagents for immobilization were all manufactured by GE Healthcare). The antibody was diluted with a buffer solution for immobilization (10 mM sodium acetate, pH 4.5) into 1 to 2 µg/mL and immobilized on the sensor chip according to the protocol attached to Biacore A100. Antibody A was diluted with a running buffer solution HBS-EP (GE Healthcare, BR-1001-88), injected onto a flow cell for 120 seconds, and captured (amount of the antibody captured: approximately 70 to 100 RU). Subsequently, mouse or human EphA4 extracellular region-SEAP-His serially diluted in the range of 50, 25, 12.5, 6.3, 3.1, 1.6, 0.8, and 0 nM using HBS-EP was added to the sensor chip for 120 seconds. Binding reaction curves were sequentially observed at the time of the addition (association phase, for 120 sec) and after the completion of the addition (dissociation phase, for 900 sec). After the completion of each observation, the sensor chip was regenerated by the addition of 3 M $MgCl_2$ (Wako Pure Chemical Industries, Ltd.) (for 30 sec). The obtained binding reaction curves were subjected to fitting analysis with 1:1 binding models using software BIA evaluation attached to the system to calculate the binding affinity (KD=kd/ka) for mouse and human EphA4.

The binding affinity (KD) of antibody A for mouse and human EphA4 was $7.29 \times 10^{-10}$ M and $6.61 \times 10^{-10}$ M, respectively (FIG. 1). Other binding parameters for mouse and human EphA4 were almost equivalent. Accordingly, antibody A is considered to have equivalent binding affinity for mouse and human EphA4.

Example 3

Mouse EphA4-mouse Ligand Binding Inhibitory Activity of Anti-EphA4 Monoclonal Antibody Antibody A obtained in Example 1 was evaluated for its inhibitory activity against the binding between mouse EphA4 and its mouse ligand according to the following steps. Each well of a 96-well plate (Nunc) was coated with an anti-alkaline phosphatase antibody (Thermo Fisher Scientific). After incubation overnight at 4° C., each well was blocked with 1% BlockAce (DS Pharma Biomedical) at room temperature for 1 hour. After washing with 0.05% Tween 20/PBS (Thermo Fisher Scientific) three times, the mouse EphA4 extracellular region-SEAP-His protein obtained by the method of Example 1 was added (final concentration: 10 nM) to each well and incubated at room temperature for 1 hour. After washing three times, ligands and serially diluted antibody A (0, 0.001, 0.003, 0.01, 0.03, 0.1, 0.3, 1,3, 10, 30, 100, 300, and 1000 nM) or a known EphA4 inhibitor KYL peptide (KYLPYWPVLSSL, 0, 0.003, 0.01, 0.03, 0.1, 0.3, 1, 3, 10, 30, and 100 µM, its synthesis was outsourced to Hokkaido System Science) or compound 1 (0, 0.03, 0.1, 0.3, 1,3, 10, 30, 100, 300, and 1000 µM, Formula 1, Matrix Scientific) were added to each well. The ligands used were mouse Ephrin A1-Fc chimera (R&D Systems, final concentration: 20 nM) and mouse Ephrin B2-Fc chimera (R&D Systems, final concentration: 0.6 nM). After incubation at room temperature for 1 hour and subsequent washing three times, a horseradish peroxidase-labeled anti-human IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well and incubated at room temperature for 2 minutes. An equal amount of a reaction stopping solution (1N $H_2SO_4$, Wako Pure Chemical Industries) was added to each well. The absorbance at 450 nm was read using a microplate reader (Molecular Devices).

[Formula 1]

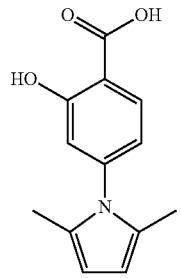

Formula 1

Antibody A suppressed the binding between mouse EphA4 and its mouse ligand in a concentration-dependent manner with $IC_{50}$ values of approximately 1.2 and 1.2 nM for binding to mouse Ephrin A1 and Ephrin B2, respectively. The $IC_{50}$ values of the existing EphA4 inhibitor KYL peptide were approximately 1.3 and 1.3 µM for binding to mouse Ephrin A1 and Ephrin B2, respectively (FIG. 2). Compound 1 had weaker activity, and no concentration dependence was found. Accordingly, antibody A was found to inhibit the binding between mouse EphA4 and mouse ligand with the activity 1,000 or more times stronger than that of the existing EphA4 inhibitor KYL peptide.

Example 4

Human EphA4-human Ligand Binding Inhibitory Activity of Anti-EphA4 Monoclonal Antibody Antibody A obtained in Example 1 was evaluated for its inhibitory activity against the binding between human EphA4 and its human ligand according to the following steps. Each well of a 96-well plate (Nunc) was coated with an anti-alkaline phosphatase antibody (Thermo Fisher Scientific). After incubation overnight at 4° C., each well was blocked with 1% BlockAce (DS Pharma Biomedical) at room temperature for 1 hour. After washing with 0.05% Tween 20/PBS (Thermo Fisher Scientific) three times, the human EphA4 extracellular region-SEAP-His protein obtained by the method of Example 1 was added (final concentration: 10 nM) to each well and incubated at room temperature for 1 hour. After washing three times, ligands and serially diluted antibody A (0, 0.003, 0.01, 0.03, 0.1, 0.3, 1, 3, 10, 30, 100, 300, 1000, and 3000 nM) or an EphA4 inhibitor KYL peptide (KYLPYWPVLSSL, 0, 0.003, 0.01, 0.03, 0.1, 0.3, 1, 3, 10, 30, 100, 300, 1000, and 3000 µM, its synthesis was outsourced to Toray Research Center) were added to each well. The ligands used were biotinylated human Ephrin A5-Fc chimera (R&D Systems, final concentration: 0.7 nM) and biotinylated human Ephrin B3-Fc chimera (R&D Systems, final concentration: 2.3 nM). After incubation at room temperature for 1 hour and subsequent washing three times, horseradish peroxidase-labeled streptavidin (GE Healthcare) was added thereto and incubated at room temperature for 1 hour. After washing three times, a TMBZ (3,3',5,5'-tetramethylbenzidine, Sigma-Aldrich) solution was added to each well and incubated at room temperature for 2 minutes. An equal amount of a reaction stopping solution (1 N $H_2SO_4$, Wako Pure Chemical Industries) was added to each well. The absorbance at 450 nm was read using a microplate reader (Molecular Devices or PerkinElmer).

Antibody A suppressed the binding between human EphA4 and its human ligand in a concentration-dependent manner with $IC_{50}$ values of approximately 2.7 and 1.9 nM for binding to human Ephrin A5 and Ephrin B3, respectively. The $IC_{50}$ values of the EphA4 inhibitor KYL peptide were approximately 6.1 and 1.6 µM for binding to human Ephrin A5 and Ephrin B3, respectively (FIG. 3). Accordingly, antibody A was also found to strongly inhibit the binding between human EphA4 and its human ligand.

Example 5

Binding Affinity of EphA4-binding Fragment for Mouse and Human EphA4

First, a Fab fragment and a $F(ab')_2$ fragment of antibody A (hereinafter, referred to as antibody A-Fab and antibody A-$F(ab')_2$, respectively) were prepared as EphA4-binding fragments.

The preparation of antibody A-Fab was performed according to the following steps. In a 1.5-mL tube (Eppendorf), antibody A (4.36 mg/mL, 1 mL), 10 mM L-cysteine (Wako Pure Chemical Industries), 1 mM EDTA (Gibco), and 2.18 µg/mL papain (Sigma-Aldrich) were mixed and incubated at 37° C. for 12 hours. Iodoacetamide (Wako Pure Chemical Industries) was added at a final concentration of 50 mM to the tube after the incubation. After the termination of the reaction, the antibody solution was dialyzed against PBS (Sigma-Aldrich). To the antibody solution, an equal amount of 0.1 M Tris (Sigma-Aldrich)-HCl/5 M NaCl (pH 8.0, Wako Pure Chemical Industries) was added, followed by purification using rProtein A FF resin. A 2-mL tube was filled with 800 µL of rProtein A FF, which was then equilibrated by the addition of 3.5 C.V. each of ultrapure water and a binding buffer (0.1 M Tris (Sigma-Aldrich)-HCl/3 M NaCl (pH 8.0, Wako Pure Chemical Industries)) in this order. The antibody solution supplemented with an equal amount of 0.1 M Tris (Sigma-Aldrich)-HCl/5 M NaCl (Wako Pure Chemical Industries) (pH 8.0) was injected to the column. A solution eluted from the column (flow-through fraction) was recovered and added again to the column. This operation was repeated three times. Then, the flow-through fraction of the final run was recovered. Washing was repeated twice by the addition of 2.5 mL of a binding buffer. The flow-through and washing fractions were dialyzed against PBS to obtain antibody A-Fab.

The preparation of antibody A-$F(ab')_2$ was performed according to the following steps. Antibody A was dialyzed against a 0.2 M acetate buffer (pH 4.0, Wako Pure Chemical Industries) overnight at 4° C. The dialyzed solution was recovered and filtered through a 0.22-µm filter (Merck Millipore), and then quantified, and the antibody concentration was adjusted to 4.0 mg/mL. Pepsin (Sigma-Aldrich) was brought back to room temperature and adjusted to 2.0 mg/mL using a 0.2 M acetate buffer (pH 4.0, Wako Pure Chemical Industries). In a 1.5-mL tube (Eppendorf), antibody A (4.0 mg/mL, 800 µL), the pepsin solution (2.0 mg/mL, 16 µL), and a 0.2 M acetate buffer (pH 4.0, Wako Pure Chemical Industries) were mixed at 64 µL/tube and incubated at 37° C. for 15 hours. The reaction was terminated by the addition of 2 M Tris-base (Sigma-Aldrich) at 112 µL/tube to the tube after the incubation. Then, the molecular species was confirmed by SDS-PAGE. After the termination of the reaction, the antibody solution was dialyzed against 100 mM Tris-HCl (pH 8.0). Subsequently, antibody A-$F(ab')_2$ was purified using rProtein A FF (GE Healthcare, 17-1279-02). A 5-mL tube was filled with 1 mL of rProtein A resin, which was then equilibrated by the addition of 3.5 C.V. each of ultrapure water and a binding buffer in this order. The dialyzed antibody solution equilibrated by the addition of an equal amount of 0.1 M Tris (Sigma-Aldrich)-HCl/5 M NaCl (pH 8.0, Wako Pure Chemical Industries) was injected to the column. A flow-through fraction was recovered and added again to the column. This operation was repeated three times. Then, the flow-through fraction of the final run was recovered. Then, washing was repeated twice by the addition of 5 mL of a binding buffer. In order to remove unreacted IgG, etc., elution was performed with 0.1 M citrate (pH 3.0, Wako Pure Chemical Industries). Then, the molecular species was confirmed by SDS-PAGE. The flow-through and washing fractions were dialyzed against PBS to obtain antibody A-$F(ab')_2$.

Next, the binding affinity of antibody A-Fab and antibody A-$F(ab')_2$ for mouse and human EphA4 was determined by surface plasmon resonance (SPR) using Biacore T200 (GE Healthcare). Antibody A obtained in Example 1 was used as a control for the comparison of each fragment. First, an anti-His tag antibody was immobilized on sensor chip CM5. The immobilization of the anti-His tag antibody on sensor chip CM5 was performed by the amine coupling method using N-hydroxysuccinimide (NHS) and N-ethyl-N'-(3-dimethylaminopropyl)carbodiimide hydrochloride (EDC). Ethanolamine was used in blocking (the sensor chip and the reagents for immobilization were all manufactured by GE Healthcare). The antibody was diluted with a buffer solution for immobilization (10 mM sodium acetate, pH 4.5) into 3 µg/mL and immobilized on the sensor chip according to the protocol attached to Biacore T200.

Mouse or human EphA4 extracellular region-SEAP-His protein was diluted with a running buffer solution HBS-EP (GE Healthcare, BR-1001-88), injected onto a flow cell for 120 seconds, and captured (amount of the protein captured: approximately 10 to 20 RU). Subsequently, antibody A (50, 16.7, 5.6, 1.9, 0.6, and 0 nM), antibody A-Fab (500, 166.7, 55.6, 18.5, 6.2, and 0 nM), or antibody A-F(ab')$_2$ (50, 16.7, 5.6, 1.9, 0.6, and 0 nM) serially diluted using HBS-EP was added to the sensor chip for 120 seconds. Binding reaction curves were sequentially observed at the time of the addition (association phase, for 120 sec) and after the completion of the addition (dissociation phase, for 900 sec). After the completion of each observation, the sensor chip was regenerated by the addition of 3 M MgCl$_2$ (Wako Pure Chemical Industries) (for 30 sec). The obtained binding reaction curves were subjected to fitting analysis with 1:1 binding models using software BIA evaluation attached to the system to calculate the binding affinity (KD=kd/ka) for mouse and human EphA4.

The binding affinity (KD) of antibody A-Fab for mouse and human EphA4 was $4.51\times10^{-8}$ M and $4.04\times10^{-8}$ M, respectively (FIGS. 4A and 4C). On the other hand, the binding affinity (KD) of antibody A-F(ab')$_2$ for mouse and human EphA4 was $2.29\times10^{-11}$ M and $5.30\times10^{-11}$ M, respectively (FIGS. 4B and 4D).

Example 6

Mouse EphA4-mouse Ligand Binding Inhibitory Activity of EphA4-binding Fragment

Antibody A-Fab and antibody A-F(ab')$_2$ obtained in Example 5 were evaluated for their inhibitory activity against the binding between EphA4 and its ligand according to the following steps. Each well of a 96-well plate (Nunc) was coated with an anti-alkaline phosphatase antibody (Thermo Fisher Scientific). After incubation overnight at 4° C., each well was blocked with 1% BlockAce (DS Pharma Biomedical) at room temperature for 1 hour. After washing with 0.05% Tween 20/PBS (Thermo Fisher Scientific) three times, the mouse EphA4 extracellular region-SEAP-His protein obtained by the method of Example 1 was added (final concentration: 10 nM) to each well and incubated at room temperature for 1 hour. After washing three times, a ligand and serially diluted antibody A (0, 0.003, 0.01, 0.03, 0.1, 0.3, 1, 3, 10, 30, 100, 300, 1000, and 3000 nM), antibody A-Fab (0, 0.003, 0.01, 0.03, 0.1, 0.3, 1, 3, 10, 30, 100, 300, 1000, and 3000 nM), antibody A-F(ab')$_2$ (0, 0.003, 0.01, 0.03, 0.1, 0.3, 1, 3, 10, 30, 100, 300, 1000, and 3000 nM), or the EphA4 inhibitor KYL peptide (KYLPYWPV-LSSL, 0, 0.0003, 0.001, 0.003, 0.01, 0.03, 0.1, 0.3, 1, 3, 10, 30, 100, 300, 1000, and 3000 µM, its synthesis was outsourced to Toray Research Center) were added to each well. The ligand used was biotinylated mouse Ephrin B2-Fc chimera (R&D Systems, final concentration: 2.5 nM). After incubation at room temperature for 1 hour and subsequent washing three times, horseradish peroxidase-labeled streptavidin (GE Healthcare) was added thereto and incubated at room temperature for 1 hour. After washing three times, a TMBZ (3,3',5,5'-tetramethylbenzidine, Sigma-Aldrich) solution was added to each well and incubated at room temperature for 2 minutes. An equal amount of a reaction stopping solution (1N H$_2$SO$_4$, Wako Pure Chemical Industries) was added to each well. The absorbance at 450 nm was read using a microplate reader (Molecular Devices or PerkinElmer).

The IC$_{50}$ values of antibody A (Antibody A-IgG), antibody A-Fab, antibody A-F(ab')$_2$, and KYL peptide were 2.6 (or 3.6) nM, 438.5 nM, 2.9 nM, and 5.293 µM, respectively (FIG. 5). Antibody A and antibody A-F(ab')$_2$ had 1000 or more times the activity of the KYL peptide, and antibody A-Fab also had 10 or more times the activity of KYL peptide.

Example 7

Selectivity of Anti-EphA4 Monoclonal Antibody for Human Eph Receptor

According to the method described in Example 1, a DNA sequence encoding the signal sequence and the extracellular region of each human Eph receptor (EphA1, EphA2, EphA3, EphA4, EphA5, EphA6, EphA7, EphA8, EphA10, EphB1, EphB2, EphB3, EphB4, and EphB6) was amplified by RT-PCR using tissue-derived total RNA and cloned into a pENTR1A vector (Invitrogen/Life Technologies) having a DNA sequence encoding a human IgG1 Fc region and histidine tag. Next, the DNA sequence encoding the signal sequence and the extracellular region of each human Eph receptor, Fc, and histidine tag was transferred to a pcDNA3.1_rfcB vector through LR reaction using Gateway System (Invitrogen/Life Technologies) to construct a vector for the expression of a protein of the extracellular region of each human Eph receptor fused with the human IgG1 Fc region and the His tag (referred to as "Eph receptor extracellular region-Fc-His protein") (this vector is referred to as "Eph receptor extracellular region-Fc-His protein expression vector").

Next, HEK293EBNA cells (Life Technologies) were inoculated to a 10-cm dish (Falcon) and cultured at 37° C. for 1 day. The HEK293EBNA cells were transfected with each human Eph receptor extracellular region-Fc-His protein expression vector obtained above using TransIT-LT1 (TAKARA). After incubation (5% CO$_2$, 37° C.) for 4 days, the culture supernatant was recovered and centrifuged at 1500 rpm at room temperature for 5 minutes. The centrifugation supernatant was filtered through a 0.22-µm filter (Merck Millipore), and Hepes (Dojindo Laboratories) and sodium azide (Wako Pure Chemical Industries) were added thereto at final concentrations of 20 mM and 0.02%, respectively.

Antibody A was evaluated for its binding activity against each human Eph receptor according to the following steps.

Each well of a 96-well plate (Nunc) was coated with a donkey anti-human IgG antibody (Jackson ImmunoResearch Laboratories). After incubation overnight at 4° C., each well was blocked with 1% BlockAce (DS Pharma Biomedical) at room temperature for 1 hour. After washing with 0.05% Tween 20/PBS (Nacalai Tesque) three times, each human Eph receptor extracellular region-Fc-His protein was disseminated (final concentration: 1 nM) to each well and incubated at room temperature for 1 hour. After washing three times, a human IgG solution (100 µg/mL, Mitsubishi Pharma) and antibody A (10 µg/mL) were added to each well and incubated at room temperature for 1 hour. A horseradish peroxidase-labeled donkey anti-mouse IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well. After confirmation of moderate color development, an equal amount of a reaction stopping solution (1N $H_2SO_4$, Wako Pure Chemical Industries) was added to each well. The absorbance at 450 nm was read using a microplate reader (PerkinElmer).

Antibody A specifically had reaction activity only with human EphA4 among the members of the human Eph receptor family (FIG. 6A).

Example 8

Selectivity of Anti-EphA4 Monoclonal Antibody for Mouse Eph Receptor

According to the method described in Example 1, a DNA sequence encoding the signal sequence and the extracellular region of each mouse Eph receptor (EphA1, EphA3, EphA4, EphA5, EphA6, EphA7, EphA8, EphA10, EphB1, EphB2, EphB3, EphB4, and EphB6) was amplified by RT-PCR using tissue-derived total RNA and cloned into a pENTR1A vector (Invitrogen/Life Technologies) having a DNA sequence encoding a human IgG1 Fc region and histidine tag. Next, the DNA sequence encoding the signal sequence and the extracellular region of each mouse Eph receptor (EphA1, EphA3, EphA4, EphA5, EphA6, EphA7, EphA8, EphA10, EphB1, EphB2, EphB3, EphB4, and EphB6), Fc, and histidine tag was transferred to a pcDNA3.1_rfcB vector through LR reaction using Gateway System (Invitrogen/Life Technologies) to construct each mouse Eph receptor extracellular region-Fc-His protein expression vector. For the construction of a mouse EphA2 extracellular region-Fc-His protein expression vector, a DNA sequence encoding the signal sequence and the extracellular region of mouse EphA2 was amplified by RT-PCR using tissue-derived total RNA and cloned into a pcDNA3.1 vector having a DNA sequence encoding Fc and histidine tag to construct a mouse EphA2 extracellular region-Fc-His protein expression vector.

Next, HEK293EBNA cells (Life Technologies) were inoculated to a 10-cm dish (Falcon or BD Biosciences) and cultured at 37° C. for 1 day. The HEK293EBNA cells were transfected with the mouse EphA1, EphA2, EphA3, EphA4, EphA5, EphA6, EphA7, EphA8, EphA10, EphB1, EphB2, EphB3, EphB4, or EphB6 extracellular region-Fc-His protein expression vector obtained as described above using TransIT-LT1 (TAKARA). After incubation (5% $CO_2$, 37° C.) for 4 days, the culture supernatant was recovered and centrifuged at 1500 rpm at room temperature for 5 minutes. The centrifugation supernatant was filtered through a 0.22-μm filter (Merck Millipore), and Hepes (Dojindo Laboratories) and sodium azide (Wako Pure Chemical Industries) were added thereto at final concentrations of 20 mM and 0.02%, respectively.

Antibody A was evaluated for its binding activity against each mouse Eph receptor according to the following steps.

Each well of a 96-well plate (Nunc) was coated with a donkey anti-human IgG antibody (Jackson ImmunoResearch Laboratories). After incubation overnight at 4° C., each well was blocked with 1% BlockAce (DS Pharma Biomedical) at room temperature for 1 hour. After washing with 0.05% Tween 20/PBS (Thermo Fisher Scientific) three times, each mouse Eph receptor extracellular region-Fc-His protein was inoculated (final concentration: 1 nM) to each well and incubated at room temperature for 1 hour. After washing three times, a human IgG solution (100 μg/mL, Sigma-Aldrich) and antibody A (10 μg/mL) were added to each well and incubated at room temperature for 1 hour. A horseradish peroxidase-labeled donkey anti-mouse IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well. After confirmation of moderate color development, an equal amount of a reaction stopping solution (1N $H_2SO_4$, Wako Pure Chemical Industries) was added to each well. The absorbance at 450 nm was read using a microplate reader (PerkinElmer).

Antibody A specifically had reaction activity only with mouse EphA4 among the members of the mouse Eph receptor family (FIG. 6B).

Example 9

Reactivity of Anti-EphA4 Monoclonal Antibody with Mouse, Rat, Monkey, and Human EphA4

Mouse, rat, monkey, and human EphA4 extracellular region-Fc-His proteins were prepared according to the following steps. First, according to the method described in Example 1, a monkey EphA4 extracellular region-Fc-His protein expression vector was constructed. The amino acid sequence of monkey EphA4 used in the vector construction is shown in SEQ ID NO: 44, and its extracellular region is shown in SEQ ID NO: 45. Next, HEK293EBNA cells (Life Technologies) were inoculated to a 10-cm dish (Falcon) and cultured at 37° C. for 1 day. The HEK293EBNA cells were transfected with the monkey EphA4 extracellular region-Fc-His protein expression vector or the mouse EphA4, rat EphA4, or human EphA4 extracellular region-Fc-His protein expression vector described in Example 1 using TransIT-LT1 (TAKARA). After incubation (5% $CO_2$, 37° C.) for 4 days, the culture supernatant was recovered and centrifuged at 1500 rpm at room temperature for 5 minutes. The centrifugation supernatant was filtered through a 0.22-μm filter (Merck Millipore), and Hepes (Dojindo Laboratories) and sodium azide (Wako Pure Chemical Industries) were added thereto at final concentrations of 20 mM and 0.02%, respectively.

Antibody A was evaluated for its binding activity against various Eph receptors according to the following steps.

Each well of a 96-well plate (Nunc) was coated with a donkey anti-mouse IgG antibody (Jackson ImmunoResearch Laboratories). After incubation overnight at 4° C., each well was blocked with 1% BlockAce (Sumitomo Dainippon Pharma) at room temperature for 1 hour. After washing with 0.05% Tween 20/PBS (Nacalai Tesque) three times, the mouse, rat, monkey, or human EphA4 extracellular region-Fc-His protein was disseminated (final concentration: 1 nM) to each well and incubated at room temperature for 1 hour. After washing three times, a human IgG solution (100 μg/mL, Mitsubishi Pharma) and antibody A (0, 0.00128, 0.0064, 0.032, 0.16, 0.8, 4, and 20 μg/mL) were added to each well and incubated at room temperature for 1 hour. A horseradish peroxidase-labeled donkey anti-mouse IgG antibody (Jackson ImmunoResearch Laboratories) was added thereto and incubated at room temperature for 1 hour. After washing three times, a TMBZ (3,3',5,5'-tetramethylbenzidine, Sigma-Aldrich) solution was added to each well. After confirmation of moderate color development, an equal amount of a reaction stopping solution (1N $H_2SO_4$, Wako Pure Chemical Industries) was added to each well. The absorbance at 450 nm was read using a microplate reader (PerkinElmer).

Antibody A had equivalent reaction activity against all of mouse, rat, monkey, and human EphA4 (FIG. 7).

Example 10

Inhibitory Effect of Anti-EphA4 Monoclonal Antibody on Ligand-induced EphA4 Autophosphorylation in Hippocampal Neurons Rat hippocampal neurons were prepared according to the following steps. A fetus was removed from an 18-day pregnant rat (Charles River Laboratories Japan), and its head was incised to isolate the brain. A hippocampal region was excised under a stereoscopic microscope, then placed in a digestion solution (137 mM NaCl (Wako Pure Chemical Industries), 5 mM KCl (Wako Pure Chemical Industries), 7 mM $Na_2HPO_4$ (Wako Pure Chemical Industries), 25 mM Hepes (Dojindo Laboratories), 0.5 mg/ml DNase (Sigma-Aldrich), and 0.25% trypsin (Life Technologies)), and shaken at 37° C. for 10 minutes. The solution was removed, and 20% fetal bovine serum/Hanks buffer solution (Sigma-Aldrich) was added to the hippocampal tissues. The solution was removed, and the hippocampal tissues were washed with a Hanks buffer solution twice and then pipetted in a Hanks buffer solution to prepare a cell suspension. The cells were inoculated to a 6-well dish (Falcon) coated with poly-L-lysine containing a culture solution (Neurobasal medium (Life Technologies), 1×B-27 supplement (Life Technologies), and 0.5 mM L-glutamine (Life Technologies)).

The evaluation of EphA4 autophosphorylation inhibitory activity using the hippocampal neurons was conducted according to the following steps. The rat hippocampal neurons inoculated to a 6-well dish (Falcon) were treated with mouse Ephrin A1-Fc chimera (R&D Systems, final concentration: 10 nM), antibody A (0, 1, 10, 100, and 1000 nM) or KYL peptide (KYLPYWPVLSSL, an EphA4 inhibitor, its synthesis was outsourced to Hokkaido System Science, 0, 0.01, 0.1, 1, 10, and 100 μM,), and washed with cold-PBS (Wako Pure Chemical Industries) 45 minutes later. A lysis buffer (20 mM Tris, 150 mM NaCl, 1 mM EDTA, 1% Triton X-100 (Wako Pure Chemical Industries), 1×protease inhibitor (Nacalai Tesque), and 1×phosphatase inhibitor (Nacalai Tesque)) was added thereto to recover the cells. After mixing at 4° C. for 15 minutes, the supernatant was recovered by refrigerated centrifugation at 15000 rpm at 4° C. for 15 minutes. A rabbit anti-EphA4 polyclonal antibody (Medical & Biological Laboratories) was added to the supernatant and reacted for 90 minutes. Then, protein G beads (GE Healthcare) were added thereto and further reacted for 30 minutes. The supernatant was removed by refrigerated centrifugation at 3000 rpm at 4° C. for 1 minute, followed by the addition of 1 mL of a lysis buffer. This operation was performed three times. Then, 2×SDS sample buffer was added to each sample, which was then boiled for 10 minutes. This sample was used in SDS-PAGE and Western blotting using an anti-phosphorylated tyrosine antibody (Santa Cruz Biotechnology). Western blotting using an anti-EphA4 monoclonal antibody (Abnova) was further performed, and band intensity was quantified to calculate a value of phosphorylated EphA4/total EphA4. The anti-EphA4 monoclonal antibody (Abnova), whose immunogen is a synthetic peptide for a C-terminal region of human EphA4, is recognized as an antibody lacking neutralizing activity against human EphA4 having a N-terminal extracellular region.

Antibody A and KYL peptide (an EphA4 inhibitor) suppressed, in a concentration-dependent manner, EphA4 autophosphorylation induced by mouse EphrinA1 in the hippocampal neurons, and the $IC_{50}$ values were 24.2 nM and 9.91 μM, respectively (FIG. 8). These results demonstrated that antibody A antagonizes EphA4/ephrin signaling, as with KYL peptide, in cell systems.

Example 11

Inhibitory Effect of Anti-EphA4 Monoclonal Antibody on Ligand-induced Growth Cone Collapse in Hippocampal Neurons Rat hippocampal neurons were prepared as described in Example 10 above. The cells were inoculated to a 96-well plate (Greiner Bio-One) coated with poly-L-lysine containing culture solution.

The growth cone collapse assay using the hippocampal neurons was conducted according to the following steps. The rat hippocampal neurons of culture day 2 inoculated to the 96-well dish (Greiner Bio-One) were treated with PBS (Wako Pure Chemical Industries), antibody A (0.1, 0.3, and 1 μM), or an EphA4 inhibitor KYL peptide (KYLPYWPV-LSSL, 10, 30, and 100 μM, its synthesis was outsourced to Toray Research Center) for 15 minutes and then treated with goat anti-human Fcγ fragment IgG1 antibody (Jackson ImmunoResearch Laboratories)-preclustered mouse Ephrin A1-Fc chimera (R&D Systems, final concentration: 1 μg/mL) (ratio: 1:5) for 30 minutes. Then, the culture solution was removed, and 2% PFA (Wako Pure Chemical Industries)/4% sucrose (Wako Pure Chemical Industries)/PBS was added, and left standing for 20 minutes to fix the cells. The solution was removed, and the cells were washed with PBS three times, followed by the addition of 0.25% Triton X-100 (Wako Pure Chemical Industries)/PBS for cell penetration treatment for 15 minutes. The solution was removed, and blocked for 1 hour by the addition of 2% BSA (Sigma-Aldrich)/0.25% Triton X-100/Opti-MEM (Life technologies) and then reacted with an anti-Tau-1 antibody (Merck Millipore) and an anti-MAP-2 antibody (Merck Millipore) for 2 hours. The primary antibody solution was removed, and was washed with PBS three times and reacted with a secondary antibody and Alexa Fluor 546 Phalloidin (Molecular Probes) for 1 hour. The secondary antibody solution was removed, and was washed with PBS three times, and then were enclosed by the addition of SlowFade Gold Antifade Reagents (Molecular Probes) and observed under BIOREVO (Keyence). Neurons forming growth cone were counted in 30 fields of view per sample to calculate the proportion of the number of neurons causing growth cone collapse.

Antibody A and the EphA4 inhibitor KYL peptide suppressed, in a concentration-dependent manner, growth cone collapse induced by mouse Ephrin A1 in the hippocampal neurons (FIG. 9). Accordingly, it is shown that antibody A functionally inhibits EphA4, as with KYL peptide, in cell systems.

Example 12

Ligand aantagonistic Effect of Anti-EphA4 Monoclonal Antibody In Vivo

The in vivo competition assay using mouse newborns was conducted according to the following steps. PBS (Wako Pure Chemical Industries), antibody A, or a control antibody (mouse anti-dinitrophenol antibody) produced with a conventional procedure by immunizing rat with dinitrophenol was subcutaneously administered at a dose of 300 mg/kg (30 mL/kg) to each 8-day-old mouse (Charles River Laboratories Japan). After 24 hours, the scalp was incised under 4% isoflurane (Intervet) anesthesia, and mouse Ephrin A1-Fc chimera (300 pmol/head, R&D Systems) or PBS (Wako Pure Chemical Industries) was administered into the lateral ventricle. 1 hour thereafter, the mouse was euthanized by decapitation, followed by the extirpation of the cerebral hemisphere. The collected cerebral hemisphere was placed in a filter tube loaded in a tube for recovery of BioMasher(R) I (Nippi). After insertion of a crusher rod, the cerebral hemisphere was homogenized by refrigerated centrifugation at 15000 rpm at 4° C. for 2 minutes. The homogenate was suspended in TNE buffer (20 mM Tris, 150 mM NaCl, 1 mM EDTA, 1×protease inhibitor (Nacalai Tesque), 1×phosphatase inhibitor (Nacalai Tesque)). 3×SDS sample buffer was added to a portion of the homogenate, which was then boiled for 10 minutes, followed by protein quantification. This sample was used in SDS-PAGE and Western blotting using a donkey anti-human IgG (H+L) antibody (Jackson ImmunoResearch Laboratories), an anti-EphA4 monoclonal antibody (Abnova), and an anti-actin antibody (Sigma-Aldrich). The remaining homogenate was subjected to protein quantification and then dispensed in an amount corresponding to 3 mg of protein, and 1% Triton X-100 (Wako Pure Chemical Industries) and 0.1% SDS (Nacalai Tesque) were added thereto. After mixing at 4° C. for 15 minutes, the supernatant was recovered by refrigerated centrifugation at 15000 rpm at 4° C. for 15 minutes. 3×SDS sample buffer was added to a portion of the supernatant, which was then boiled for 10 minutes to prepare an input sample. This sample was used in SDS-PAGE and Western blotting using an anti-EphA4 monoclonal antibody (Abnova) and an anti-actin antibody (Sigma-Aldrich). A rabbit anti-EphA4 polyclonal antibody (Santa Cruz Biotechnology) was added to the remaining supernatant and reacted for 60 minutes. Then, protein G beads (GE Healthcare) were added thereto and further reacted for 30 minutes. The supernatant was removed by refrigerated centrifugation at 3000 rpm at 4° C. for 2 minutes, followed by the addition of 0.5 mL of lysis buffer (20 mM Tris, 150 mM NaCl, 1 mM EDTA, 1% Triton X-100 (Wako Pure Chemical Industries), 0.1% SDS (Nacalai Tesque), 1×protease inhibitor (Nacalai Tesque), 1×phosphatase inhibitor (Nacalai Tesque)). This operation was performed three times. Then, 1×SDS sample buffer was added to the beads, which were then boiled for 10 minutes to prepare a bead sample. This sample was used in SDS-PAGE and Western blotting using an anti-phosphorylated tyrosine antibody (Santa Cruz Biotechnology). Western blotting using an anti-EphA4 monoclonal antibody (Abnova) was further performed, and band intensity was quantified to calculate a value of phosphorylated EphA4/total EphA4. The anti-EphA4 monoclonal antibody (Abnova), whose immunogen is a synthetic peptide for a C-terminal region of human EphA4, is recognized as an antibody lacking neutralizing activity against human EphA4 having a N-terminal extracellular region.

The administration of mouse Ephrin A1 into the lateral ventricle of the mouse newborn induced EphA4 autophosphorylation in a cerebral hemisphere. Antibody A suppressed mouse EphrinA1-induced EphA4 autophosphorylation by 66% (FIG. 10). Accordingly, it is shown that antibody A also inhibits the binding between EphA4 and its ligand in vivo.

Example 13

Motor Neuron Protective Effect of Anti-EphA4 Monoclonal Antibody in In Vitro ALS Model Derived from Mouse ES Cells Mouse ES cells were maintained and cultured according to the following steps. Mouse ES cells (129×1/SvJ) cryopreserved at −80° C. were thawed in a thermostat bath and then diluted with a mouse ES cell culture medium (Knock-Out(TM) DMEM (Gibco) containing 10% fetal bovine serum (FBS, Gibco), 0.1 mM β-mercaptoethanol (Gibco), 1 mM sodium pyruvate (Invitrogen), 2 mM L-glutamine (Invitrogen), 1% nonessential amino acids (Invitrogen), 100 units/mL penicillin-100 µg/mL streptomycin (Invitrogen), and 1000 units/mL ESGRO(R) leukemia inhibitory factor (Merck Millipore)) warmed to 37° C. Each cell suspension was centrifuged (1500 rpm, 3 min, room temperature), followed by the removal of the supernatant. The cells were suspended in a fresh medium, then transferred to a culture dish with feeder cells inoculated in advance, and maintained and cultured in a $CO_2$ incubator (5% $CO_2$, 37° C.).

Astrocytes were established from a mouse newborn and maintained and cultured according to the following steps. A two-day-old wild-type mouse newborn (C57BL/6JJmsSlc (Japan SLC)) and a hybrid mouse newborn of a wild-type mouse and a variant human SOD1 (G93A) Tg-(B6.Cg-Tg (SOD1_G93A)1Gur/J (Jackson ImmunoResearch Laboratories)) mouse were each euthanized by inhalation anesthesia with isoflurane (Intervet) or decapitation. Then, the cerebral cortex was isolated from each mouse and dispersed by treatment with 0.25% trypsin-EDTA (Invitrogen) at 37° C. for 15 minutes. After the enzymatic treatment, the cells were diluted with 4 mL of Dulbecco's Modified Eagle Medium (Gibco) containing 10% FBS (Gibco) and 1% penicillin-streptomycin (Invitrogen) (10% FBS-DMEM) to terminate the enzymatic digestion. Then, impurities other than single cells were subject to filtration using a cell strainer (BD Biosciences), and the cells were centrifuged at 1500 rpm for 5 minutes. The supernatant was aspirated, diluted with 4 mL of fresh 10% FBS-DMEM, inoculated to a 60-mm culture dish on an individual basis, and cultured at 37° C. Two days after the inoculation, the medium was aspirated and replaced by the addition of 4 mL of fresh 10% FBS-DMEM. After reaching confluency, a culture supernatant containing non-adherent cells was recovered and subjected to genotyping of variant human SOD1 (G93A). 2 mL of PBS (Wako Pure Chemical Industries) was newly added to the supernatant and aspirated again. 1 mL of 0.25% trypsin-EDTA was added to the cells and incubated at 37° C. for 3 minutes. The enzymatic treatment was terminated with 3 mL of 10% FBS-DMEM, and the cells were centrifuged at 1500 rpm for 3 minutes. After the centrifugation, the medium was aspirated, and 6 mL of fresh 10% FBS-DMEM was added to the cells, which were each inoculated to a 100-mm culture dish and subcultured (passage number: 2). After reaching confluency, the medium was aspirated, and 3 mL of PBS (Wako Pure Chemical Industries) was then added to the cells and aspirated again. 2 mL of 0.25% trypsin-EDTA was added to the cells and incubated at 37° C. for 3 minutes. The enzymatic treatment was terminated with 4 mL of 10% FBS-DMEM, and the cells were centrifuged at 1500 rpm for 3 minutes. After the centrifugation, the medium was aspirated, and 12 mL of fresh 10% FBS-DMEM was added to the cells, then 6 mL of which were each inoculated to a 100-mm culture dish and subcultured (passage number: 3). The medium of the astrocytes at a passage number of 3 was aspirated, and 2 mL of PBS (Wako Pure Chemical Industries) was added to the cells and aspirated again. 2 mL of 0.25% trypsin-EDTA was added to the cells and incubated at 37° C. for 3 minutes. The enzymatic treatment was terminated by the addition of 4 mL of 10% FBS-DMEM. The suspension was recovered, centrifuged at 1500 rpm for 3 minutes, diluted with Cell banker (Nippon Zenyaku Kogyo), and cryopreserved at −80° C. until subjected to a test. When subjected to a test, each cryopreserved cell suspension was thawed in a thermostat bath and then diluted with 10% FBS-DMEM warmed to 37° C. After centrifugation (1500 rpm, 3 min, room temperature) of each cell suspension, the supernatant was removed, and the cells were suspended in a fresh medium, then inoculated to an 8-well chamber (ibidi), and maintained and cultured in a $CO_2$ incubator (5% $CO_2$, 37° C.).

The genotyping of variant human SOD1 (G93A) was conducted using REDExtract-N-Amp(TM) Tissue PCR kit (Sigma-Aldrich). In the step of maintaining and culturing the mouse ES cells, the culture supernatant containing non-adherent cells of variant human SOD1 (G93A)-expressing astrocytes recovered during the subculture was recovered into a 1.5-mL tube and centrifuged at 1500 rpm for 3 minutes. After the centrifugation, the supernatant was aspirated, and the cells were washed by the addition of 1 mL of PBS and centrifuged again, followed by the aspiration of PBS. 50 μL of an extraction solution and 12.5 μL of a tissue preparation solution were mixed and added to each sample. After mixing, the mixture was transferred to a polymerase chain reaction (PCR) tube, followed by genome extraction at a cycle of 55° C. for 10 minutes→95° C. for 3 minutes→4° C. ∞ using GeneAmp(R) PCR system 9700 (Applied Biosystems(R)). Then, the reaction solution was neutralized by the addition of 50 μL of neutralization solution B.

The extracted genome was used in genomic PCR according to the composition shown in Table 3. The primer sequences used in the PCR are shown in Table 4. Each resulting PCR product was electrophoresed on a 1% agarose gel at 100 V for 20 minutes. Samples with two bands of a 324-bp internal standard and the 236-bp variant human SOD1 (G93A) detected were identified as variant human SOD1 (G93A)-expressing astrocytes.

TABLE 3

Genomic PCR Mixture

| Reagent name | Liquid volume |
|---|---|
| Template: | 1 μL |
| Red mix: | 5 μL |
| Primer 1 (100 μmol/L): | 0.05 μL |
| Primer 2 (100 μmol/L): | 0.05 μL |
| Primer 3 (100 μmol/L): | 0.05 μL |
| Primer 4 (100 μmol/L): | 0.05 μL |
| Distilled water | 3.8 μL |
| Total: | 10 μL |

Red mix = REDExtract-N-Amp PCR reaction mix

TABLE 4

Table 4 Nucleotide sequences of primers

| Primer 1 | Variant human SOD1 (G93A) | CATCAGCCCTAATCCATCTGA |
|---|---|---|
| Primer 2 | Variant human SOD1 (G93A) | CGCGACTAACAATCAAAGTGA |
| Primer 3 | Internal standard | CTAGGCCACAGAATTGAAAGATCT |
| Primer 4 | Internal standard | GTAGGTGGAAATTCTAGCATCATCC |

The motor neuron protective effect in the in vitro ALS models was evaluated according to the following steps. The cultured and maintained mouse ES cells were treated with 0.25% trypsin/0.05% EDTA solution (Gibco) to dissociate the cells from the culture dish. The cells were recovered by centrifugation, and a suspension was then prepared and inoculated at $1.2 \times 10^5$ cells/mL to a low adsorptive 12-well plate (Nunc) (day 0). Floating culture of aggregates was performed for 2 days in a DFK medium (advanced DMEM/F-12 (Invitrogen):Neurobasal (Invitrogen) [1:1] medium containing 5% KnockOut serum replacement (Invitrogen), 2 mM L-glutamine, 100 units/mL penicillin-100 μg/mL streptomycin, and 0.1 mM β-mercaptoethanol). At day 2, the DFK medium was replaced with a DFK medium containing 1 μM retinoic acid (Sigma-Aldrich) and 2 μM purmorphamine (Stemgent). Then, medium replacement was performed at a frequency of once every two days. The differentiation into motor neurons was induced by culture for 5 days (days 3 to 7).

At day 7, the cell masses of differentiated motor neurons were dispersed in a cell dispersion solution Accumax (MS Tech) and prepared into a suspension having a cell density of $5.5 \times 10^5$ cells/mL. The suspension was inoculated at 200 μL/well to the 8-well chamber containing the mouse-derived wild-type astrocytes or the variant human SOD1 (G93A)-expressing astrocytes cultured and maintained in advance, and the resulting cocultured cells of the astrocytes and the motor neurons were used in evaluation.

The number of motor neurons observed by the coculture of the wild-type astrocytes and the motor neurons was used as a control. For the drug-treated group, the variant human SOD1 (G93A)-expressing astrocytes and the motor neurons were cocultured under a condition involving vehicle addition (IgG and 0.1% ultrapure water), antibody A (10, 30, and 100 nM), EphA4-Fc (R&D Systems, 3, 10, and 30 nM), or KYL peptide (Toray Research Center, 1, 3, and 10 μM). After culture for 2 days at 37° C. in a 5% $CO_2$ environment under each condition, the motor neurons were immunocytochemically stained with an anti-rabbit ISL1 antibody (Abcam) and Hoechst 33342 (Molecular Probes). ISL1/Hoechst 33342-copositive cells per unit area were counted as live motor neurons, and the survival rate of the motor neurons was calculated as a percentage (%) with respect to the control. FIG. 11 shows a simple schematic view showing the steps of the evaluation system.

The survival rate of the motor neurons was significantly reduced in the variant human SOD1 (G93A)-expressing astrocyte/mouse ES cell derived-motor neuron coculture (40-50%). The antibody A suppressed, in a concentration-dependent manner, mouse ES cell derived-motor neuron death induced by the variant human SOD1 (G93A)-expressing astrocytes (FIG. 12). The treatment with KYL peptide or EphA4-Fc, as with antibody A, was confirmed to have a motor neuron protective effect in this experimental system, showing that antibody A promotes the survival of mouse ES cell-derived motor neurons by inhibiting EphA4/ephrin signaling in this in vitro ALS model.

Example 14

Motor Neuron Protective Effect of Anti-EphA4 Monoclonal Antibody in In Vitro ALS Model Derived from Human iPS Cells Human iPS cells were maintained and cultured according to the following steps. Human iPS cells (201B7) cryopreserved in liquid nitrogen using Stem cell banker (TAKARA) were taken out of the gas phase of liquid nitrogen and immediately suspended and thawed in 5 mL of a human iPS cell culture medium (Essential 8, Thermo Fisher Scientific) prewarmed to 37° C. The cell suspension was recovered into a 15-mL conical tube (Falcon) and centrifuged (1000 rpm, 5 min, room temperature), followed by the removal of the supernatant. The cells were suspended in a fresh medium and then disseminated to a $\phi$60 mm cell culture dish (Falcon BD) coated with 0.5 µg/cm$^2$ Human recombinant vitronectin (Invitrogen) in advance. 10 µM Y-27632 (Wako Pure Chemical Industries) was added thereto, and the cells were maintained and cultured in a $CO_2$ incubator (5% $CO_2$, 37° C.). Medium replacement was performed every day, and the cells were subjected to the experiment when reaching confluency.

The motor neuron protective effect in the in vitro ALS models was evaluated according to the following steps. The culture medium of the maintained and cultured human iPS cells was aspirated, and the cells were washed with 2 mL of PBS (Wako Pure Chemical Industries). After aspiration of PBS, 500 µL of 0.5 mM EDTA was added to the cells, which were then incubated for 2 to 3 minutes in a $CO_2$ incubator (5% $CO_2$, 37° C.) (the cells were confirmed under a microscope every 30 seconds, and the incubation was discontinued when the intercellular association became weak). The EDTA reaction was terminated by suspension in 5 mL of a human iPS cell culture medium, and the cells were recovered into a 15-mL conical tube. The cells were centrifuged at 1000 rpm at room temperature for 5 minutes, and the supernatant was aspirated. The cell suspension containing human iPS cell masses was inoculated in an amount of approximately 1/10 per well to a low-adhesion 6-well cell culture plate (Nunclon Sphere, Nunc) and cultured in a $CO_2$ incubator (5% $CO_2$, 37° C.) using a DFK medium (advanced DMEM/F-12 (Invitrogen):Neurobasal medium (Invitrogen) [1:1] medium containing 2% B27 supplement, 5% Knock-Out serum replacement (Invitrogen), 2 mmol/L L-glutamine, 100 units/mL penicillin-100 µg/mL streptomycin, and 0.1 mmol/L β-mercaptoethanol) supplemented with 2 µM SB431542 (Sigma-Aldrich), 300 nM LDN193189 (Sigma-Aldrich), and 3 µM CHIR99021 (Sigma-Aldrich). Medium replacement was performed every 2 days by the following method. First, a human iPS cell differentiated cell aggregates (SFEBs) was recovered on a medium basis into a 15-mL conical tube and left standing at ordinary temperature for 5 minutes to precipitate the cell masses. This supernatant was aspirated, and a fresh DFK medium and 2 µM SB431542 (Sigma-Aldrich), 300 nM LDN193189 (Sigma-Aldrich, 3 µM CHIR99021 (Sigma-Aldrich) were added, and then brought back to the original well for medium replacement. At culture day 8, the SFEBs were recovered on a medium basis into a 15-mL conical tube and left standing at ordinary temperature for 5 minutes to precipitate the SFEBs. This supernatant was aspirated, and a fresh DFK medium and then 0.1 µM retinoic acid (Sigma-Aldrich) and 0.5 µM purmorphamine (Miltenyi Biotec) were added, and then brought back to the original well and cultured in a $CO_2$ incubator (5% $CO_2$, 37° C.). Medium replacement was performed every 2 days. At culture day 12, the SFEBs were recovered on a medium basis into a 15-mL conical tube and left standing at ordinary temperature for 5 minutes to precipitate the SFEBs. The supernatant was aspirated, and 500 µL of Accumax (MS TechnoSystems) was added to the cells, which were then pipetted several times and then incubated for 5 minutes in a $CO_2$ incubator (37° C., 5% $CO_2$). The cells were taken out of the incubator, suspended in 5 mL of a DFK medium, and pipetted several times to disperse the cell masses. The cell suspension was dissociated into single cells by filtration through a cell strainer (Falcon). Then, the number of cells was counted using a counting chamber. The cell suspension was recovered into another 15-mL conical tube and centrifuged at 1000 rpm at room temperature for 5 minutes. A suspension having a cell density of $5.5 \times 10^5$ cells/mL was prepared with a motor neuron culture medium (advanced DMEM/F-12 (Invitrogen):Neurobasal medium (Invitrogen) [1:1] medium containing 2% B27 Supplement, 1% horse serum, 2 mmol/L L-glutamine, 100 units/mL penicillin-100 µg/mL streptomycin, and 0.1 mmol/L β-mercaptoethanol) and inoculated at 200 µL/well to an 8-well chamber containing mouse-derived wild-type astrocytes or variant human SOD1 (G93A)-expressing astrocytes inoculated at $8 \times 10^4$ cells/well in advance. The resulting cocultured cells of the astrocytes and the motor neurons were used in evaluation (the establishment, freezing, thawing, inoculation, and maintenance and culture of the wild-type and human variant SOD1 (G93A)-expressing astrocytes were performed in the same way as in Example 13). The number of motor neurons observed by the coculture of the wild-type astrocytes and the motor neurons was used as a control. For the drug-treated group, the variant human SOD1 (G93A)-expressing astrocytes and the motor neurons were cocultured under a condition involving vehicle addition (IgG and 0.1% ultrapure water), antibody A (10, 30, and 100 nM), the EphA4 inhibitor KYL peptide (KYLPY-WPVLSSL, 1, 3, and 10 µM, its synthesis was outsourced to Toray Research Center), or EphA4-Fc (3, 10, and 30 nM, R&D systems). After culture for 2 days at 37° C. in a 5% $CO_2$ environment under each condition, the motoneurons were immunocytochemically stained with an anti-ISL1 antibody (obtained from Developmental Studies Hybridoma Bank) and Hoechst 33342 (Molecular Probes). ISL1/Hoechst 33342-copositive cells per well were counted as live motor neurons, and the survival rate of the motor neurons was calculated as % with respect to the control. FIG. 13 shows a simple schematic view showing the steps of the evaluation system.

The survival rate of the motor neurons was significantly reduced (approximately 50%) in the variant human SOD1 (G93A)-expressing astrocyte/human iPS cell-derived motor neuron coculture, as with the assay system using mouse ES cells. The antibody A suppressed, in a concentration-dependent manner, human iPS cell-derived motor neuron death induced by the variant human SOD1 (G93A)-expressing astrocytes (FIG. 14). The treatment with KYL peptide or EphA4-Fc, as with antibody A, was confirmed to have a human iPS cell-derived motor neuron protective effect in this experimental system. Accordingly, it is shown that antibody A also promotes the survival of motor neuron by inhibiting the binding between EphA4 and its ligand in human cells.

Example 15

Epitope Mapping of EphA4 Ligand-binding Domain (EphA4-LBD) by X-ray Crystallography In order to prepare a complex of antibody A-Fab prepared in Example 5 and an antigen EphA4-LBD, EphA4-LBD was prepared (Qin H. et al., J. Biol. Chem., 283: 29473-29484 (2008)). 1.33·mol (950·M, 1.4 ml) of EphA4-LBD and 0.9·mol (150·M, 6 ml) of antibody A-Fab were mixed such that EphA4-LBD had approximately 1.5 times the molar ratio of antibody A-Fab. The mixture was incubated on ice for 30 minutes. Next, the mixed solution was applied to HILOAD 26/60 Superdex 75 prep grade (GE Healthcare), followed by elution with a buffer solution for chromatography (25 mM Tris/HCl (pH 7.5), 100 mM NaCl). Fractions containing the complex were analyzed by SDS PAGE, and highly pure fractions were collected and concentrated into 34 mg/ml. This concentrate was used in crystallization.

The crystallization of the complex was performed by the sitting drop vapor diffusion method using an automatic crystallization apparatus Hydra II Plus One system (Matrix Technologies). The plate used was MRC-2 (Molecular Dimensions). The composition of a reservoir solution was 100 mM Tris/HCl (pH 7.5 to 8.5) and 30% polyethylene glycol 400. This reservoir solution and the complex solution described above were mixed at a volume ratio of 1:1 to prepare crystallization droplets. The prepared crystallization plate was left standing at 20° C.

As a result of performing crystallization under the conditions described above, crystals having a space group of P212121, lattice constant a of 70.0 angstroms, lattice constant b of 82.3 angstroms, and lattice constant c of 216.0 angstroms were obtained. Diffraction data at 2.1 angstroms was obtained by the incidence of synchrotron X-ray (1.0 angstroms) to the obtained crystals. The diffraction data was processed with HKL2000 (HKL Research Inc.), and its phase determination was performed by the molecular replacement method. The molecular replacement method employed a program PHASER (version 2.5.0, McCoy A. J. et al., J. Appl. Cryst. 40: 658-674 (2007)) contained in CCP4 Software Suite (Collaborative computational project number 4, [CCP4] version 6.5.0, Acta Cryst. D 67: 235-242 (2011)). The search models used in the molecular replacement method were the crystal structure (PDBID:3CKH) of EphA4-LBD and the crystal structure of Fab of a different antibody determined in the past by the present inventors. A molecular model appropriate for an electron density obtained from the determined phase was constructed using a program COOT (Emsley P. et al., Acta Cryst. D 60: 2126-2132 (2004)) and subjected to structure refinement using a program REFMAC (Murshudov G. N., Acta Cryst. D 53: 240-255 (1997)).

In this way, the complex crystal structure having a resolution of 2.1 angstroms was obtained by structure calculation (R=0.234, Rfree=0.288).

The obtained crystal structure of the Fab/EphA4-LBD complex was analyzed using an interaction detection tool installed in a computational chemical system MOE 2011.10 (Chemical Computing Group Inc.) to identify amino acid residues on EphA4-LBD directly interacting with Fab (FIG. 15). Standard settings of MOE were used as detection protocol. The identified amino acid residues were Ser58, Met60, Gln71, Val72, Cys73, Thr104, Arg106, Gln156, Asp161, Arg162, Ile163, Cys191, and Ile192. FIG. 16 shows the surface structure of EphA4-LBD prepared using Maestro (version 10.6, Schrodinger). As a result, the present inventors concluded that regions having these amino acid residues are Fab-binding regions of EphA4-LBD.

Example 16

Preparation of Humanized Antibody of Antibody A

Preparation of Humanized Anti-Human EphA4 Antibody

Variable regions of each humanized antibody were designed. On the basis of high homology to the framework regions (FRs) of antibody A, human antibody light chain FRs IGKV1-NL1*01 (SEQ ID NO: 50) or IGKV3D-15*01 (SEQ ID NO: 51) and JK1 (SEQ ID NO: 52) and heavy chain FRs IGHV7-4-1*02 (SEQ ID NO: 53) and JH6 (SEQ ID NO: 54) were selected as humanized antibody FRs. Then, FR amino acids interacting with CDR amino acids were predicted using the 3D structural prediction model of mouse antibody A and used in grafting with CDRs (SEQ ID NOs: 26 to 30, and 31 to 33). In light of the enhancement of EphA4 phosphorylation and the ADCC activity, a human IgG$_2$ heavy chain constant region (SEQ ID NO: 62) which had C131S, C219S, V234A, and G237A mutations and lacked a C-terminal lysine residue, or a heavy chain constant region (SEQ ID NO: 60) which contained human IgG$_1$-derived CH1 and hinge region and human IgG$_2$-derived CH2 and CH3 having V234A and G237A mutations and lacking a C-terminal lysine residue, was used as a heavy chain constant region. Human Igκ light chain constant region (SEQ ID NO: 64) was used as a light chain constant region. HK1 (SEQ ID NO: 72), HK2 (SEQ ID NO: 74), and HK4 (SEQ ID NO: 76) were designed as humanized antibody heavy chain variable regions carrying grafted CDRs (SEQ ID NOs: 26, 28, and 30) determined by the Kabat definition method. HA1 (SEQ ID NO: 66), HA2 (SEQ ID NO: 68), and HA4 (SEQ ID NO: 70) were designed as humanized antibody heavy chain variable regions carrying grafted CDRs (SEQ ID NOs: 27, 29, and 30) determined by the AbM definition method. L1-4 (SEQ ID NO: 78), L1-5 (SEQ ID NO: 80), and L1-6 (SEQ ID NO: 82) were designed as humanized antibody light chain variable regions using IGKV1-NL1*01 and JK1. L2-4 (SEQ ID NO: 84) was designed as a humanized antibody light chain variable region using IGKV3D-15*01 and JK1. Incidentally, in the design of the heavy chain constant regions, EphA4 phosphorylation was confirmed in the same way as that described in Example 10.

A gene sequence encoding the amino acid sequence of HK1, HK2, or HK4 was synthesized by converting the amino acid sequence of heavy chain CDRs (SEQ ID NOs: 26, 28, and 30) of antibody A grafted in IGHV7-4-1*02 (SEQ ID NO: 53) and JH6 (SEQ ID NO: 54) with a signal sequence (SEQ ID NO: 55) further added to the N terminus, to a gene sequence by GenScript USA Inc., and prepared by PCR mutagenesis (HK1: SEQ ID NO: 73, HK2: SEQ ID NO: 75, HK4: SEQ ID NO: 77, signal sequence: SEQ ID NO: 57). A gene sequence encoding the amino acid sequence of HA1, HA2, or HA4 was synthesized by converting the amino acid sequence of heavy chain CDRs (SEQ ID NOs: 27, 29, and 30) of antibody A grafted in IGHV7-4-1*02 (SEQ ID NO: 53) and JH6 (SEQ ID NO: 54) with a signal sequence (SEQ ID NO: 55) further added to the N terminus, to a gene sequence by GenScript USA Inc., and prepared by PCR mutagenesis (HA1: SEQ ID NO: 67, HA2: SEQ ID NO: 69, HA4: SEQ ID NO: 71, signal sequence: SEQ ID NO: 56). The genes encoding these humanized heavy chain variable regions and signal sequences were inserted to expression vectors (pcDNA3.4) containing a gene sequence (SEQ ID NO: 63) encoding the human IgG$_2$ constant region (SEQ ID NO: 62) which had C131S, C219S, V234A, and G237A mutations and lacked a C-terminal lysine residue, or expression vectors (pcDNA3.4) containing a gene sequence (SEQ ID NO: 61) encoding the constant region (SEQ ID NO: 60) which contained human IgG$_1$-derived CH1 and hinge and human IgG$_2$-derived CH2 and CH3 having V234A and G237A mutations. A gene sequence encoding the amino acid sequence of L1-4, L1-5, or L1-6 was synthesized by converting the amino acid sequence of light chain CDRs (SEQ ID NOs: 31 to 33) of antibody A grafted in IGKV1-NL1*01 (SEQ ID NO: 50) and JK1 (SEQ ID NO: 52) with a signal sequence (SEQ ID NO: 58) further added to the N terminus, to a gene sequence by GenScript USA Inc., and prepared by PCR mutagenesis (L1-4: SEQ ID NO: 79, L1-5: SEQ ID NO: 81, L1-6: SEQ ID NO: 83, signal sequence: SEQ ID NO: 59). A gene sequence encoding the amino acid sequence of L2-4 was synthesized by converting the amino acid sequence of light chain CDRs (SEQ ID NOs: 31 to 33) of antibody A grafted in IGKV3D-15*01 (SEQ ID NO: 51) and JK1 (SEQ ID NO: 52) with a signal sequence (SEQ ID NO: 58) further added to the N-terminus, to a gene sequence by GenScript USA Inc., and prepared by PCR mutagenesis (L2-4: SEQ ID NO: 85, signal sequence: SEQ ID NO: 59). The genes encoding these humanized light chain variable regions and signal sequences were inserted to expression vectors (pcDNA3.4) containing a gene sequence (SEQ ID NO: 65) encoding the human Igκ constant region (SEQ ID NO: 64). In this context, the term "C131S" refers to a mutation that substitutes cysteine at Eu numbering position 131 with serine. The term "C219S" refers to a mutation that substitutes cysteine at Eu numbering position 219 with serine. The term "V234A" refers to a mutation that substitutes valine at Eu numbering position 234 with alanine. The term "G237A" refers to a mutation that substitutes glycine at Eu numbering position 237 with alanine. In this context, the CH1 refers to a region from Eu numbering positions 118 to 215 in the human IgG constant region. The hinge refers to a region from Eu numbering positions 216 to 230 in the human IgG constant region. The CH2 refers to a region from Eu numbering positions 231 to 340 in the human IgG constant region. The CH3 refers to a region from Eu numbering positions 341 to 446 in the human IgG constant region. In order to produce these humanized antibodies, the expression vectors described above were used in combination as shown in Table 5 using Expi293 expression system (Gibco/Thermo Fisher Scientific) to transfect Expi293F cells (Gibco/Thermo Fisher Scientific). Each supernatant was recovered and purified using protein A (GE Healthcare).

TABLE 5

| Humanized antibody No. | L chain | | | H chain | | | | |
| | Variable region | | | Variable region | | | Constant region | |
| | Name | Amino acid sequence (SEQ ID NO) | Nucleic acid sequence (SEQ ID NO) | Name | Amino acid sequence (SEQ ID NO) | Nucleic acid sequence (SEQ ID NO) | Amino acid sequence (SEQ ID NO) | Nucleic acid sequence (SEQ ID NO) |
|---|---|---|---|---|---|---|---|---|
| 75 | L1-4 | 78 | 79 | HA1 | 66 | 67 | 60 | 61 |
| 76 | L1-4 | 78 | 79 | HA2 | 68 | 69 | | |
| 67 | L1-4 | 78 | 79 | HA4 | 70 | 71 | | |
| 77 | L1-4 | 78 | 79 | HK1 | 72 | 73 | | |
| 78 | L1-4 | 78 | 79 | HK2 | 74 | 75 | | |
| 69 | L1-4 | 78 | 79 | HK4 | 76 | 77 | | |
| 81 | L1-5 | 80 | 81 | HA1 | 66 | 67 | | |
| 82 | L1-5 | 80 | 81 | HA2 | 68 | 69 | | |
| 83 | L1-5 | 80 | 81 | HA4 | 70 | 71 | | |
| 84 | L1-5 | 80 | 81 | HK1 | 72 | 73 | | |
| 85 | L1-5 | 80 | 81 | HK2 | 74 | 75 | | |
| 86 | L1-5 | 80 | 81 | HK4 | 76 | 77 | | |
| 87 | L1-6 | 82 | 83 | HA1 | 66 | 67 | | |
| 88 | L1-6 | 82 | 83 | HA2 | 68 | 69 | | |
| 89 | L1-6 | 82 | 83 | HA4 | 70 | 71 | | |
| 90 | L1-6 | 82 | 83 | HK1 | 72 | 73 | | |
| 91 | L1-6 | 82 | 83 | HK2 | 74 | 75 | | |
| 92 | L1-6 | 82 | 83 | HK4 | 76 | 77 | | |
| 93 | L2-4 | 84 | 85 | HA1 | 66 | 67 | | |
| 94 | L2-4 | 84 | 85 | HA2 | 68 | 69 | | |
| 71 | L2-4 | 84 | 85 | HA4 | 70 | 71 | | |
| 95 | L2-4 | 84 | 85 | HK1 | 72 | 73 | | |
| 96 | L2-4 | 84 | 85 | HK2 | 74 | 75 | | |
| 73 | L2-4 | 84 | 85 | HK4 | 76 | 77 | | |
| 139 | L1-4 | 78 | 79 | HA1 | 66 | 67 | 62 | 63 |
| 140 | L1-4 | 78 | 79 | HA2 | 68 | 69 | | |
| 138 | L1-4 | 78 | 79 | HA4 | 70 | 71 | | |
| 141 | L1-4 | 78 | 79 | HK1 | 72 | 73 | | |
| 142 | L1-4 | 78 | 79 | HK2 | 74 | 75 | | |
| 143 | L1-4 | 78 | 79 | HK4 | 76 | 77 | | |
| 152 | L1-5 | 80 | 81 | HA1 | 66 | 67 | | |
| 153 | L1-5 | 80 | 81 | HA2 | 68 | 69 | | |
| 151 | L1-5 | 80 | 81 | HA4 | 70 | 71 | | |
| 154 | L1-5 | 80 | 81 | HK1 | 72 | 73 | | |
| 145 | L1-5 | 80 | 81 | HK2 | 74 | 75 | | |
| 155 | L1-5 | 80 | 81 | HK4 | 76 | 77 | | |
| 157 | L1-6 | 82 | 83 | HA1 | 66 | 67 | | |
| 158 | L1-6 | 82 | 83 | HA2 | 68 | 69 | | |
| 156 | L1-6 | 82 | 83 | HA4 | 70 | 71 | | |
| 144 | L1-6 | 82 | 83 | HK1 | 72 | 73 | | |
| 159 | L1-6 | 82 | 83 | HK2 | 74 | 75 | | |
| 160 | L1-6 | 82 | 83 | HK4 | 76 | 77 | | |
| 133 | L2-4 | 84 | 85 | HA1 | 66 | 67 | | |
| 134 | L2-4 | 84 | 85 | HA2 | 68 | 69 | | |
| 132 | L2-4 | 84 | 85 | HA4 | 70 | 71 | | |
| 135 | L2-4 | 84 | 85 | HK1 | 72 | 73 | | |

TABLE 5-continued

| Humanized antibody No. | L chain | | | H chain | | | | |
|---|---|---|---|---|---|---|---|---|
| | | Variable region | | | Variable region | | Constant region | |
| | Name | Amino acid sequence (SEQ ID NO) | Nucleic acid sequence (SEQ ID NO) | Name | Amino acid sequence (SEQ ID NO) | Nucleic acid sequence (SEQ ID NO) | Amino acid sequence (SEQ ID NO) | Nucleic acid sequence (SEQ ID NO) |
| 136 | L2-4 | 84 | 85 | HK2 | 74 | 75 | | |
| 137 | L2-4 | 84 | 85 | HK4 | 76 | 77 | | |

Example 17

Affinity of Anti-EphA4 Monoclonal Humanized Antibody for Human EphA4

The binding affinity of each anti-EphA4 monoclonal humanized antibody obtained in Example 16 for human EphA4 was determined by surface plasmon resonance (SPR) using Biacore T200 (GE Healthcare). First, for the assay of antibody A, a rat anti-mouse $IgG_1$ antibody produced with a conventional method by immunizing rat with mouse $IgG_1$ antibody was immobilized on sensor chip CM5. The immobilization of the rat anti-mouse IgG1 antibody on sensor chip CM5 was performed by the amine coupling method using N-hydroxysuccinimide (NHS) and N-ethyl-N'-(3-dimethylaminopropyl)carbodiimide hydrochloride (EDC). Ethanolamine was used in blocking (the sensor chip and the reagents for immobilization were all manufactured by GE Healthcare). The antibody was diluted with a buffer solution for immobilization (10 mM sodium acetate, pH 4.5) and immobilized on the sensor chip according to the protocol attached to Biacore T200. For the assay of each humanized monoclonal antibody, a protein A chip (GE Healthcare, 29-1383-03) was used. Antibody A or the humanized monoclonal antibody was diluted with a running buffer solution HBS-EP (GE Healthcare), injected onto only flow cell 2 for 120 seconds, and captured (captured amount: approximately 30 to 60 RU). Subsequently, human EphA4 extracellular region-SEAP-His protein serially diluted in the range of 50, 16.7, 5.6, 1.9, and 0.6 nM using HBS-EP was sequentially added from the lower toward higher concentration sides without regeneration operation. Binding reaction curves were sequentially observed at the time of the addition (association phase, for 120 sec) and after the completion of the addition (dissociation phase, for 900 sec). After the completion of each observation, the sensor chip was regenerated by the addition of 3 M $MgCl_2$ (for 60 sec) or 10 mM Glycine-HCl pH 1.5 (for 30 sec). The obtained binding reaction curves were subjected to fitting analysis with 1:1 binding models using software BIA evaluation attached to the system to calculate the affinity (KD=kd/ka) for human EphA4 (Table 6).

All of the humanized antibodies described in Table 5 were found to exhibit affinity substantially equivalent to their parent antibody A (Table 6).

TABLE 6

| humanized antibody No. | $k_a$ 1/Ms | kd 1/s | KD M | Rmax1 RU | $Chi^2$ $RU^2$ |
|---|---|---|---|---|---|
| 75 | 3.8E+05 | 4.2E−04 | 1.2E−09 | 29 | 0.17 |
| 76 | 3.3E+05 | 3.4E−04 | 1.0E−09 | 29 | 0.18 |
| 67 | 3.3E+05 | 3.5E−04 | 1.1E−09 | 28 | 0.15 |
| 77 | 4.1E+05 | 5.8E−04 | 1.4E−09 | 27 | 0.20 |
| 78 | 3.4E+05 | 3.9E−04 | 1.1E−09 | 30 | 0.17 |
| 69 | 3.4E+05 | 3.7E−04 | 1.1E−09 | 29 | 0.19 |
| 81 | 3.4E+05 | 5.4E−04 | 1.6E−09 | 24 | 0.12 |
| 82 | 2.9E+05 | 4.6E−04 | 1.6E−09 | 24 | 0.10 |
| 83 | 2.9E+05 | 5.4E−04 | 1.9E−09 | 20 | 0.06 |
| 84 | 3.5E+05 | 5.6E−04 | 1.7E−09 | 25 | 0.13 |
| 85 | 3.1E+05 | 5.0E−04 | 1.6E−09 | 26 | 0.12 |
| 86 | 3.1E+05 | 4.6E−04 | 1.5E−09 | 26 | 0.13 |
| 87 | 3.5E+05 | 5.1E−04 | 1.5E−09 | 27 | 0.12 |
| 88 | 3.0E+05 | 4.2E−04 | 1.4E−09 | 26 | 0.13 |
| 89 | 3.1E+05 | 4.1E−04 | 1.3E−09 | 24 | 0.13 |
| 90 | 3.6E+05 | 5.5E−04 | 1.5E−09 | 27 | 0.14 |
| 91 | 3.3E+05 | 4.4E−04 | 1.3E−09 | 25 | 0.13 |
| 92 | 3.3E+05 | 4.3E−04 | 1.3E−09 | 27 | 0.16 |
| 93 | 3.1E+05 | 2.4E−04 | 7.7E−10 | 24 | 0.10 |
| 94 | 2.6E+05 | 2.4E−04 | 9.5E−10 | 25 | 0.08 |
| 71 | 2.8E+05 | 2.3E−04 | 8.2E−10 | 25 | 0.09 |
| 95 | 3.0E+05 | 3.1E−04 | 1.0E−09 | 27 | 0.08 |
| 96 | 2.7E+05 | 3.1E−04 | 1.1E−09 | 28 | 0.07 |
| 73 | 2.9E+05 | 2.7E−04 | 9.3E−10 | 27 | 0.09 |
| 139 | 3.7E+05 | 5.3E−04 | 1.4E−09 | 29 | 0.15 |
| 140 | 3.2E+05 | 4.3E−04 | 1.4E−09 | 29 | 0.12 |
| 138 | 3.3E+05 | 4.3E−04 | 1.3E−09 | 29 | 0.12 |
| 141 | 3.9E+05 | 6.2E−04 | 1.6E−09 | 26 | 0.14 |
| 142 | 3.4E+05 | 5.0E−04 | 1.5E−09 | 28 | 0.12 |
| 143 | 3.5E+05 | 5.1E−04 | 1.5E−09 | 26 | 0.12 |
| 152 | 4.0E+05 | 8.2E−04 | 2.0E−09 | 23 | 0.09 |
| 153 | 2.9E+05 | 6.0E−04 | 2.1E−09 | 24 | 0.07 |
| 151 | 3.2E+05 | 5.3E−04 | 1.7E−09 | 28 | 0.13 |
| 154 | 3.9E+05 | 6.5E−04 | 2.2E−09 | 24 | 0.10 |
| 145 | 3.3E+05 | 6.5E−04 | 2.0E−09 | 27 | 0.11 |
| 155 | 3.3E+05 | 6.4E−04 | 1.9E−09 | 27 | 0.11 |
| 157 | 3.5E+05 | 6.8E−04 | 2.0E−09 | 24 | 0.09 |
| 158 | 3.1E+05 | 6.1E−04 | 1.9E−09 | 24 | 0.06 |
| 158 | 3.1E+05 | 5.6E−04 | 1.6E−09 | 24 | 0.08 |
| 144 | 4.0E+05 | 7.8E−04 | 2.0E−09 | 23 | 0.09 |
| 159 | 3.1E+05 | 6.1E−04 | 2.0E−09 | 22 | 0.07 |
| 160 | 3.2E+05 | 6.1E−04 | 1.9E−09 | 25 | 0.06 |
| 133 | 3.0E+05 | 3.2E−04 | 1.1E−09 | 26 | 0.07 |
| 134 | 2.8E+05 | 3.2E−04 | 1.2E−09 | 24 | 0.06 |
| 132 | 2.7E+05 | 3.1E−04 | 1.2E−09 | 26 | 0.08 |
| 135 | 3.2E+05 | 4.0E−04 | 1.3E−09 | 26 | 0.08 |
| 138 | 2.9E+05 | 3.9E−04 | 1.4E−09 | 25 | 0.07 |
| 137 | 2.9E+05 | 3.9E−04 | 1.3E−09 | 27 | 0.09 |
| antibody A | 4.2E+05 | 2.5E−04 | 6.0E−10 | 37 | 0.19 |

Example 18

Human EphA4-human Ligand Binding Inhibitory Activity of Anti-EphA4 Monoclonal Humanized Antibody Each anti-EphA4 monoclonal humanized antibody obtained in Example 16 was evaluated for its inhibitory activity against the binding between human EphA4 and its human ligand according to the following steps. Each well of a 96-well plate (Nunc) was coated with an anti-alkaline phosphatase antibody (Thermo Fisher Scientific). After incubation overnight at 4° C., each well was blocked with 1% BlockAce (DS Pharma Biomedical) at room temperature for 1 hour. After washing with 0.05% Tween 20/PBS (Thermo Fisher Scientific) three times, the human EphA4 extracellular region-SEAP-His protein obtained by the method of Example 2 was added (final concentration: 10 nM) to each well and incubated at room temperature for 1 hour. After washing three times, a ligand and each serially diluted humanized antibody of antibody A (0, 0.003, 0.01, 0.03, 0.1, 0.3, 1, 3, 10, 30, 100, 300, 1000, and 3000 nM) were added to each well. The ligand used was biotinylated human Ephrin A5-Fc chimera (R&D Systems, final concentration: 0.7 nM). After incubation at room temperature for 1 hour and subsequent washing three times, horseradish peroxidase-labeled streptavidin (GE Healthcare) was added thereto and incubated at room temperature for 1 hour. After washing three times, a TMBZ (3,3',5,5'-tetramethylbenzidine, Sigma-Aldrich) solution was added to each well and incubated at room temperature for 2 minutes. An equal amount of a reaction stopping solution (1N $H_2SO_4$, Wako Pure Chemical Industries) was added to each well. The absorbance at 450 nm was read using a microplate reader (PerkinElmer).

All of the humanized antibodies described in Table 5 were found to exhibit inhibitory activity substantially equivalent to their parent antibody A (Table 7).

TABLE 7

| humanized antibody No. | IC50 nM |
|---|---|
| 75 | 2.9 |
| 76 | 2.9 |
| 67 | 4.4 |
| 77 | 3.5 |
| 78 | 2.8 |
| 69 | 3.1 |
| 81 | 4.0 |
| 82 | 4.1 |
| 83 | 3.7 |
| 84 | 4.6 |
| 85 | 4.0 |
| 86 | 4.0 |
| 87 | 3.0 |
| 88 | 3.6 |
| 89 | 4.3 |
| 90 | 4.5 |
| 91 | 4.9 |
| 92 | 3.5 |
| 93 | 2.5 |
| 94 | 2.7 |
| 71 | 2.5 |
| 95 | 3.1 |
| 96 | 3.7 |
| 73 | 2.4 |
| 139 | 3.3 |
| 140 | 2.4 |
| 138 | 2.9 |
| 141 | 3.0 |
| 142 | 3.7 |
| 143 | 5.3 |
| 152 | 2.0 |
| 153 | 2.3 |
| 151 | 2.0 |
| 154 | 2.5 |
| 145 | 3.7 |
| 155 | 2.4 |
| 157 | 2.6 |
| 158 | 2.8 |
| 156 | 2.5 |
| 144 | 3.6 |
| 159 | 2.6 |
| 160 | 2.2 |
| 133 | 3.0 |
| 134 | 3.0 |
| 132 | 3.1 |
| 135 | 2.5 |
| 136 | 2.5 |
| 137 | 2.5 |

Example 19

Selectivity of Anti-EphA4 Monoclonal Humanized Antibody for Human Eph Receptor

According to the method described in Example 7, a DNA sequence encoding the signal sequence and the extracellular region of each human Eph receptor (EphA1, EphA2, EphA3, EphA4, EphA5, EphA6, EphA7, EphA8, EphA10, EphB1, EphB2, EphB3, EphB4, and EphB6) was amplified by RT-PCR using tissue-derived total RNA and cloned into a pENTR1A vector (Invitrogen/Life Technologies) having a DNA sequence encoding SEAP protein and histidine tag. Next, the DNA sequence encoding the signal sequence and the extracellular region of each human Eph receptor, SEAP protein, and histidine tag was transferred to a pcDNA3.1_rfcB vector through LR reaction using Gateway System (Invitrogen/Life Technologies) to construct a vector for the expression of a protein of the extracellular region of each human Eph receptor fused with the SEAP protein and the His tag (referred to as "Eph receptor extracellular region-SEAP-His protein") (this vector is referred to as "Eph receptor extracellular region-SEAP-His protein expression vector").

Next, each human Eph receptor extracellular region-SEAP-His protein expression vector was transferred to Expi293F cells (Gibco/Thermo Fisher Scientific) using Expi293 expression system (Gibco/Thermo Fisher Scientific). After incubation (5% $CO_2$, 37° C.) for 5 days, the culture supernatant was recovered and centrifuged at 1500 rpm at room temperature for 5 minutes. The centrifugation supernatant was filtered through a 0.45-μm filter (Merck Millipore).

Each anti-EphA4 monoclonal humanized antibody obtained in Example 16 was evaluated for its binding activity against each human Eph receptor according to the following steps.

Each well of a 96-well plate (Nunc) was coated with a rabbit anti-6-His antibody (Bethyl Laboratories). Each well was blocked at room temperature for 1 hour and then incubated overnight with 1% BlockAce (DS Pharma Biomedical) at 4° C. After washing with 0.05% Tween 20/PBS (Nacalai Tesque) three times, the SEAP-His protein of human EphA1, EphA2, EphA3, EphA4, EphA5, EphA6, EphA7, EphA8, EphA10, EphB1, EphB2, EphB3, EphB4, or EphB6 was added (final concentration: 1 nM) to each well and incubated at room temperature for 1 hour. After washing three times, the humanized antibody was added to each well and incubated at room temperature for 1 hour. After washing three times, a horseradish peroxidase-labeled donkey anti-mouse IgG antibody (Jackson ImmunoResearch Laboratories) was added thereto and incubated at room temperature for 1 hour. After washing three times, TMB Microwell Peroxidase Substrate System (Kirkegaard & Perry Laboratories (KPL)) was added to each well. After confirmation of moderate color development, an equal amount of a reaction stopping solution (1N $H_2SO_4$, Wako Pure Chemical Industries) was added to each well. The absorbance at 450 nm was read using a microplate reader (Thermo Fisher Scientific).

The percentages with respect to the absorbance at 450 nm for human EphA4 (hEphA4-SEAP-His) as 100% were summarized in Table 8. As a result, all of the humanized antibodies described in Table 5 were found to specifically bind to human EphA4, as with their parent antibody A (Table 8).

TABLE 8

| humanized antibody | SEAP-His | hEphA1-SEAP- | hEphA2-SEAP- | hEphA3-SEAP- | hEphA4-SEAP- | hEphA5-SEAP- | hEphA6-SEAP- | hEphA7-SEAP- | hEphA8-SEAP- | hEphA10-SEAP- | hEphB1-SEAP- | hEphB2-SEAP- | hEphB3-SEAP- | hEphB4-SEAP- | hEphB6-SEAP- |
|---|---|---|---|---|---|---|---|---|---|---|---|---|---|---|---|
| 75 | 4.4 | 4.7 | 4.6 | 4.8 | 100 | 4.7 | 8.3 | 4.7 | 4.8 | 4.4 | 4.4 | 4.5 | 4.7 | 4.6 | 4.7 |
| 76 | 5.5 | 5.1 | 4.8 | 4.9 | 100 | 5.3 | 7.9 | 4.8 | 5.5 | 4.7 | 4.9 | 4.9 | 5.0 | 5.2 | 5.2 |
| 67 | 5.0 | 4.6 | 4.6 | 4.8 | 100 | 4.8 | 7.3 | 4.7 | 4.7 | 4.6 | 4.6 | 4.7 | 4.9 | 4.9 | 4.7 |
| 77 | 4.7 | 4.5 | 4.5 | 4.5 | 100 | 4.4 | 6.0 | 4.3 | 4.8 | 4.5 | 4.6 | 4.5 | 4.6 | 4.5 | 4.5 |
| 78 | 5.3 | 6.6 | 4.9 | 5.1 | 100 | 5.1 | 10.0 | 5.0 | 5.4 | 5.2 | 5.0 | 5.1 | 5.2 | 5.1 | 5.2 |
| 69 | 6.1 | 5.7 | 5.5 | 5.4 | 100 | 5.6 | 9.5 | 5.3 | 5.5 | 5.4 | 5.6 | 5.5 | 5.9 | 5.5 | 5.6 |
| 50 | 5.0 | 4.4 | 4.8 | 5.0 | 100 | 4.9 | 8.8 | 5.2 | 5.2 | 4.8 | 4.9 | 5.0 | 4.9 | 5.0 | 5.0 |
| 81 | 5.9 | 5.4 | 5.4 | 5.4 | 100 | 6.5 | 8.7 | 5.4 | 5.8 | 5.6 | 5.4 | 5.6 | 5.6 | 5.7 | 5.5 |
| 82 | 6.5 | 5.7 | 5.8 | 5.7 | 100 | 5.8 | 7.5 | 5.5 | 6.0 | 5.4 | 5.6 | 5.6 | 5.7 | 5.7 | 5.8 |
| 83 | 5.1 | 5.2 | 4.9 | 4.9 | 100 | 5.0 | 6.0 | 4.8 | 5.3 | 5.1 | 5.2 | 5.1 | 4.8 | 5.4 | 4.9 |
| 84 | 5.3 | 5.0 | 5.1 | 5.1 | 100 | 5.0 | 6.2 | 4.8 | 5.5 | 5.0 | 5.0 | 4.9 | 5.2 | 5.2 | 5.2 |
| 85 | 6.1 | 5.9 | 5.7 | 5.8 | 100 | 5.7 | 8.6 | 5.6 | 5.7 | 5.6 | 5.7 | 5.7 | 5.9 | 5.8 | 5.7 |
| 86 | 5.5 | 5.3 | 5.4 | 5.5 | 100 | 5.4 | 6.4 | 5.3 | 5.7 | 5.2 | 5.3 | 5.4 | 5.5 | 5.5 | 5.3 |
| 87 | 6.1 | 5.8 | 5.8 | 6.0 | 100 | 5.9 | 7.5 | 6.0 | 6.2 | 5.8 | 6.1 | 6.0 | 6.3 | 6.1 | 6.1 |
| 88 | 5.8 | 5.5 | 5.6 | 5.8 | 100 | 5.8 | 8.4 | 5.4 | 5.7 | 5.7 | 5.7 | 5.7 | 5.7 | 5.8 | 4.8 |
| 89 | 5.2 | 5.1 | 5.2 | 5.2 | 100 | 5.1 | 7.6 | 4.9 | 5.4 | 5.1 | 4.9 | 5.9 | 5.1 | 5.0 | 5.2 |
| 90 | 5.2 | 5.8 | 6.1 | 6.6 | 100 | 6.4 | 8.8 | 5.6 | 6.2 | 8.5 | 6.6 | 7.0 | 7.0 | 6.2 | 6.3 |
| 91 | 6.4 | 5.8 | 6.9 | 6.5 | 100 | 6.8 | 9.6 | 6.4 | 6.7 | 6.6 | 6.9 | 6.6 | 6.9 | 6.6 | 6.5 |
| 92 | 6.5 | 7.0 | 5.0 | 5.1 | 100 | 4.9 | 7.1 | 4.9 | 5.0 | 4.9 | 5.0 | 5.0 | 5.1 | 5.0 | 4.9 |
| 93 | 5.0 | 5.0 | 6.4 | 6.8 | 100 | 6.5 | 8.6 | 6.1 | 7.0 | 6.4 | 6.7 | 7.0 | 6.7 | 6.5 | 6.4 |
| 94 | 6.7 | 6.5 | 5.7 | 5.6 | 100 | 5.6 | 9.2 | 5.2 | 5.3 | 5.3 | 5.4 | 5.5 | 5.5 | 5.5 | 5.3 |
| 71 | 5.6 | 5.6 | 4.2 | 4.8 | 100 | 4.6 | 7.0 | 4.4 | 4.4 | 4.5 | 4.6 | 4.7 | 4.6 | 4.6 | 4.7 |
| 95 | 4.4 | 4.5 | 5.3 | 5.5 | 100 | 6.0 | 9.8 | 5.3 | 5.4 | 5.3 | 5.6 | 5.5 | 5.6 | 5.5 | 5.5 |
| 96 | 5.5 | 5.6 | 5.6 | 5.8 | 100 | 6.0 | 7.4 | 5.6 | 5.8 | 5.6 | 5.7 | 5.6 | 5.8 | 5.7 | 5.6 |
| 73 | 5.8 | 6.0 | 5.7 | 5.9 | 100 | 5.7 | 10.0 | 5.5 | 6.0 | 5.5 | 5.5 | 5.9 | 5.6 | 5.7 | 5.9 |
| 139 | 5.7 | 5.7 | 5.9 | 5.5 | 100 | 5.4 | 10.8 | 5.2 | 5.4 | 5.2 | 5.1 | 5.3 | 5.4 | 5.2 | 5.0 |
| 140 | 5.4 | 5.2 | 5.3 | 4.9 | 100 | 5.1 | 10.2 | 4.9 | 5.4 | 5.0 | 5.4 | 5.2 | 5.1 | 5.4 | 5.4 |
| 138 | 5.1 | 5.2 | 5.0 | 5.3 | 100 | 5.3 | 8.1 | 5.3 | 5.5 | 5.2 | 5.4 | 5.2 | 5.2 | 5.2 | 5.6 |
| 141 | 5.0 | 5.3 | 5.2 | 5.5 | 100 | 5.7 | 7.6 | 5.5 | 5.7 | 5.4 | 5.6 | 5.6 | 5.6 | 5.4 | 5.6 |
| 142 | 5.8 | 5.6 | 5.6 | 5.5 | 100 | 5.7 | 9.7 | 5.2 | 6.0 | 5.2 | 5.9 | 5.8 | 5.9 | 5.7 | 5.9 |
| 143 | 6.3 | 6.0 | 5.7 | 5.6 | 100 | 6.1 | 9.9 | 5.8 | 5.4 | 5.8 | 5.9 | 5.8 | 5.9 | 5.9 | 5.0 |
| 152 | 5.4 | 5.8 | 5.4 | 5.8 | 100 | 5.8 | 8.3 | 5.7 | 6.0 | 5.8 | 6.0 | 5.9 | 6.0 | 6.0 | 5.4 |
| 153 | 5.9 | 6.3 | 6.0 | 6.1 | 100 | 6.1 | 8.7 | 6.2 | 6.1 | 6.0 | 6.8 | 7.0 | 7.3 | 7.4 | 6.2 |
| 151 | 6.8 | 7.1 | 6.9 | 6.9 | 100 | 7.0 | 9.9 | 6.8 | 6.9 | 6.6 | 6.3 | 6.2 | 6.2 | 6.4 | 7.1 |
| 154 | 6.3 | 6.4 | 6.2 | 6.2 | 100 | 6.3 | 8.4 | 6.3 | 5.5 | 5.9 | 6.5 | 6.7 | 6.7 | 6.7 | 6.4 |
| 145 | 6.4 | 6.7 | 6.5 | 6.6 | 100 | 6.6 | 8.6 | 6.3 | 6.6 | 6.5 | 6.5 | 6.7 | 6.7 | 6.7 | 6.6 |
| 155 | 5.8 | 5.5 | 5.5 | 5.6 | 100 | 5.6 | 7.2 | 5.6 | 6.5 | 5.4 | 5.4 | 5.5 | 5.5 | 5.7 | 5.6 |
| 157 | 6.1 | 6.2 | 6.3 | 6.4 | 100 | 6.1 | 9.0 | 6.0 | 6.0 | 6.1 | 6.1 | 6.2 | 6.4 | 6.5 | 6.3 |
| 158 | 6.3 | 6.5 | 6.7 | 6.5 | 100 | 6.7 | 10.0 | 6.3 | 6.4 | 6.4 | 6.2 | 6.3 | 6.5 | 6.5 | 6.3 |
| 156 | 5.4 | 5.7 | 5.5 | 5.7 | 100 | 5.7 | 8.9 | 5.6 | 5.5 | 5.3 | 5.4 | 5.5 | 5.6 | 5.6 | 5.7 |
| 144 | 5.7 | 5.6 | 5.6 | 5.4 | 100 | 5.6 | 8.1 | 5.6 | 5.8 | 5.7 | 5.7 | 5.7 | 5.8 | 5.7 | 5.9 |
| 159 | 5.3 | 5.4 | 5.4 | 5.5 | 100 | 5.5 | 7.6 | 5.5 | 5.5 | 5.3 | 5.3 | 5.4 | 5.9 | 5.4 | 5.5 |
| 160 | 6.3 | 6.5 | 6.1 | 6.2 | 100 | 6.5 | 8.7 | 6.1 | 5.4 | 5.0 | 6.1 | 6.2 | 6.2 | 6.3 | 6.2 |
| 133 | 4.7 | 4.9 | 4.7 | 4.9 | 100 | 4.7 | 8.8 | 4.6 | 4.7 | 4.7 | 4.6 | 4.6 | 4.7 | 4.9 | 4.8 |
| 134 | 5.1 | 5.1 | 5.0 | 5.0 | 100 | 5.2 | 9.6 | 5.1 | 5.7 | 5.0 | 5.1 | 5.1 | 5.2 | 5.1 | 5.2 |
| 132 | 4.9 | 4.8 | 4.8 | 4.8 | 100 | 4.7 | 9.7 | 4.5 | 4.7 | 4.7 | 4.8 | 4.7 | 4.7 | 4.8 | 4.7 |
| 135 | 5.3 | 5.2 | 5.0 | 5.0 | 100 | 5.0 | 7.0 | 5.2 | 5.0 | 5.1 | 5.1 | 5.0 | 5.0 | 5.1 | 5.3 |
| 136 | 5.2 | 5.3 | 5.1 | 5.2 | 100 | 5.2 | 7.2 | 5.4 | 5.4 | 5.2 | 5.2 | 5.3 | 5.5 | 5.1 | 5.5 |
| 137 | 5.9 | 6.1 | 5.4 | 5.6 | 100 | 5.7 | 7.1 | 5.8 | 5.9 | 5.6 | 5.8 | 5.6 | 5.7 | 5.7 | 5.7 |

Example 20

Motor Neuron Protective Effect of Anti-EphA4 Monoclonal Humanized Antibody in In Vitro ALS Model Derived from Human iPS Cells Human iPS cells are maintained and cultured according to the following steps. Human iPS cells (201B7) cryopreserved in liquid nitrogen using Stem cell banker (TAKARA) are taken out of the gas phase of liquid nitrogen and immediately suspended and thawed in 5 mL of a human iPS cell culture medium (Essential 8, Thermo Fisher Scientific) prewarmed to 37° C. The cell suspension is recovered into a 15-mL conical tube (Falcon) and centrifuged (1000 rpm, 5 min, room temperature), followed by the removal of the supernatant. The cells are suspended in a fresh medium and then disseminated to a ϕ60 mm cell culture dish (Falcon BD) coated with 0.5 μg/cm$^2$ Human recombinant vitronectin (Invitrogen) in advance. 10 μM of Y-27632 (Wako Pure Chemical Industries) is added thereto, and the cells is maintained and cultured in a $CO_2$ incubator (5% $CO_2$, 37° C.). Medium replacement is performed every day, and the cells are subjected to the experiment when reaching confluency.

The motor neuron protective effect of the anti-EphA4 monoclonal humanized antibody obtained in Example 16 in the in vitro ALS models is evaluated according to the following steps. The culture medium of the maintained and cultured human iPS cells is aspirated, and the cells are washed with 2 mL of PBS (Wako Pure Chemical Industries). After aspiration of PBS, 500 μL of 0.5 mM EDTA is added to the cells, which are then incubated for 2 to 3 minutes in a $CO_2$ incubator (5% $CO_2$, 37° C.) (the cells are confirmed under a microscope every 30 seconds, and the incubation is discontinued when the intercellular association became weak). The EDTA reaction is terminated by suspension in 5 mL of a human iPS cell culture medium, and the cells are recovered into a 15-mL conical tube. The cells are centrifuged at 1000 rpm at room temperature for 5 minutes, and the supernatant is aspirated. The cell suspension containing human iPS cell masses is inoculated in an amount of approximately 1/10 per well to a low-adhesion 6-well cell culture plate (Nunclon Sphere, Nunc) and cultured in a $CO_2$ incubator (5% $CO_2$, 37° C.) using a DFK medium (advanced DMEM/F-12 (Invitrogen):Neurobasal medium (Invitrogen) [1:1] medium containing 2% B27 supplement, 5% Knock-Out serum replacement (Invitrogen), 2 mmol/L L-glutamine, 100 units/mL penicillin-100 μg/mL streptomycin, and 0.1 mmol/L β-mercaptoethanol) supplemented with 2 μM SB431542 (Sigma-Aldrich), 300 nM LDN193189 (Sigma-Aldrich), and 3 μM CHIR99021 (Sigma-Aldrich). Medium replacement is performed every 2 days by the following method. First, a human iPS cell differentiated cell aggregates (SFEBs) is recovered on a medium basis into a 15-mL conical tube and left standing at ordinary temperature for 5 minutes to precipitate the cell masses. This supernatant is aspirated, and a fresh DFK medium and 2 μM SB431542 (Sigma-Aldrich), 300 nM LDN193189 (Sigma-Aldrich), 3 μM CHIR99021 (Sigma-Aldrich) are added, and then brought back to the original well for medium replacement. At culture day 8, the SFEBs are recovered on a medium basis into a 15-mL conical tube and left standing at ordinary temperature for 5 minutes to precipitate the SFEBs. This supernatant is aspirated, and a fresh DFK medium and then 0.1 μM retinoic acid (Sigma-Aldrich) and 0.5 μM purmorphamine (Miltenyi Biotec) are added, and then brought back to the original well and cultured in a $CO_2$ incubator (5% $CO_2$, 37° C.). Medium replacement is performed every 2 days. At culture day 12, the SFEBs are recovered on a medium basis into a 15-mL conical tube and left standing at ordinary temperature for 5 minutes to precipitate the SFEBs. The supernatant is aspirated, and 500 μL of Accumax (MS TechnoSystems) is added to the cells, which are then pipetted several times and then incubated for 5 minutes in a $CO_2$ incubator (5% $CO_2$, 37° C.). The cells are taken out of the incubator, suspended in 5 mL of a DFK medium, and pipetted several times to disperse the cell masses. The cell suspension is dissociated into single cells by filtration through a cell strainer (Falcon). Then, the number of cells is counted using a counting chamber. The cell suspension is recovered into another 15-mL conical tube and centrifuged at 1000 rpm at room temperature for 5 minutes. A suspension having a cell density of 5.5×10$^5$ cells/mL is prepared with a motoneuron culture medium (advanced DMEM/F-12 (Invitrogen):Neurobasal medium (Invitrogen) [1:1] medium containing 2% B27 Supplement, 1% horse serum, 2 mmol/L L-glutamine, 100 units/mL penicillin-100 μg/mL streptomycin, and 0.1 mmol/L β-mercaptoethanol) and inoculated at 200 μL/well to an 8-well chamber containing mouse-derived wild-type astrocytes or variant human SOD1 (G93A)-expressing astrocytes inoculated at 8×10$^4$ cells/well in advance. The resulting cocultured cells of the astrocytes and the motor neurons are used in evaluation (the establishment, freezing, thawing, inoculation, and maintenance and culture of the wild-type and human variant SOD1 (G93A)-expressing astrocytes are performed in the same way as in Example 13). The number of motor neurons observed by the coculture of the wild-type astrocytes and the motor neurons is used as a control. For the drug-treated group, the variant human SOD1 (G93A)-expressing astrocytes and the motor neurons are cocultured under a condition involving vehicle addition (IgG and 0.1% ultrapure water) and the humanized antibody. After culture for 2 days at 37° C. in a 5% $CO_2$ environment under each condition, the motor neurons are immunocytochemically stained with an anti-ISL1 antibody (obtained from Developmental Studies Hybridoma Bank) and Hoechst 33342 (Molecular Probes). ISL1/Hoechst 33342-copositive cells per well are counted as live motor neurons, and the survival rate of the motor neurons is calculated as % with respect to the control.

The survival rate of the motor neurons is significantly reduced in the variant human SOD1 (G93A)-expressing astrocyte/human iPS cell-derived motor neuron coculture. The humanized antibody described in Table 5 suppressed, in a concentration-dependent manner, human iPS cell-derived motor neuron death induced by the variant human SOD1 (G93A)-expressing astrocytes. Accordingly, it is shown that the anti-EphA4 monoclonal humanized antibody promotes the survival of motor neurons in human cells.

INDUSTRIAL APPLICABILITY

The present invention can provide an anti-EphA4 antibody or an EphA4-binding fragment thereof which is capable of binding to EphA4 and inhibiting the binding between EphA4 and its ligand, and a pharmaceutical composition comprising the anti-EphA4 antibody or the EphA4-binding fragment thereof as an active ingredient. The antibody or the pharmaceutical composition according to the present invention can be useful in the treatment of diseases caused by the binding between EphA4 and its ligand, for example, ALS.

What is claimed is:

1. An anti-EphA4 antibody or an EphA4-binding fragment thereof, comprising a heavy chain variable region and a light chain variable region,
   wherein the heavy chain variable region comprises
   (a) CDR-H1 comprising the amino acid sequence represented by or SEQ ID NO: 27;
   (b) CDR-H2 comprising the amino acid sequence represented by or SEQ ID NO: 29; and
   (c) CDR-H3 comprising the amino acid sequence represented by SEQ ID NO: 30; and
   wherein the light chain variable region comprises
   (d) CDR-L1 comprising the amino acid sequence represented by SEQ ID NO: 31;
   (e) CDR-L2 comprising the amino acid sequence represented by SEQ ID NO: 32; and
   (f) CDR-L3 comprising the amino acid sequence represented by SEQ ID NO: 33.

2. The anti-EphA4 antibody or the EphA4-binding fragment thereof according to claim 1, wherein the antibody or the EphA4-binding fragment thereof is humanized.

3. The anti-EphA4 antibody or the EphA4-binding fragment thereof according to claim 1, wherein the antibody or the EphA4-binding fragment thereof comprises a heavy chain and a light chain, and a constant region of the heavy chain and a constant region of the light chain each comprise a human antibody-derived sequence.

4. The anti-EphA4 antibody or the EphA4-binding fragment thereof according to claim 3, wherein the constant region of the heavy chain is derived from human IgG.

5. The anti-EphA4 antibody or the EphA4-binding fragment thereof according to claim 4, wherein the human IgG is human $IgG_1$ or human $IgG_2$.

6. The anti-EphA4 antibody or the EphA4-binding fragment thereof according to claim 3, wherein the constant region of the light chain is derived from human Igκ.

7. The anti-EphA4 antibody or the EphA4-binding fragment thereof according to claim 1, wherein the EphA4-binding fragment is selected from the group consisting of Fab, Fab', $F(ab')_2$, and Fv.

8. The anti-EphA4 antibody or the EphA4-binding fragment thereof according to claim 7, wherein the EphA4-binding fragment is $F(ab')_2$.

9. A pharmaceutical composition comprising the anti-EphA4antibody or the EphA 4-binding fragment thereof according to claim 1.

10. The pharmaceutical composition according to claim 9 further comprising a pharmaceutically acceptable carrier.

11. A method of treating amyotrophic lateral sclerosis (ALS) in a human subject in need thereof, comprising administering an effective amount of the pharmaceutical composition of claim 9 to the subject.

12. An anti-EphA4 antibody or an EphA4-binding fragment thereof, comprising a heavy chain variable region and a light chain variable region, wherein the heavy chain variable region comprises the amino acid sequence represented by SEQ ID NO: 66, 68 or 70 and the light chain variable region comprises the amino acid sequence represented by SEQ ID NO: 78, 80, 82 or 84.

13. The anti-EphA4 antibody or the EphA4-binding fragment thereof according to claim 12, wherein the heavy chain variable region comprises the amino acid sequence represented by SEQ ID NO: 66, and the light chain variable region comprises the amino acid sequence represented by SEQ ID NO: 78.

14. The anti-EphA4 antibody or the EphA4-binding fragment thereof according to claim 12, wherein the heavy chain variable region comprises the amino acid sequence represented by SEQ ID NO: 68, and the light chain variable region comprises the amino acid sequence represented by SEQ ID NO: 78.

15. The anti-EphA4 antibody or the EphA4-binding fragment thereof according to claim 12, wherein the heavy chain variable region comprises the amino acid sequence represented by SEQ ID NO: 70, and the light chain variable region comprises the amino acid sequence represented by SEQ ID NO: 78.

16. The anti-EphA4 antibody or the EphA4-binding fragment thereof according to claim 12, wherein the heavy chain variable region comprises the amino acid sequence represented by SEQ ID NO: 66, and the light chain variable region comprises the amino acid sequence represented by SEQ ID NO: 80.

17. The anti-EphA4 antibody or the EphA4-binding fragment thereof according to claim 12, wherein the heavy chain variable region comprises the amino acid sequence represented by SEQ ID NO: 68, and the light chain variable region comprises the amino acid sequence represented by SEQ ID NO: 80.

18. The anti-EphA4 antibody or the EphA4-binding fragment thereof according to claim 12, wherein the heavy chain variable region comprises the amino acid sequence represented by SEQ ID NO: 70, and the light chain variable region comprises the amino acid sequence represented by SEQ ID NO: 80.

19. The anti-EphA4 antibody or the EphA4-binding fragment thereof according to claim 12, wherein the heavy chain variable region comprises the amino acid sequence represented by SEQ ID NO: 66, and the light chain variable region comprises the amino acid sequence represented by SEQ ID NO: 82.

20. The anti-EphA4 antibody or the EphA4-binding fragment thereof according to claim 12, wherein the heavy chain variable region comprises the amino acid sequence represented by SEQ ID NO: 68, and the light chain variable region comprises the amino acid sequence represented by SEQ ID NO: 82.

21. The anti-EphA4 antibody or the EphA4-binding fragment thereof according to claim 12, wherein the heavy chain variable region comprises the amino acid sequence represented by SEQ ID NO: 70, and the light chain variable region comprises the amino acid sequence represented by SEQ ID NO: 82.

22. The anti-EphA4 antibody or the EphA4-binding fragment thereof according to claim 12, wherein the heavy chain variable region comprises the amino acid sequence represented by SEQ ID NO: 68, and the light chain variable region comprises the amino acid sequence represented by SEQ ID NO: 84.

23. The anti-EphA4 antibody or the EphA4-binding fragment thereof according to claim 12, wherein the antibody or the EphA4-binding fragment thereof comprises a heavy chain and a light chain, and a constant region of the heavy chain and a constant region of the light chain each comprise a human antibody-derived sequence.

24. The anti-EphA4 antibody or the EphA4-binding fragment thereof according to claim 23, wherein the constant region of the heavy chain is derived from human IgG.

25. The anti-EphA4 antibody or the EphA4-binding fragment thereof according to claim 24, wherein the human IgG is human IgG consisting of human $IgG_2$ or a combination of human $IgG_1$ and human $IgG_2$.

26. The anti-EphA4 antibody or the EphA4-binding fragment thereof according to claim 25, wherein the human IgG is human $IgG_2$.

27. The anti-EphA4 antibody or the EphA4-binding fragment thereof according to claim 26, wherein the human $IgG_2$ has a C131S, C219S, V234A and/or G237A mutation under Eu numbering, and does not have a lysine residue at the carboxy terminal.

28. The anti-EphA4 antibody or the EphA4-binding fragment thereof according to claim 27, wherein the human $IgG_2$ comprises the amino acid sequence represented by SEQ ID NO: 62.

29. The anti-EphA4 antibody or the EphA4-binding fragment thereof according to claim 25, wherein the human IgG is human IgG consisting of a combination of human $IgG_1$ and human $IgG_2$.

30. The anti-EphA4 antibody or the EphA4-binding fragment thereof according to claim 29, wherein in the human IgG consisting of a combination of human $IgG_1$ and human $IgG_2$, a CH1 region and a hinge region are human $IgG_1$, and a CH2 region and a CH3 region are human $IgG_2$.

31. The anti-EphA4 antibody or the EphA4-binding fragment thereof according to claim 30, wherein the human IgG consisting of a combination of human $IgG_1$ and human $IgG_2$ has a V234A and/or a G237A mutation under Eu numbering, and does not have a lysine residue at the carboxy terminal.

32. The anti-EphA4 antibody or the EphA4-binding fragment thereof according to claim 31, wherein the human IgG consisting of a combination of human $IgG_1$ and human $IgG_2$ comprises the amino acid sequence represented by SEQ ID NO: 60.

33. The anti-EphA4 antibody or the EphA4-binding fragment thereof according to claim 23, wherein the constant region of the light chain is derived from human Igκ.

34. The anti-EphA4 antibody or the EphA4-binding fragment thereof according to claim 12, wherein the EphA4-binding fragment is selected from the group consisting of Fab, Fab', F(ab')$_2$, and Fv.

35. The anti-EphA4 antibody or the EphA4-binding fragment thereof according to claim 34, wherein the EphA4-binding fragment is F(ab')$_2$.

36. A pharmaceutical composition comprising the anti-EphA4 antibody or the EphA4-binding fragment thereof according to claim 12.

37. The pharmaceutical composition according to claim 36 further comprising a pharmaceutically acceptable carrier.

38. A method of treating amyotrophic lateral sclerosis (ALS) in a human subject in need thereof, comprising administering an effective amount of the pharmaceutical composition of claim 36 to the subject.

39. An anti-EphA4 antibody or an EphA4-binding fragment thereof, comprising a heavy chain variable region and a light chain variable region, wherein the heavy chain variable region comprises the amino acid sequence represented by SEQ ID NO: 66 and the light chain variable region comprises the amino acid sequence represented by SEQ ID NO: 84.

40. The anti-EphA4 antibody or the EphA4-binding fragment thereof according to claim 39, wherein the antibody or the EphA4-binding fragment thereof comprises a heavy chain and a light chain, and a constant region of the heavy chain and a constant region of the light chain each comprise a human antibody-derived sequence.

41. The anti-EphA4 antibody or the EphA4-binding fragment thereof according to claim 40, wherein the constant region of the heavy chain is derived from human IgG.

42. The anti-EphA4 antibody or the EphA4-binding fragment thereof according to claim 41, wherein the human IgG is human IgG consisting of human $IgG_2$ or a combination of human $IgG_1$ and human $IgG_2$.

43. The anti-EphA4 antibody or the EphA4-binding fragment thereof according to claim 42, wherein the human IgG is human $IgG_2$.

44. The anti-EphA4 antibody or the EphA4-binding fragment thereof according to claim 43, wherein the human $IgG_2$ has a C131S, C219S, V234A and/or G237A mutation under Eu numbering, and does not have a lysine residue at the carboxy terminal.

45. The anti-EphA4 antibody or the EphA4-binding fragment thereof according to claim 44, wherein the human $IgG_2$ comprises the amino acid sequence represented by SEQ ID NO: 62.

46. The anti-EphA4 antibody or the EphA4-binding fragment thereof according to claim 42, wherein the human IgG is human IgG consisting of a combination of human $IgG_1$ and human $IgG_2$.

47. The anti-EphA4 antibody or the EphA4- binding fragment thereof according to claim 46, wherein in the human IgG consisting of a combination of human $IgG_1$ and human $IgG_2$, a CH1 region and a hinge region are human $IgG_1$, and a CH2 region and a CH3 region are human $IgG_2$.

48. The anti-EphA4 antibody or the EphA4-binding fragment thereof according to claim 47, wherein the human IgG consisting of a combination of human $IgG_1$ and human $IgG_2$ has a V234A and/or a G237A mutation under Eu numbering, and does not have a lysine residue at the carboxy terminal.

49. The anti-EphA4 antibody or the EphA4-binding fragment thereof according to claim 48, wherein the human IgG consisting of a combination of human $IgG_1$ and human $IgG_2$ comprises the amino acid sequence represented by SEQ ID NO: 60.

50. The anti-EphA4 antibody or the EphA4-binding fragment thereof according to claim 40, wherein the constant region of the light chain is derived from human Igκ.

51. The anti-EphA4 antibody or the EphA4-binding fragment thereof according to claim 39, wherein the EphA4-binding fragment is selected from the group consisting of Fab, Fab', F(ab')$_2$, and Fv.

52. The anti-EphA4 antibody or the EphA4-binding fragment thereof according to claim 51, wherein the EphA4-binding fragment is F(ab')$_2$.

53. A pharmaceutical composition comprising the anti-EphA4 antibody or the EphA4-binding fragment thereof according to claim 39.

54. The pharmaceutical composition according to claim 53 further comprising a pharmaceutically acceptable carrier.

55. A method of treating amyotrophic lateral sclerosis (ALS) in a human subject in need thereof, comprising administering an effective amount of the pharmaceutical composition of claim 53 to the subject.

56. An isolated nucleic acid or nucleic acids encoding the anti-EphA4 antibody or the EphA4-binding fragment thereof according to claim 39.

57. A vector or vectors comprising the nucleic acid or nucleic acids according to claim 56.

58. A host cell comprising the vector or vectors according to claim 57.

59. A method of producing an anti-EphA4 antibody or an EphA4-binding fragment thereof comprising the step of culturing the host cell according to claim 58.

60. An anti-EphA4 antibody or an EphA4-binding fragment thereof, comprising a heavy chain variable region and a light chain variable region, wherein the heavy chain variable region comprises the amino acid sequence represented by SEQ ID NO: 70 and the light chain variable region comprises the amino acid sequence represented by SEQ ID NO: 84.

61. The anti-EphA4 antibody or the EphA4-binding fragment thereof according to claim 60, wherein the antibody or the EphA4-binding fragment thereof comprises a heavy chain and a light chain, and a constant region of the heavy chain and a constant region of the light chain each comprise a human antibody-derived sequence.

62. The anti-EphA4 antibody or the EphA4-binding fragment thereof according to claim 60, wherein the constant region of the heavy chain is derived from human IgG.

63. The anti-EphA4 antibody or the EphA4-binding fragment thereof according to claim 62, wherein the human IgG is human IgG consisting of human $IgG_2$ or a combination of human $IgG_1$ and human $IgG_2$.

64. The anti-EphA4 antibody or the EphA4-binding fragment thereof according to claim 63, wherein the human IgG is human $IgG_2$.

65. The anti-EphA4 antibody or the EphA4-binding fragment thereof according to claim 64, wherein the human $IgG_2$ has a C131S, C219S, V234A and/or G237A mutation under Eu numbering, and does not have a lysine residue at the carboxy terminal.

66. The anti-EphA4 antibody or the EphA4-binding fragment thereof according to claim 65, wherein the human $IgG_2$ comprises the amino acid sequence represented by SEQ ID NO: 62.

67. The anti-EphA4 antibody or the EphA4-binding fragment thereof according to claim 63, wherein the human IgG is human IgG consisting of a combination of human $IgG_1$ and human $IgG_2$.

68. The anti-EphA4 antibody or the EphA4-binding fragment thereof according to claim 67, wherein in the human IgG consisting of a combination of human $IgG_1$ and human $IgG_2$, a CH1 region and a hinge region are human $IgG_1$, and a CH2 region and a CH3 region are human $IgG_2$.

69. The anti-EphA4 antibody or the EphA4-binding fragment thereof according to claim 68, wherein the human IgG consisting of a combination of human $IgG_1$ and human $IgG_2$ has a V 234A and/or a G237A mutation under Eu numbering, and does not have a lysine residue at the carboxy terminal.

70. The anti-EphA4 antibody or the EphA4-binding fragment thereof according to claim 69, wherein the human IgG consisting of a combination of human $IgG_1$ and human $IgG_2$ comprises the amino acid sequence represented by SEQ ID NO: 60.

71. The anti-EphA4 antibody or the EphA4-binding fragment thereof according to claim 61, wherein the constant region of the light chain is derived from human Igκ.

72. The anti-EphA4 antibody or the EphA4-binding fragment thereof according to claim 60, wherein the EphA4-binding fragment is selected from the group consisting of Fab, Fab', F(ab')$_2$, and Fv.

73. The anti-EphA4 antibody or the EphA4-binding fragment thereof according to claim 72, wherein the EphA4-binding fragment is F(ab')$_2$.

74. A pharmaceutical composition comprising the anti-EphA4 antibody or the EphA4-binding fragment thereof according to claim 60.

75. The pharmaceutical composition according to claim 74 further comprising a pharmaceutically acceptable carrier.

76. A method of treating amyotrophic lateral sclerosis (ALS) in a human subject in need thereof, comprising administering an effective amount of the pharmaceutical composition of claim 74 to the subject.

77. An isolated nucleic acid or nucleic acids encoding the anti-EphA4 antibody or the EphA4-binding fragment thereof according to claim 60.

78. A vector or vectors comprising the nucleic acid or nucleic acids according to claim 77.

79. A host cell comprising the vector or vectors according to claim 78.

80. A method of producing an anti-EphA4 antibody or an EphA4-binding fragment thereof comprising the step of culturing the host cell according to claim 79.

* * * * *

UNITED STATES PATENT AND TRADEMARK OFFICE
CERTIFICATE OF CORRECTION

PATENT NO. : 10,428,140 B2
APPLICATION NO. : 15/753611
DATED : October 1, 2019
INVENTOR(S) : Ryota Taguchi et al.

It is certified that error appears in the above-identified patent and that said Letters Patent is hereby corrected as shown below:

In the Specification

Column 24, Table 1
Line 32, delete "GYTFDYSMH" and insert -- GYTFTDYSMH --.
Line 39, delete "IPLYYYGSHYWYFDV" and insert -- IPLYYYGSRYWYFDV --.
Line 46, delete "QHPNGTPWT" and insert -- QHFWGTPWT --.

Column 34
Line 62, delete "aantagonistic" and insert -- antagonistic --.

Column 45, Table 6
Line 60, delete "3.8E+05" and insert -- 3.6E+05 --.

Column 46, Table 6
Line 18, delete "5.6E-04" and insert -- 5.8E-04 --.
Line 26, delete "0.08" and insert -- 0.06 --.
Line 36, delete "2.9E+05" and insert -- 2.8E+05 --.
Line 37, delete "28" and insert -- 26 --.
Line 38, delete "6.5E-04" and insert -- 8.5E-04 --.
Line 42, delete "158" and insert -- 156 --.
Line 42, delete "1.6E-09" and insert -- 1.8E-09 --.
Line 45, delete "2.8E+05" and insert -- 2.6E+05 --.
Line 46, delete "0.08" and insert -- 0.06 --.
Line 48, delete "138" and insert -- 136 --.
Line 49, delete "3.9E-04" and insert -- 3.8E-04 --.

Column 47, Table 7
Line 35, delete "4.6" and insert -- 4.8 --.

Signed and Sealed this
Twenty-eighth Day of April, 2020

Andrei Iancu
*Director of the United States Patent and Trademark Office*

CERTIFICATE OF CORRECTION (continued)
U.S. Pat. No. 10,428,140 B2

In the Claims

Column 124
Claim 9, Line 58, delete "EphA4antibody" and insert -- EphA4 antibody --.
Claim 9, Line 58, "EphA 4-binding" and insert -- EphA4-binding --.

Column 125
Claim 12, Line 5, delete "78 ," and insert -- 78, --.

Column 126
Claim 29, Line 28, delete "IgG$_1$and" and insert -- IgG$_1$ and --.
Claim 32, Line 43, delete "IgG$_2$comprises" and insert -- IgG$_2$ comprises --.

Column 127
Claim 46, Line 32, delete "IgG$_1$and" and insert -- IgG$_1$ and --.
Claim 47, Line 33, delete "EphA4- binding" and insert -- EphA4-binding --.
Claim 48, Line 41, delete "IgG$_2$has" and insert -- IgG$_2$ has --.
Claim 49, Line 47, delete "IgG$_2$comprises" and insert -- IgG$_2$ comprises --.

Column 128
Claim 62, Line 26, delete "claim 60" and insert -- claim 61 --.
Claim 67, Line 48, delete "IgG$_1$and" and insert -- IgG$_1$ and --.
Claim 69, Line 57, delete "IgG$_2$has" and insert -- IgG$_2$ has --.
Claim 69, Line 57, delete "V 234A" and insert -- V234A --.
Claim 70, Line 63, delete "IgG$_2$comprises" and insert -- IgG$_2$ comprises --.

SEQUENCE LISTING

<160> NUMBER OF SEQ ID NOS: 85

<210> SEQ ID NO 1
<211> LENGTH: 986
<212> TYPE: PRT
<213> ORGANISM: Mus musculus

<400> SEQUENCE: 1

```
Met Ala Gly Ile Phe Tyr Phe Ile Leu Phe Ser Phe Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Ala Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Ser Gln Phe Gly Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Gln Asn Gly Glu
            260                 265                 270

Cys Gln Ala Cys Lys Ile Gly Tyr Tyr Lys Ala Leu Ser Thr Asp Ala
        275                 280                 285

Ser Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
        355                 360                 365
```

-continued

```
Cys Gly Ala Gly Asp Pro Ser Lys Cys Arg Pro Cys Gly Ser Gly Val
    370                 375                 380

His Tyr Thr Pro Gln Gln Asn Gly Leu Lys Thr Thr Arg Val Ser Ile
385                 390                 395                 400

Thr Asp Leu Leu Ala His Thr Asn Tyr Thr Phe Glu Ile Trp Ala Val
            405                 410                 415

Asn Gly Val Ser Lys Tyr Asn Pro Ser Pro Asp Gln Ser Val Ser Val
                420                 425                 430

Thr Val Thr Thr Asn Gln Ala Ala Pro Ser Ser Ile Ala Leu Val Gln
            435                 440                 445

Ala Lys Glu Val Thr Arg Tyr Ser Val Ala Leu Ala Trp Leu Glu Pro
450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
            515                 520                 525

Glu Val Thr Thr Asn Thr Val Pro Ser Arg Ile Ile Gly Asp Gly Ala
            530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Ser Lys Tyr
                565                 570                 575

Ser Lys Ala Lys Gln Glu Ala Asp Glu Lys His Leu Asn Gln Gly
                580                 585                 590

Val Arg Thr Tyr Val Asp Pro Phe Thr Tyr Glu Asp Pro Asn Gln Ala
            595                 600                 605

Val Arg Glu Phe Ala Lys Glu Ile Asp Ala Ser Cys Ile Lys Ile Glu
610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
            645                 650                 655

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
            675                 680                 685

Val Thr Lys Cys Lys Pro Val Met Ile Ile Thr Glu Tyr Met Glu Asn
            690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
            755                 760                 765

Arg Val Leu Glu Asp Asp Pro Glu Ala Ala Tyr Thr Thr Arg Gly Gly
770                 775                 780
```

-continued

```
Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
            805                 810                 815

Val Met Ser Tyr Gly Glu Arg Pro Tyr Trp Asp Met Ser Asn Gln Asp
        820                 825                 830

Val Ile Lys Ala Ile Glu Glu Gly Tyr Arg Leu Pro Pro Pro Met Asp
    835                 840                 845

Cys Pro Ile Ala Leu His Gln Leu Met Leu Asp Cys Trp Gln Lys Glu
850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Ser Glu Ser Ser
            885                 890                 895

Arg Pro Asn Thr Ala Leu Leu Asp Pro Ser Ser Pro Glu Phe Ser Ala
        900                 905                 910

Val Val Ser Val Gly Asp Trp Leu Gln Ala Ile Lys Met Asp Arg Tyr
    915                 920                 925

Lys Asp Asn Phe Thr Ala Ala Gly Tyr Thr Thr Leu Glu Ala Val Val
930                 935                 940

His Met Ser Gln Asp Asp Leu Ala Arg Ile Gly Ile Thr Ala Ile Thr
945                 950                 955                 960

His Gln Asn Lys Ile Leu Ser Ser Val Gln Ala Met Arg Thr Gln Met
            965                 970                 975

Gln Gln Met His Gly Arg Met Val Pro Val
        980                 985

<210> SEQ ID NO 2
<211> LENGTH: 528
<212> TYPE: PRT
<213> ORGANISM: Mus musculus

<400> SEQUENCE: 2

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Ala Ser Gln Asn Asn Trp
    50                  55                  60

Leu Arg Thr Asp Trp Ile Thr Arg Glu Gly Ala Gln Arg Val Tyr Ile
65              70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175
```

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
            195                 200                 205

Glu Val Arg Gly Ser Cys Val Asn Asn Ser Glu Glu Lys Asp Val Pro
210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
            245                 250                 255

Cys Lys Ile Gly Tyr Tyr Lys Ala Leu Ser Thr Asp Ala Ser Cys Ala
            260                 265                 270

Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
            290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
            325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Arg Val Ser Ile Thr Asp Leu
            370                 375                 380

Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
            405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
            485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
            515                 520                 525

<210> SEQ ID NO 3
<211> LENGTH: 986
<212> TYPE: PRT
<213> ORGANISM: Homo sapiens

<400> SEQUENCE: 3

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr

```
                20                  25                  30
Leu Leu Asp Ser Arg Ser Val Gln Gly Glu Leu Gly Trp Ile Ala Ser
            35                  40                  45
Pro Leu Glu Gly Gly Trp Glu Glu Val Ser Ile Met Asp Glu Lys Asn
        50                  55                  60
Thr Pro Ile Arg Thr Tyr Gln Val Cys Asn Val Met Glu Pro Ser Gln
    65                  70                  75                  80
Asn Asn Trp Leu Arg Thr Asp Trp Ile Thr Arg Glu Gly Ala Gln Arg
                85                  90                  95
Val Tyr Ile Glu Ile Lys Phe Thr Leu Arg Asp Cys Asn Ser Leu Pro
            100                 105                 110
Gly Val Met Gly Thr Cys Lys Glu Thr Phe Asn Leu Tyr Tyr Tyr Glu
        115                 120                 125
Ser Asp Asn Asp Lys Glu Arg Phe Ile Arg Glu Asn Gln Phe Val Lys
    130                 135                 140
Ile Asp Thr Ile Ala Ala Asp Glu Ser Phe Thr Gln Val Asp Ile Gly
145                 150                 155                 160
Asp Arg Ile Met Lys Leu Asn Thr Glu Ile Arg Asp Val Gly Pro Leu
                165                 170                 175
Ser Lys Lys Gly Phe Tyr Leu Ala Phe Gln Asp Val Gly Ala Cys Ile
            180                 185                 190
Ala Leu Val Ser Val Arg Val Phe Tyr Lys Lys Cys Pro Leu Thr Val
        195                 200                 205
Arg Asn Leu Ala Gln Phe Pro Asp Thr Ile Thr Gly Ala Asp Thr Ser
    210                 215                 220
Ser Leu Val Glu Val Arg Gly Ser Cys Val Asn Asn Ser Glu Glu Lys
225                 230                 235                 240
Asp Val Pro Lys Met Tyr Cys Gly Ala Asp Gly Glu Trp Leu Val Pro
                245                 250                 255
Ile Gly Asn Cys Leu Cys Asn Ala Gly His Glu Glu Arg Ser Gly Glu
            260                 265                 270
Cys Gln Ala Cys Lys Ile Gly Tyr Tyr Lys Ala Leu Ser Thr Asp Ala
        275                 280                 285
Thr Cys Ala Lys Cys Pro Pro His Ser Tyr Ser Val Trp Glu Gly Ala
    290                 295                 300
Thr Ser Cys Thr Cys Asp Arg Gly Phe Phe Arg Ala Asp Asn Asp Ala
305                 310                 315                 320
Ala Ser Met Pro Cys Thr Arg Pro Pro Ser Ala Pro Leu Asn Leu Ile
                325                 330                 335
Ser Asn Val Asn Glu Thr Ser Val Asn Leu Glu Trp Ser Ser Pro Gln
            340                 345                 350
Asn Thr Gly Gly Arg Gln Asp Ile Ser Tyr Asn Val Val Cys Lys Lys
        355                 360                 365
Cys Gly Ala Gly Asp Pro Ser Lys Cys Arg Pro Cys Gly Ser Gly Val
    370                 375                 380
His Tyr Thr Pro Gln Gln Asn Gly Leu Lys Thr Thr Lys Val Ser Ile
385                 390                 395                 400
Thr Asp Leu Leu Ala His Thr Asn Tyr Thr Phe Glu Ile Trp Ala Val
                405                 410                 415
Asn Gly Val Ser Lys Tyr Asn Pro Asn Pro Asp Gln Ser Val Ser Val
            420                 425                 430
Thr Val Thr Thr Asn Gln Ala Ala Pro Ser Ser Ile Ala Leu Val Gln
        435                 440                 445
```

```
Ala Lys Glu Val Thr Arg Tyr Ser Val Ala Leu Ala Trp Leu Glu Pro
    450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
        515                 520                 525

Glu Val Thr Thr Asn Thr Val Pro Ser Arg Ile Ile Gly Asp Gly Ala
    530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Ser Lys Tyr
                565                 570                 575

Ser Lys Ala Lys Gln Glu Ala Asp Glu Lys His Leu Asn Gln Gly
                580                 585                 590

Val Arg Thr Tyr Val Asp Pro Phe Thr Tyr Glu Asp Pro Asn Gln Ala
    595                 600                 605

Val Arg Glu Phe Ala Lys Glu Ile Asp Ala Ser Cys Ile Lys Ile Glu
    610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
                675                 680                 685

Val Thr Lys Cys Lys Pro Val Met Ile Ile Thr Glu Tyr Met Glu Asn
        690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
        755                 760                 765

Arg Val Leu Glu Asp Asp Pro Glu Ala Ala Tyr Thr Thr Arg Gly Gly
    770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860
```

```
Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
            885                 890                 895

Arg Pro Asn Thr Ala Leu Leu Asp Pro Ser Pro Glu Phe Ser Ala
        900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
            965                 970                 975

Gln Gln Met His Gly Arg Met Val Pro Val
            980                 985

<210> SEQ ID NO 4
<211> LENGTH: 528
<212> TYPE: PRT
<213> ORGANISM: Homo sapiens

<400> SEQUENCE: 4

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255
```

Cys Lys Ile Gly Tyr Tyr Lys Ala Leu Ser Thr Asp Ala Thr Cys Ala
            260                 265                 270

Lys Cys Pro Pro His Ser Tyr Ser Val Trp Glu Ala Thr Ser Cys
            275                 280                 285

Thr Cys Asp Arg Gly Phe Phe Arg Ala Asp Asn Asp Ala Ala Ser Met
290                 295                 300

Pro Cys Thr Arg Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Lys Val Ser Ile Thr Asp Leu
370                 375                 380

Leu Ala His Thr Asn Tyr Thr Phe Glu Ile Trp Ala Val Asn Gly Val
385                 390                 395                 400

Ser Lys Tyr Asn Pro Asn Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
        515                 520                 525

<210> SEQ ID NO 5
<211> LENGTH: 12
<212> TYPE: DNA
<213> ORGANISM: Artificial Sequence
<220> FEATURE:
<223> OTHER INFORMATION: Synthetic primer

<400> SEQUENCE: 5
acatcactcc gt                                                             12

<210> SEQ ID NO 6
<211> LENGTH: 50
<212> TYPE: DNA
<213> ORGANISM: Artificial Sequence
<220> FEATURE:
<223> OTHER INFORMATION: Synthetic primer

<400> SEQUENCE: 6
acggagtgat gtccgtcgac gtatctctgc gttgatactt cagcgtagct                    50

<210> SEQ ID NO 7
<211> LENGTH: 26

```
<212> TYPE: DNA
<213> ORGANISM: Artificial Sequence
<220> FEATURE:
<223> OTHER INFORMATION: Synthetic primer

<400> SEQUENCE: 7
agctacgctg aagtatcaac gcagag                                          26

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gccagtggat agactgatgg                                                 20

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
gatggataca gttggtgcag c                                               21

<210> SEQ ID NO 10
<211> LENGTH: 19
<212> TYPE: PRT
<213> ORGANISM: Mus musculus

<400> SEQUENCE: 10

Met Ala Trp Val Trp Thr Leu Leu Phe Leu Met Ala Ala Ala Gln Ser
1               5                   10                  15

Ile Gln Ala

<210> SEQ ID NO 11
<211> LENGTH: 124
<212> TYPE: PRT
<213> ORGANISM: Mus musculus

<400> SEQUENCE: 11

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Ile Pro Leu Tyr Tyr Gly Ser Arg Tyr Trp Tyr Phe Asp
            100                 105                 110

Val Trp Gly Ala Gly Thr Thr Val Thr Val Ser Ser
        115                 120
```

-continued

```
<210> SEQ ID NO 12
<211> LENGTH: 20
<212> TYPE: PRT
<213> ORGANISM: Mus musculus

<400> SEQUENCE: 12

Met Ser Val Pro Thr Gln Val Leu Gly Leu Leu Leu Leu Trp Leu Thr
1               5                   10                  15

Asp Ala Arg Cys
            20

<210> SEQ ID NO 13
<211> LENGTH: 107
<212> TYPE: PRT
<213> ORGANISM: Mus musculus

<400> SEQUENCE: 13

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Arg Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Trp
                85                  90                  95

Thr Phe Gly Gly Gly Thr Lys Leu Glu Ile Lys
            100                 105

<210> SEQ ID NO 14
<211> LENGTH: 57
<212> TYPE: DNA
<213> ORGANISM: Mus musculus

<400> SEQUENCE: 14
atggcttggg tgtggacctt gctattcctg atggcagctg cccaaagtat ccaagca      57

<210> SEQ ID NO 15
<211> LENGTH: 372
<212> TYPE: DNA
<213> ORGANISM: Mus musculus

<400> SEQUENCE: 15
cagatccagt tggtgcagtc tggacctgag ctgaagaagc ctggagagac agtcaagatc    60
tcctgcaagg cttctggtta taccttcaca gactattcaa tgcactgggt gaagcaggct   120
ccaggaaagg gtttaaagtg gatgggctgg ataaacactg agactggtga gccaacatat   180
gcagatgact caagggacg gtttgccttc tctttggaaa cctctgccag cactgcctat   240
ttgcagatca acaacctcaa aaatgaggac acggctacat atttctgtgc tagaattccc   300
ctctattact acggtagtag gtactggtac ttcgatgtct ggggcgcagg gaccacggtc   360
accgtctcct ca                                                       372

<210> SEQ ID NO 16
<211> LENGTH: 60
<212> TYPE: DNA
<213> ORGANISM: Mus musculus
```

<400> SEQUENCE: 16
atgagtgtgc ccactcaggt cctggggttg ctgctgctgt ggcttacaga tgccagatgt    60

<210> SEQ ID NO 17
<211> LENGTH: 321
<212> TYPE: DNA
<213> ORGANISM: Mus musculus

<400> SEQUENCE: 17
gacatccaga tgactcagtc tccagcctcc ctatctgtat ctgtgggaga aactgtcacc    60
atcacatgtc gagcaagtga aaatatttac agaaatttag catggtatca gcagaaacag   120
ggaaaatctc ctcagctcct ggtctatgct gcaacaaact tagcagatgg tgtgccatca   180
aggttcagtg gcagtggatc aggcacacag tattccctca agatcaacag cctgcagtct   240
gaagattttg ggagttatta ctgtcaacat ttttggggta ctccgtggac gttcggtgga   300
ggcaccaagc tggaaatcaa a                                             321

<210> SEQ ID NO 18
<211> LENGTH: 40
<212> TYPE: DNA
<213> ORGANISM: Artificial Sequence
<220> FEATURE:
<223> OTHER INFORMATION: Synthetic primer

<400> SEQUENCE: 18
gcgaagcttg ccgccaccat ggcttgggtg tggaccttgc                          40

<210> SEQ ID NO 19
<211> LENGTH: 40
<212> TYPE: DNA
<213> ORGANISM: Artificial Sequence
<220> FEATURE:
<223> OTHER INFORMATION: Synthetic primer

<400> SEQUENCE: 19
gcgaagcttg ccgccaccat gagtgtgccc actcaggtcc                          40

<210> SEQ ID NO 20
<211> LENGTH: 36
<212> TYPE: DNA
<213> ORGANISM: Artificial Sequence
<220> FEATURE:
<223> OTHER INFORMATION: Synthetic primer

<400> SEQUENCE: 20
gcggaattca tcatttacca ggagagtggg agaggc                              36

<210> SEQ ID NO 21
<211> LENGTH: 40
<212> TYPE: DNA
<213> ORGANISM: Artificial Sequence
<220> FEATURE:
<223> OTHER INFORMATION: Synthetic primer

<400> SEQUENCE: 21
cgcgaattca ctaacactca ttcctgttga agctcttgac                          40

<210> SEQ ID NO 22
<211> LENGTH: 324
<212> TYPE: PRT
<213> ORGANISM: Mus musculus

<400> SEQUENCE: 22

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 23
<211> LENGTH: 107
<212> TYPE: PRT
<213> ORGANISM: Mus musculus

<400> SEQUENCE: 23

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg

```
            35                  40                  45
Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 24
<211> LENGTH: 975
<212> TYPE: DNA
<213> ORGANISM: Mus musculus

<400> SEQUENCE: 24
gccaaaacga caccccatc tgtctatcca ctggcccctg gatctgctgc ccaaactaac      60
tccatggtga ccctgggatg cctggtcaag ggctatttcc ctgagccagt gacagtgacc    120
tggaactctg gatccctgtc cagcggtgtg cacaccttcc cagctgtcct gcagtctgac    180
ctctacactc tgagcagctc agtgactgtc ccctccagca cctggcccag cgagaccgtc    240
acctgcaacg ttgcccaccc ggccagcagc accaaggtgg acaagaaaat tgtgcccagg    300
gattgtggtt gtaagccttg catatgtaca gtccagaag tatcatctgt cttcatcttc     360
cccccaaagc ccaaggatgt gctcaccatt actctgactc ctaaggtcac gtgtgttgtg    420
gtagacatca gcaaggatga tcccgaggtc cagttcagct ggtttgtaga tgatgtggag    480
gtgcacacag ctcagacgca accccgggag gagcagttca acagcacttt ccgctcagtc    540
agtgaacttc ccatcatgca ccaggactgg ctcaatggca aggagttcaa atgcagggtc    600
aacagtgcag ctttccctgc ccccatcgag aaaaccatct ccaaaaccaa aggcagaccg    660
aaggctccac aggtgtacac cattccacct cccaaggagc agatggccaa ggataaagtc    720
agtctgacct gcatgataac agacttcttc cctgaagaca ttactgtgga gtggcagtgg    780
aatgggcagc cagcggagaa ctacaagaac actcagccca tcatggacac agatggctct    840
tacttcgtct acagcaagct caatgtgcag aagagcaact gggaggcagg aaatactttc    900
acctgctctg tgttacatga gggcctgcac aaccaccata ctgagaagag cctctcccac    960
tctcctggta aatga                                                    975

<210> SEQ ID NO 25
<211> LENGTH: 324
<212> TYPE: DNA
<213> ORGANISM: Mus musculus

<400> SEQUENCE: 25
cgggctgatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga acagttggac tgatcaggac    180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg ttag                                          324

<210> SEQ ID NO 26
<211> LENGTH: 5
```

```
<212> TYPE: PRT
<213> ORGANISM: Mus musculus

<400> SEQUENCE: 26

Asp Tyr Ser Met His
1               5

<210> SEQ ID NO 27
<211> LENGTH: 10
<212> TYPE: PRT
<213> ORGANISM: Mus musculus

<400> SEQUENCE: 27

Gly Tyr Thr Phe Thr Asp Tyr Ser Met His
1               5                   10

<210> SEQ ID NO 28
<211> LENGTH: 17
<212> TYPE: PRT
<213> ORGANISM: Mus musculus

<400> SEQUENCE: 28

Trp Ile Asn Thr Glu Thr Gly Glu Pro Thr Tyr Ala Asp Asp Phe Lys
1               5                   10                  15

Gly

<210> SEQ ID NO 29
<211> LENGTH: 10
<212> TYPE: PRT
<213> ORGANISM: Mus musculus

<400> SEQUENCE: 29

Trp Ile Asn Thr Glu Thr Gly Glu Pro Thr
1               5                   10

<210> SEQ ID NO 30
<211> LENGTH: 15
<212> TYPE: PRT
<213> ORGANISM: Mus musculus

<400> SEQUENCE: 30

Ile Pro Leu Tyr Tyr Tyr Gly Ser Arg Tyr Trp Tyr Phe Asp Val
1               5                   10                  15

<210> SEQ ID NO 31
<211> LENGTH: 11
<212> TYPE: PRT
<213> ORGANISM: Mus musculus

<400> SEQUENCE: 31

Arg Ala Ser Glu Asn Ile Tyr Arg Asn Leu Ala
1               5                   10

<210> SEQ ID NO 32
<211> LENGTH: 7
<212> TYPE: PRT
<213> ORGANISM: Mus musculus

<400> SEQUENCE: 32

Ala Ala Thr Asn Leu Ala Asp
1               5

<210> SEQ ID NO 33
<211> LENGTH: 9
```

```
<212> TYPE: PRT
<213> ORGANISM: Mus musculus

<400> SEQUENCE: 33

Gln His Phe Trp Gly Thr Pro Trp Thr
1               5

<210> SEQ ID NO 34
<211> LENGTH: 15
<212> TYPE: DNA
<213> ORGANISM: Mus musculus

<400> SEQUENCE: 34
gactattcaa tgcac                                                       15

<210> SEQ ID NO 35
<211> LENGTH: 30
<212> TYPE: DNA
<213> ORGANISM: Mus musculus

<400> SEQUENCE: 35
ggttatacct tcacagacta ttcaatgcac                                       30

<210> SEQ ID NO 36
<211> LENGTH: 51
<212> TYPE: DNA
<213> ORGANISM: Mus musculus

<400> SEQUENCE: 36
tggataaaca ctgagactgg tgagccaaca tatgcagatg acttcaaggg a               51

<210> SEQ ID NO 37
<211> LENGTH: 30
<212> TYPE: DNA
<213> ORGANISM: Mus musculus

<400> SEQUENCE: 37
tggataaaca ctgagactgg tgagccaaca                                       30

<210> SEQ ID NO 38
<211> LENGTH: 45
<212> TYPE: DNA
<213> ORGANISM: Mus musculus

<400> SEQUENCE: 38
attcccctct attactacgg tagtaggtac tggtacttcg atgtc                      45

<210> SEQ ID NO 39
<211> LENGTH: 33
<212> TYPE: DNA
<213> ORGANISM: Mus musculus

<400> SEQUENCE: 39
cgagcaagtg agaatattta cagaaattta gca                                   33

<210> SEQ ID NO 40
<211> LENGTH: 21
<212> TYPE: DNA
<213> ORGANISM: Mus musculus

<400> SEQUENCE: 40
gctgcaacaa acttagcaga t                                                21
```

-continued

<210> SEQ ID NO 41
<211> LENGTH: 27
<212> TYPE: DNA
<213> ORGANISM: Mus musculus

<400> SEQUENCE: 41
caacattttt ggggtactcc gtggacg                                          27

<210> SEQ ID NO 42
<211> LENGTH: 19
<212> TYPE: PRT
<213> ORGANISM: Mus musculus

<400> SEQUENCE: 42

Met Ala Gly Ile Phe Tyr Phe Ile Leu Phe Ser Phe Leu Phe Gly Ile
1               5                   10                  15

Cys Asp Ala

<210> SEQ ID NO 43
<211> LENGTH: 1030
<212> TYPE: PRT
<213> ORGANISM: Mus musculus

<400> SEQUENCE: 43

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
                20                  25                  30

Gly Gly Trp Glu Glu Val Ser Ile Met Asp Glu Lys Asn Thr Pro Ile
            35                  40                  45

Arg Thr Tyr Gln Val Cys Asn Val Met Glu Ala Ser Gln Asn Asn Trp
        50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Tyr Glu Ser Asp Asn
            100                 105                 110

Asp Lys Glu Arg Phe Ile Arg Glu Ser Gln Phe Gly Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Gln Asn Gly Glu Cys Gln Ala
                245                 250                 255

Cys Lys Ile Gly Tyr Tyr Lys Ala Leu Ser Thr Asp Ala Ser Cys Ala

```
              260                 265                 270
Lys Cys Pro Pro His Ser Tyr Ser Val Trp Glu Gly Ala Thr Ser Cys
            275                 280                 285

Thr Cys Asp Arg Gly Phe Phe Arg Ala Asp Asn Asp Ala Ala Ser Met
290                 295                 300

Pro Cys Thr Arg Pro Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
            355                 360                 365

Pro Gln Gln Asn Gly Leu Lys Thr Thr Arg Val Ser Ile Thr Asp Leu
            370                 375                 380

Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
            435                 440                 445

Asn Gly Val Ile Leu Glu Tyr Glu Val Lys Tyr Tyr Glu Lys Asp Gln
            450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
            515                 520                 525

Ala Ala Ala Ile Ile Pro Val Glu Glu Asn Pro Asp Phe Trp Asn
            530                 535                 540

Arg Glu Ala Ala Glu Ala Leu Gly Ala Ala Lys Lys Leu Gln Pro Ala
545                 550                 555                 560

Gln Thr Ala Ala Lys Asn Leu Ile Ile Phe Leu Gly Asp Gly Met Gly
                565                 570                 575

Val Ser Thr Val Thr Ala Ala Arg Ile Leu Lys Gly Gln Lys Lys Asp
            580                 585                 590

Lys Leu Gly Pro Glu Ile Pro Leu Ala Met Asp Arg Phe Pro Tyr Val
            595                 600                 605

Ala Leu Ser Lys Thr Tyr Asn Val Asp Lys His Val Pro Asp Ser Gly
            610                 615                 620

Ala Thr Ala Thr Ala Tyr Leu Cys Gly Val Lys Gly Asn Phe Gln Thr
625                 630                 635                 640

Ile Gly Leu Ser Ala Ala Arg Phe Asn Gln Cys Asn Thr Thr Arg
                645                 650                 655

Gly Asn Glu Val Ile Ser Val Met Asn Arg Ala Lys Lys Ala Gly Lys
            660                 665                 670

Ser Val Gly Val Val Thr Thr Thr Arg Val Gln His Ala Ser Pro Ala
            675                 680                 685
```

Gly Thr Tyr Ala His Thr Val Asn Arg Asn Trp Tyr Ser Asp Ala Asp
            690                 695                 700

Val Pro Ala Ser Ala Arg Gln Glu Gly Cys Gln Asp Ile Ala Thr Gln
705                 710                 715                 720

Leu Ile Ser Asn Met Asp Ile Asp Val Ile Leu Gly Gly Arg Lys
                725                 730                 735

Tyr Met Phe Arg Met Gly Thr Pro Asp Pro Glu Tyr Pro Asp Asp Tyr
                740                 745                 750

Ser Gln Gly Gly Thr Arg Leu Asp Gly Lys Asn Leu Val Gln Glu Trp
            755                 760                 765

Leu Ala Lys Arg Gln Gly Ala Arg Tyr Val Trp Asn Arg Thr Glu Leu
770                 775                 780

Met Gln Ala Ser Leu Asp Pro Ser Val Thr His Leu Met Gly Leu Phe
785                 790                 795                 800

Glu Pro Gly Asp Met Lys Tyr Glu Ile His Arg Asp Ser Thr Leu Asp
                805                 810                 815

Pro Ser Leu Met Glu Met Thr Glu Ala Ala Leu Arg Leu Leu Ser Arg
                820                 825                 830

Asn Pro Arg Gly Phe Phe Leu Phe Val Glu Gly Gly Arg Ile Asp His
            835                 840                 845

Gly His His Glu Ser Arg Ala Tyr Arg Ala Leu Thr Glu Thr Ile Met
850                 855                 860

Phe Asp Asp Ala Ile Glu Arg Ala Gly Gln Leu Thr Ser Glu Glu Asp
865                 870                 875                 880

Thr Leu Ser Leu Val Thr Ala Asp His Ser His Val Phe Ser Phe Gly
                885                 890                 895

Gly Tyr Pro Leu Arg Gly Ser Ser Ile Phe Gly Leu Ala Pro Gly Lys
            900                 905                 910

Ala Arg Asp Arg Lys Ala Tyr Thr Val Leu Leu Tyr Gly Asn Gly Pro
915                 920                 925

Gly Tyr Val Leu Lys Asp Gly Ala Arg Pro Asp Val Thr Glu Ser Glu
                930                 935                 940

Ser Gly Ser Pro Glu Tyr Arg Gln Gln Ser Ala Val Pro Leu Asp Glu
945                 950                 955                 960

Glu Thr His Ala Gly Glu Asp Val Ala Val Phe Ala Arg Gly Pro Gln
                965                 970                 975

Ala His Leu Val His Gly Val Gln Glu Gln Thr Phe Ile Ala His Val
            980                 985                 990

Met Ala Phe Ala Ala Cys Leu Glu Pro Tyr Thr Ala Cys Asp Leu Ala
995                 1000                1005

Pro Pro Ala Gly Thr Thr Asp Ala Ala His Pro Gly His His His
    1010                1015                1020

His His  His His His His His
1025                1030

<210> SEQ ID NO 44
<211> LENGTH: 986
<212> TYPE: PRT
<213> ORGANISM: Macaca mulatta

<400> SEQUENCE: 44

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr

```
                   20                  25                  30
Leu Leu Asp Ser Arg Ser Val Gln Gly Glu Leu Gly Trp Ile Ala Ser
                35                  40                  45
Pro Leu Glu Gly Gly Trp Glu Glu Val Ser Ile Met Asp Glu Lys Asn
         50                  55                  60
Thr Pro Ile Arg Thr Tyr Gln Val Cys Asn Val Met Glu Pro Ser Gln
 65                  70                  75                  80
Asn Asn Trp Leu Arg Thr Asp Trp Ile Thr Arg Glu Gly Ala Gln Arg
                85                  90                  95
Val Tyr Ile Glu Ile Lys Phe Thr Leu Arg Asp Cys Asn Ser Leu Pro
               100                 105                 110
Gly Val Met Gly Thr Cys Lys Glu Thr Phe Asn Leu Tyr Tyr Tyr Glu
               115                 120                 125
Ser Asp Asn Asp Lys Glu Arg Phe Ile Arg Glu Asn Gln Phe Val Lys
           130                 135                 140
Ile Asp Thr Ile Ala Ala Asp Glu Ser Phe Thr Gln Val Asp Ile Gly
145                 150                 155                 160
Asp Arg Ile Met Lys Leu Asn Thr Glu Ile Arg Asp Val Gly Pro Leu
               165                 170                 175
Ser Lys Lys Gly Phe Tyr Leu Ala Phe Gln Asp Val Gly Ala Cys Ile
               180                 185                 190
Ala Leu Val Ser Val Arg Val Phe Tyr Lys Lys Cys Pro Leu Thr Val
               195                 200                 205
Arg Asn Leu Ala Gln Phe Pro Asp Thr Ile Thr Gly Ala Asp Thr Ser
           210                 215                 220
Ser Leu Val Glu Val Arg Gly Ser Cys Val Asn Asn Ser Glu Glu Lys
225                 230                 235                 240
Asp Val Pro Lys Met Tyr Cys Gly Ala Asp Gly Glu Trp Leu Val Pro
               245                 250                 255
Ile Gly Asn Cys Leu Cys Asn Ala Gly His Glu Glu Arg Ser Gly Glu
               260                 265                 270
Cys Gln Ala Cys Lys Ile Gly Tyr Tyr Lys Ala Leu Ser Thr Asp Ala
           275                 280                 285
Thr Cys Ala Lys Cys Pro Pro His Ser Tyr Ser Val Trp Glu Gly Ala
       290                 295                 300
Thr Ser Cys Thr Cys Asp Arg Gly Phe Phe Arg Ala Asp Asn Asp Ala
305                 310                 315                 320
Ala Ser Met Pro Cys Thr Arg Pro Pro Ser Ala Pro Leu Asn Leu Ile
               325                 330                 335
Ser Asn Val Asn Glu Thr Ser Val Asn Leu Glu Trp Ser Ser Pro Gln
           340                 345                 350
Asn Thr Gly Gly Arg Gln Asp Ile Ser Tyr Asn Val Val Cys Lys Lys
           355                 360                 365
Cys Gly Ala Gly Asp Pro Ser Lys Cys Arg Pro Cys Gly Ser Gly Val
       370                 375                 380
His Tyr Thr Pro Gln Gln Asn Gly Leu Lys Thr Thr Lys Val Ser Ile
385                 390                 395                 400
Thr Asp Leu Leu Ala His Thr Asn Tyr Thr Phe Glu Ile Trp Ala Val
               405                 410                 415
Asn Gly Val Ser Lys Tyr Asn Pro Ser Pro Asp Gln Ser Val Ser Val
           420                 425                 430
Thr Val Thr Thr Asn Gln Ala Ala Pro Ser Ser Ile Ala Leu Val Gln
           435                 440                 445
```

```
Ala Lys Glu Val Thr Arg Tyr Ser Val Ala Leu Ala Trp Leu Glu Pro
    450                 455                 460

Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
            500                 505                 510

Val Arg Ala Arg Thr Ala Ala Gly Tyr Gly Asp Phe Ser Glu Pro Leu
        515                 520                 525

Glu Val Thr Thr Asn Thr Val Pro Ser Arg Ile Ile Gly Asp Gly Ala
    530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Arg Ser Lys Tyr
                565                 570                 575

Ser Lys Ala Lys Gln Glu Ala Asp Glu Glu Lys His Leu Asn Gln Gly
            580                 585                 590

Val Arg Thr Tyr Val Asp Pro Phe Thr Tyr Glu Asp Pro Asn Gln Ala
        595                 600                 605

Val Arg Glu Phe Ala Lys Glu Ile Asp Ala Ser Cys Ile Lys Ile Glu
    610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
            660                 665                 670

Ile Met Gly Gln Phe Asp His Pro Asn Ile Ile His Leu Glu Gly Val
        675                 680                 685

Val Thr Lys Cys Lys Pro Val Met Ile Ile Thr Glu Tyr Met Glu Asn
    690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
            740                 745                 750

Leu Val Asn Ser Asn Leu Val Cys Lys Val Ser Asp Phe Gly Met Ser
        755                 760                 765

Arg Val Leu Glu Asp Asp Pro Glu Ala Ala Tyr Thr Thr Arg Gly Gly
    770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
            820                 825                 830

Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860
```

```
Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
            885                 890                 895

Arg Pro Asn Thr Ala Leu Leu Asp Pro Ser Pro Glu Phe Ser Ala
        900                 905                 910

Val Val Ser Val Gly Asp Trp Leu Gln Ala Ile Lys Met Asp Arg Tyr
            915                 920                 925

Lys Asp Asn Phe Thr Ala Ala Gly Tyr Thr Thr Leu Glu Ala Val Val
        930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
            965                 970                 975

Gln Gln Met His Gly Arg Met Val Pro Val
            980                 985

<210> SEQ ID NO 45
<211> LENGTH: 528
<212> TYPE: PRT
<213> ORGANISM: Macaca mulatta

<400> SEQUENCE: 45

Val Thr Gly Ser Arg Val Tyr Pro Ala Asn Glu Val Thr Leu Leu Asp
1               5                   10                  15

Ser Arg Ser Val Gln Gly Glu Leu Gly Trp Ile Ala Ser Pro Leu Glu
            20                  25                  30

Gly Gly Trp Glu Glu Val Ser Ile Met Asp Glu Lys Asn Thr Pro Ile
        35                  40                  45

Arg Thr Tyr Gln Val Cys Asn Val Met Glu Pro Ser Gln Asn Asn Trp
    50                  55                  60

Leu Arg Thr Asp Trp Ile Thr Arg Glu Gly Ala Gln Arg Val Tyr Ile
65                  70                  75                  80

Glu Ile Lys Phe Thr Leu Arg Asp Cys Asn Ser Leu Pro Gly Val Met
                85                  90                  95

Gly Thr Cys Lys Glu Thr Phe Asn Leu Tyr Tyr Glu Ser Asp Asn
            100                 105                 110

Asp Lys Glu Arg Phe Ile Arg Glu Asn Gln Phe Val Lys Ile Asp Thr
        115                 120                 125

Ile Ala Ala Asp Glu Ser Phe Thr Gln Val Asp Ile Gly Asp Arg Ile
    130                 135                 140

Met Lys Leu Asn Thr Glu Ile Arg Asp Val Gly Pro Leu Ser Lys Lys
145                 150                 155                 160

Gly Phe Tyr Leu Ala Phe Gln Asp Val Gly Ala Cys Ile Ala Leu Val
                165                 170                 175

Ser Val Arg Val Phe Tyr Lys Lys Cys Pro Leu Thr Val Arg Asn Leu
            180                 185                 190

Ala Gln Phe Pro Asp Thr Ile Thr Gly Ala Asp Thr Ser Ser Leu Val
        195                 200                 205

Glu Val Arg Gly Ser Cys Val Asn Asn Ser Glu Lys Asp Val Pro
    210                 215                 220

Lys Met Tyr Cys Gly Ala Asp Gly Glu Trp Leu Val Pro Ile Gly Asn
225                 230                 235                 240

Cys Leu Cys Asn Ala Gly His Glu Glu Arg Ser Gly Glu Cys Gln Ala
                245                 250                 255
```

Cys Lys Ile Gly Tyr Tyr Lys Ala Leu Ser Thr Asp Ala Thr Cys Ala
                260                 265                 270

Lys Cys Pro Pro His Ser Tyr Ser Val Trp Glu Ala Thr Ser Cys
            275                 280                 285

Thr Cys Asp Arg Gly Phe Phe Arg Ala Asp Asn Asp Ala Ala Ser Met
        290                 295                 300

Pro Cys Thr Arg Pro Ser Ala Pro Leu Asn Leu Ile Ser Asn Val
305                 310                 315                 320

Asn Glu Thr Ser Val Asn Leu Glu Trp Ser Ser Pro Gln Asn Thr Gly
                325                 330                 335

Gly Arg Gln Asp Ile Ser Tyr Asn Val Val Cys Lys Lys Cys Gly Ala
            340                 345                 350

Gly Asp Pro Ser Lys Cys Arg Pro Cys Gly Ser Gly Val His Tyr Thr
        355                 360                 365

Pro Gln Gln Asn Gly Leu Lys Thr Thr Lys Val Ser Ile Thr Asp Leu
370                 375                 380

Leu Ala His Thr Asn Tyr Thr Phe Glu Ile Trp Ala Val Asn Gly Val
385                 390                 395                 400

Ser Lys Tyr Asn Pro Ser Pro Asp Gln Ser Val Ser Val Thr Val Thr
                405                 410                 415

Thr Asn Gln Ala Ala Pro Ser Ser Ile Ala Leu Val Gln Ala Lys Glu
            420                 425                 430

Val Thr Arg Tyr Ser Val Ala Leu Ala Trp Leu Glu Pro Asp Arg Pro
        435                 440                 445

Asn Gly Val Ile Leu Glu Tyr Glu Val Lys Tyr Glu Lys Asp Gln
450                 455                 460

Asn Glu Arg Ser Tyr Arg Ile Val Arg Thr Ala Ala Arg Asn Thr Asp
465                 470                 475                 480

Ile Lys Gly Leu Asn Pro Leu Thr Ser Tyr Val Phe His Val Arg Ala
                485                 490                 495

Arg Thr Ala Ala Gly Tyr Gly Asp Phe Ser Glu Pro Leu Glu Val Thr
            500                 505                 510

Thr Asn Thr Val Pro Ser Arg Ile Ile Gly Asp Gly Ala Asn Ser Thr
        515                 520                 525

<210> SEQ ID NO 46
<211> LENGTH: 21
<212> TYPE: DNA
<213> ORGANISM: Artificial Sequence
<220> FEATURE:
<223> OTHER INFORMATION: Synthetic Primer

<400> SEQUENCE: 46
catcagccct aatccatctg a                                         21

<210> SEQ ID NO 47
<211> LENGTH: 21
<212> TYPE: DNA
<213> ORGANISM: Artificial Sequence
<220> FEATURE:
<223> OTHER INFORMATION: Synthetic Primer

<400> SEQUENCE: 47
cgcgactaac aatcaaagtg a                                         21

<210> SEQ ID NO 48
<211> LENGTH: 24

```
<212> TYPE: DNA
<213> ORGANISM: Artificial Sequence
<220> FEATURE:
<223> OTHER INFORMATION: Synthetic Primer

<400> SEQUENCE: 48
ctaggccaca gaattgaaag atct                                          24

<210> SEQ ID NO 49
<211> LENGTH: 25
<212> TYPE: DNA
<213> ORGANISM: Artificial Sequence
<220> FEATURE:
<223> OTHER INFORMATION: Synthetic Primer

<400> SEQUENCE: 49
gtaggtggaa attctagcat catcc                                         25

<210> SEQ ID NO 50
<211> LENGTH: 96
<212> TYPE: PRT
<213> ORGANISM: Artificial Sequence
<220> FEATURE:
<223> OTHER INFORMATION: synthetic antibody framework region sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Pro
                85                  90                  95

<210> SEQ ID NO 51
<211> LENGTH: 96
<212> TYPE: PRT
<213> ORGANISM: Artificial Sequence
<220> FEATURE:
<223> OTHER INFORMATION: synthetic antibody framework region sequence

<400> SEQUENCE: 51

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

<210> SEQ ID NO 52
```

```
<211> LENGTH: 12
<212> TYPE: PRT
<213> ORGANISM: Artificial Sequence
<220> FEATURE:
<223> OTHER INFORMATION: synthetic antibody framework region sequence

<400> SEQUENCE: 52

Trp Thr Phe Gly Gln Gly Thr Lys Val Glu Ile Lys
1               5                   10

<210> SEQ ID NO 53
<211> LENGTH: 98
<212> TYPE: PRT
<213> ORGANISM: Artificial Sequence
<220> FEATURE:
<223> OTHER INFORMATION: synthetic antibody framework region sequence

<400> SEQUENCE: 53

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg

<210> SEQ ID NO 54
<211> LENGTH: 20
<212> TYPE: PRT
<213> ORGANISM: Artificial Sequence
<220> FEATURE:
<223> OTHER INFORMATION: synthetic antibody framework region sequence

<400> SEQUENCE: 54

Tyr Tyr Tyr Tyr Tyr Gly Met Asp Val Trp Gly Gln Gly Thr Thr Val
1               5                   10                  15

Thr Val Ser Ser
            20

<210> SEQ ID NO 55
<211> LENGTH: 19
<212> TYPE: PRT
<213> ORGANISM: Artificial Sequence
<220> FEATURE:
<223> OTHER INFORMATION: synthetic signal sequence

<400> SEQUENCE: 55

Met Glu Trp Ser Trp Val Phe Leu Phe Phe Leu Ser Val Thr Thr Gly
1               5                   10                  15

Val His Ser

<210> SEQ ID NO 56
<211> LENGTH: 57
<212> TYPE: DNA
<213> ORGANISM: Artificial Sequence
<220> FEATURE:
<223> OTHER INFORMATION: synthetic signal sequence
```

<400> SEQUENCE: 56
atggaatggt catgggtctt tctgttcttt ctgtcagtca caaccggggt ccacagt    57

<210> SEQ ID NO 57
<211> LENGTH: 57
<212> TYPE: DNA
<213> ORGANISM: Artificial Sequence
<220> FEATURE:
<223> OTHER INFORMATION: synthetic signal sequence

<400> SEQUENCE: 57
atggaatggt cttgggtctt tctgttcttt ctgtccgtca ctaccggggt ccactca    57

<210> SEQ ID NO 58
<211> LENGTH: 20
<212> TYPE: PRT
<213> ORGANISM: Artificial Sequence
<220> FEATURE:
<223> OTHER INFORMATION: synthetic signal sequence

<400> SEQUENCE: 58

Met Ser Val Pro Thr Gln Val Leu Gly Leu Leu Leu Leu Trp Leu Thr
1               5                   10                  15

Asp Ala Arg Cys
            20

<210> SEQ ID NO 59
<211> LENGTH: 60
<212> TYPE: DNA
<213> ORGANISM: Artificial Sequence
<220> FEATURE:
<223> OTHER INFORMATION: synthetic signal sequence

<400> SEQUENCE: 59
atgtccgtgc ctactcaggt gctggggctg ctgctgctgt ggctgaccga cgctagatgt    60

<210> SEQ ID NO 60
<211> LENGTH: 328
<212> TYPE: PRT
<213> ORGANISM: Artificial Sequence
<220> FEATURE:
<223> OTHER INFORMATION: synthetic antibody constant region sequence

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Pro Ala Ala Ala Pro Ser Val Phe Leu Phe Pro Pro Lys
        115                 120                 125

```
Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
                180                 185                 190

Gln Asp Trp Leu Asn Gly Lys Glu Tyr Lys Cys Lys Val Ser Asn Lys
            195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 61
<211> LENGTH: 984
<212> TYPE: DNA
<213> ORGANISM: Artificial Sequence
<220> FEATURE:
<223> OTHER INFORMATION: synthetic antibody constant region sequence

<400> SEQUENCE: 61
gctagcacta aaggaccaag cgtgttccct ctggctccaa gcagcaaatc aacctcaggc      60
ggcacagcag cactgggggtg tctggtgaag gactacttcc cagagcccgt caccgtgtca    120
tggaacagcg gagcactgac tagcggagtc cacacctttc cagccgtgct gcagagctcc    180
ggactgtact ccctgtctag tgtggtcaca gtgccttcaa gctccctggg gactcagacc    240
tatatctgca acgtgaatca caagccctcc aatactaagg tcgacaaacg agtggagcct    300
aagtcttgtg ataaaacaca tacttgcccc ccttgtcctg ctccaccagc cgctgcacca    360
agcgtgttcc tgtttcctcc aaagcccaaa gacacactga tgatcagcag aactcctgag    420
gtcacctgcg tggtcgtgga cgtgtcccac gaggatcccg aagtccagtt taactggtac    480 gtggatggggtcgaagtgca taatgcaaag actaaacctc gggaggaaca gttcaactct    540
acctttagag tcgtgagtgt gctgacagtc gtgcaccagg actggctgaa cggaaaggag    600
tataagtgca aagtgtctaa taagggcctg cccgccccta tcgagaaaac aattagtaag    660
actaaaggcc agccaaggga accccaggtg tacacactgc cccctagtcg cgaggaaatg    720
acaaagaacc aggtctcact gacttgtctg gtgaaagggt tctatccatc cgacattgcc    780
gtggagtgga atctaatgg acagcccgaa acaattaca agaccacacc acccatgctg    840
gacagcgatg gatccttctt tctgtattca aagctgaccg tggataaaag ccggtggcag    900
```

```
caggqcaatg tcttttcctg ctctgtgatg cacgaagccc tgcacaacca ctacactcag      960
aagtccctgt ccctgtctcc tggc                                             984
```

<210> SEQ ID NO 62
<211> LENGTH: 325
<212> TYPE: PRT
<213> ORGANISM: Artificial Sequence
<220> FEATURE:
<223> OTHER INFORMATION: synthetic antibody constant region sequence

<400> SEQUENCE: 62

```
Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 63

<211> LENGTH: 975
<212> TYPE: DNA
<213> ORGANISM: Artificial Sequence
<220> FEATURE:
<223> OTHER INFORMATION: synthetic antibody constant region sequence

<400> SEQUENCE: 63

```
gctagcacaa aaggcccctc tgtcttccct ctggctccct cctcccgctc cacctccgag      60
tccactgccg ctctgggctg tctggtcaag gattacttcc ctgagccagt cactgtgagt     120
tggaactcag gcgccctgac cagcggagtc cacacatttc ccgctgtgct gcagagctcc     180
ggcctgtact ccctgtctag tgtggtcacc gtgccttcaa gcaatttcgg gactcagacc     240
tatacatgca acgtggacca taagccatct aatactaagg tcgataaaac cgtggagcga     300
aaatcctgcg tggaatgccc accttgtcct gctccaccag ccgctgcacc aagcgtgttc     360
ctgtttcctc caaagcccaa agacacactg atgatcagca gaactcctga ggtcacctgc     420
gtggtcgtgg acgtgtccca cgaggatccc gaagtccagt ttaactggta cgtggatggg     480
gtcgaagtgc ataatgcaaa gactaaacct cgggaggaac agttcaactc taccttta ga    540
gtcgtgagtg tgctgacagt cgtgcaccag gactggctga acggaaagga gtataagtgc     600
aaagtgtcta ataagggcct gcccgccct atcgagaaaa caattagtaa gactaaaggc      660
cagccaaggg aaccccaggt gtacacactg cccctagtc gcgaggaaat gacaaagaac      720
caggtctcac tgacttgtct ggtgaaaggg ttctatccat ccgacattgc cgtggagtgg     780
gaatctaatg gacagcccga aaacaattac aagaccacac cacccatgct ggacagcgat     840
ggatccttct ttctgtattc aaagctgacc gtggataaaa gccggtggca gcagggcaat     900
gtcttttcct gctctgtgat gcacgaagcc ctgcacaacc actacactca gaagtccctg     960
tccctgtctc ctggc                                                      975
```

<210> SEQ ID NO 64
<211> LENGTH: 107
<212> TYPE: PRT
<213> ORGANISM: Artificial Sequence
<220> FEATURE:
<223> OTHER INFORMATION: synthetic antibody constant region sequence

<400> SEQUENCE: 64

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 65
<211> LENGTH: 321
<212> TYPE: DNA
<213> ORGANISM: Artificial Sequence
<220> FEATURE:

<223> OTHER INFORMATION: synthetic antibody constant region sequence

<400> SEQUENCE: 65

```
cgtacggtcg ccgcccctc cgtgtttatt tttcctccat ctgacgaaca gctgaagagt    60
gggaccgcct ccgtggtgtg cctgctgaac aatttctacc cccgggaggc caaggtgcag   120
tggaaagtcg acaacgctct gcagtctggc aatagtcagg agtcagtgac tgaacaggac   180
agcaaggatt ccacctattc tctgagctcc accctgacac tgagcaaagc agattacgaa   240
aagcacaaag tctatgcctg cgaagtgacc caccagggc tgagcagtcc agtgaccaag    300
tcctttaaca ggggagagtg t                                              321
```

<210> SEQ ID NO 66
<211> LENGTH: 124
<212> TYPE: PRT
<213> ORGANISM: Artificial Sequence
<220> FEATURE:
<223> OTHER INFORMATION: synthetic humanized antibody heavy chain
      variable region sequence

<400> SEQUENCE: 66

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Met
            35                  40                  45

Gly Trp Ile Asn Thr Glu Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Pro Leu Tyr Tyr Tyr Gly Ser Arg Tyr Trp Tyr Phe Asp
            100                 105                 110

Val Trp Gly Gln Gly Thr Thr Val Thr Val Ser Ser
        115                 120
```

<210> SEQ ID NO 67
<211> LENGTH: 372
<212> TYPE: DNA
<213> ORGANISM: Artificial Sequence
<220> FEATURE:
<223> OTHER INFORMATION: synthetic humanized antibody heavy chain
      variable region sequence

<400> SEQUENCE: 67

```
caggtccagc tggtccagtc agggagcgaa ctgaagaaac aggcgcatc agtgaaggtc     60
agctgcaaag cctccgggta ccttcaca gactactcta tgcactgggt gcggcaggct    120
ccaggacagg gactggagtg gatggggtgg atcaacactg agaccggaga acctacctat   180
gctcagggct tcaccggcag attcgtgttt agcctggaca catctgtcag tactgcatac   240
ctgcagatca gctccctgaa ggccgaagat accgctgtct actattgtgc caggattccc   300
ctgtactatt acgggagcag gtattggtat tttgatgtct gggggcaggg aacaaccgtc   360
actgtcagca gc                                                        372
```

<210> SEQ ID NO 68
<211> LENGTH: 124

```
<212> TYPE: PRT
<213> ORGANISM: Artificial Sequence
<220> FEATURE:
<223> OTHER INFORMATION: synthetic humanized antibody heavy chain
      variable region sequence

<400> SEQUENCE: 68

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Pro Leu Tyr Tyr Tyr Gly Ser Arg Tyr Trp Tyr Phe Asp
            100                 105                 110

Val Trp Gly Gln Gly Thr Thr Val Thr Val Ser Ser
        115                 120

<210> SEQ ID NO 69
<211> LENGTH: 372
<212> TYPE: DNA
<213> ORGANISM: Artificial Sequence
<220> FEATURE:
<223> OTHER INFORMATION: synthetic humanized antibody heavy chain
      variable region sequence

<400> SEQUENCE: 69
caggtccagc tggtccagtc agggagcgaa ctgaagaaac caggcgcatc agtgaaggtc     60
agctgcaaag cctccgggta taccttcaca gactactcta tgcactgggt gcggcaggct    120
ccaggacagg gactgaagtg gatggggtgg atcaacactg agaccggaga acctacctat    180
gctcagggct tcaccggcag attcgtgttt agcctggaca catctgtcag tactgcatac    240
ctgcagatca gctccctgaa ggccgaagat accgctgtct actattgtgc caggattccc    300
ctgtactatt acgggagcag gtattggtat tttgatgtct gggggcaggg aacaaccgtc    360
actgtcagca gc                                                         372

<210> SEQ ID NO 70
<211> LENGTH: 124
<212> TYPE: PRT
<213> ORGANISM: Artificial Sequence
<220> FEATURE:
<223> OTHER INFORMATION: synthetic humanized antibody heavy chain
      variable region sequence

<400> SEQUENCE: 70

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Gln Gly Phe
        50                  55                  60
```

```
Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Ile Pro Leu Tyr Tyr Tyr Gly Ser Arg Tyr Trp Tyr Phe Asp
             100                 105                 110

Val Trp Gly Gln Gly Thr Thr Val Thr Val Ser Ser
        115                 120
```

<210> SEQ ID NO 71
<211> LENGTH: 372
<212> TYPE: DNA
<213> ORGANISM: Artificial Sequence
<220> FEATURE:
<223> OTHER INFORMATION: synthetic humanized antibody heavy chain
      variable region sequence

<400> SEQUENCE: 71

```
cagatccagc tggtccagtc agggagcgaa ctgaagaaac caggcgcatc agtgaaggtc     60
agctgcaaag cctccgggta taccttcaca gactactcta tgcactgggt gcggcaggct    120
ccaggacagg gactgaagtg gatggggtgg atcaacactg agaccggaga acctacctat    180
gctcagggct tcaccggcag attcgtgttt agcctggaca catctgtcag tactgcatac    240
ctgcagatca gctccctgaa ggccgaagat accgctgtct actattgtgc caggattccc    300
ctgtactatt acgggagcag gtattggtat tttgatgtct gggggcaggg aacaaccgtc    360
actgtcagca gc                                                        372
```

<210> SEQ ID NO 72
<211> LENGTH: 124
<212> TYPE: PRT
<213> ORGANISM: Artificial Sequence
<220> FEATURE:
<223> OTHER INFORMATION: synthetic humanized antibody heavy chain
      variable region sequence

<400> SEQUENCE: 72

```
Gln Val Gln Leu Val Gln Ser Gly Ser Glu Leu Lys Lys Pro Gly Ala
  1               5                  10                  15

Ser Val Lys Val Ser Cys Lys Ala Ser Gly Tyr Thr Phe Thr Asp Tyr
                 20                  25                  30

Ser Met His Trp Val Arg Gln Ala Pro Gly Gln Gly Leu Glu Trp Met
             35                  40                  45

Gly Trp Ile Asn Thr Glu Thr Gly Glu Pro Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Ile Pro Leu Tyr Tyr Tyr Gly Ser Arg Tyr Trp Tyr Phe Asp
             100                 105                 110

Val Trp Gly Gln Gly Thr Thr Val Thr Val Ser Ser
        115                 120
```

<210> SEQ ID NO 73
<211> LENGTH: 372
<212> TYPE: DNA
<213> ORGANISM: Artificial Sequence
<220> FEATURE:

<223> OTHER INFORMATION: synthetic humanized antibody heavy chain
       variable region sequence

<400> SEQUENCE: 73

```
caggtgcagc tggtgcagtc tgggagcgaa ctgaagaaac cagggggcatc agtgaaggtc      60
agctgcaaag cctccggata taccttcaca gactactcta tgcactgggt gcggcaggct     120
ccaggacagg gactggagtg gatgggatgg atcaacactg agaccggcga acctacctat     180
gctgacgatt ttaagggcag attcgtgttt agcctggaca catctgtcag tactgcatac     240
ctgcagatca gctccctgaa agccgaagat acagctgtct actattgtgc caggattccc     300
ctgtactatt acggaagcag gtattggtat tttgatgtct gggggcaggg aacaactgtg     360
actgtgtcct cc                                                          372
```

<210> SEQ ID NO 74
<211> LENGTH: 124
<212> TYPE: PRT
<213> ORGANISM: Artificial Sequence
<220> FEATURE:
<223> OTHER INFORMATION: synthetic humanized antibody heavy chain
       variable region sequence

<400> SEQUENCE: 74

```
Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Tyr
            20                  25                  30
Ser Met His Trp Val Arg Gln Ala Pro Gly Gln Gly Leu Lys Trp Met
        35                  40                  45
Gly Trp Ile Asn Thr Glu Thr Gly Glu Pro Thr Tyr Ala Asp Asp Phe
    50                  55                  60
Lys Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Tyr Cys
                85                  90                  95
Ala Arg Ile Pro Leu Tyr Tyr Tyr Gly Ser Arg Tyr Trp Tyr Phe Asp
            100                 105                 110
Val Trp Gly Gln Gly Thr Thr Val Thr Val Ser Ser
        115                 120
```

<210> SEQ ID NO 75
<211> LENGTH: 372
<212> TYPE: DNA
<213> ORGANISM: Artificial Sequence
<220> FEATURE:
<223> OTHER INFORMATION: synthetic humanized antibody heavy chain
       variable region sequence

<400> SEQUENCE: 75

```
caggtgcagc tggtgcagtc tgggagcgaa ctgaagaaac cagggggcatc agtgaaggtc      60
agctgcaaag cctccggata taccttcaca gactactcta tgcactgggt gcggcaggct     120
ccaggacagg gactgaagtg gatgggatgg atcaacactg agaccggcga acctacctat     180
gctgacgatt ttaagggcag attcgtgttt agcctggaca catctgtcag tactgcatac     240
ctgcagatca gctccctgaa agccgaagat acagctgtct actattgtgc caggattccc     300
ctgtactatt acggaagcag gtattggtat tttgatgtct gggggcaggg aacaactgtg     360
actgtgtcct cc                                                          372
```

```
<210> SEQ ID NO 76
<211> LENGTH: 124
<212> TYPE: PRT
<213> ORGANISM: Artificial Sequence
<220> FEATURE:
<223> OTHER INFORMATION: synthetic humanized antibody heavy chain
      variable region sequence

<400> SEQUENCE: 76

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Pro Leu Tyr Tyr Tyr Gly Ser Arg Tyr Trp Tyr Phe Asp
            100                 105                 110

Val Trp Gly Gln Gly Thr Thr Val Thr Val Ser Ser
        115                 120

<210> SEQ ID NO 77
<211> LENGTH: 372
<212> TYPE: DNA
<213> ORGANISM: Artificial Sequence
<220> FEATURE:
<223> OTHER INFORMATION: synthetic humanized antibody heavy chain
      variable region sequence

<400> SEQUENCE: 77
cagatccagc tggtgcagtc tgggagcgaa ctgaagaaac caggggcatc agtgaaggtc      60
agctgcaaag cctccggata taccttcaca gactactcta tgcactgggt gcggcaggct     120
ccaggacagg gactgaagtg gatgggatgg atcaacactg agaccggcga acctacctat     180
gctgacgatt ttaagggcag attcgtgttt agcctggaca catctgtcag tactgcatac     240
ctgcagatca gctcccctga agccgaagat acagctgtct actattgtgc caggattccc     300
ctgtactatt acggaagcag gtattggtat tttgatgtct ggggggcaggg aacaactgtg     360 actgtgtcct cc                                                          372

<210> SEQ ID NO 78
<211> LENGTH: 107
<212> TYPE: PRT
<213> ORGANISM: Artificial Sequence
<220> FEATURE:
<223> OTHER INFORMATION: synthetic humanized antibody light chain
      variable region sequence

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Arg Asn
                20                  25                  30

Leu Ala Trp Tyr Gln Gln Lys Pro Gly Lys Ala Pro Lys Leu Leu Val
            35                  40                  45
```

```
Tyr Ala Ala Thr Asn Leu Ala Asp Gly Val Pro Ser Arg Phe Ser Gly
        50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln His Phe Trp Gly Thr Pro Trp
                85                  90                  95

Thr Phe Gly Gln Gly Thr Lys Val Glu Ile Lys
            100                 105
```

<210> SEQ ID NO 79
<211> LENGTH: 321
<212> TYPE: DNA
<213> ORGANISM: Artificial Sequence
<220> FEATURE:
<223> OTHER INFORMATION: synthetic humanized antibody light chain
      variable region sequence

<400> SEQUENCE: 79

```
gatatccaga tgacccagtc tccttcctct ctgagtgctt cagtgggcga ccgggtcacc      60
atcacatgca gagcaagcga gaacatctac aggaatctgg cctggtatca gcagaagccc     120
ggcaaagctc ctaagctgct ggtgtacgcc gctaccaacc tggcagatgg agtgccaagc     180
cggttcagcg gatccggatc tggaacagac tatactctga ccatcagctc cctgcagccc     240
gaagattttg ccacttacta ttgtcagcat ttctggggca ccttggac cttcgggcag       300
ggaactaaag tggagattaa g                                              321
```

<210> SEQ ID NO 80
<211> LENGTH: 107
<212> TYPE: PRT
<213> ORGANISM: Artificial Sequence
<220> FEATURE:
<223> OTHER INFORMATION: synthetic humanized antibody light chain
      variable region sequence

<400> SEQUENCE: 80

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Arg Asn
            20                  25                  30

Leu Ala Trp Tyr Gln Gln Lys Pro Gly Lys Ala Pro Lys Leu Leu Leu
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Ser
 65                  70                  75                  80

Glu Asp Phe Ala Thr Tyr Tyr Cys Gln His Phe Trp Gly Thr Pro Trp
                85                  90                  95

Thr Phe Gly Gln Gly Thr Lys Val Glu Ile Lys
            100                 105
```

<210> SEQ ID NO 81
<211> LENGTH: 321
<212> TYPE: DNA
<213> ORGANISM: Artificial Sequence
<220> FEATURE:
<223> OTHER INFORMATION: synthetic humanized antibody light chain
      variable region sequence

<400> SEQUENCE: 81

```
gatatccaga tgacccagtc tccttcctct ctgagtgctt cagtgggcga ccgggtcacc    60
atcacatgca gagcaagcga aacatctac aggaatctgg cctggtatca gcagaagccc   120
ggcaaagctc ctaagctgct gctgtacgcc gctaccaacc tggcagatgg agtgccaagc   180
cggttcagcg gatccggatc tggaacagac tatactctga ccatcagctc cctgcagtcc   240
gaagattttg ccacttacta ttgtcagcat ttctggggca caccttggac cttcgggcag   300
ggaactaaag tggagattaa g                                             321
```

<210> SEQ ID NO 82
<211> LENGTH: 107
<212> TYPE: PRT
<213> ORGANISM: Artificial Sequence
<220> FEATURE:
<223> OTHER INFORMATION: synthetic humanized antibody light chain
      variable region sequence

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Arg Asn
            20                  25                  30

Leu Ala Trp Tyr Gln Gln Lys Pro Gly Lys Ala Pro Gln Leu Leu Leu
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Trp
                85                  90                  95

Thr Phe Gly Gln Gly Thr Lys Val Glu Ile Lys
            100                 105

<210> SEQ ID NO 83
<211> LENGTH: 321
<212> TYPE: DNA
<213> ORGANISM: Artificial Sequence
<220> FEATURE:
<223> OTHER INFORMATION: synthetic humanized antibody light chain
      variable region sequence

<400> SEQUENCE: 83

```
gatatccaga tgacccagtc tccttcctct ctgagtgctt cagtgggcga ccgggtcacc    60
atcacatgca gagcaagcga aacatctac aggaatctgg cctggtatca gcagaagccc   120
ggcaaagctc ctcaactgct gctgtacgcc gctaccaacc tggcagatgg agtgccaagc   180
cggttcagcg gatccggatc tggaacagac tatactctga ccatcagctc cctgcagccc   240
gaagattttg ccacttacta ttgtcagcat ttctggggca caccttggac cttcgggcag   300
ggaactaaag tggagattaa g                                             321
```

<210> SEQ ID NO 84
<211> LENGTH: 107
<212> TYPE: PRT
<213> ORGANISM: Artificial Sequence
<220> FEATURE:
<223> OTHER INFORMATION: synthetic humanized antibody light chain
      variable region sequence

```
<400> SEQUENCE: 84

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Asn Ile Tyr Arg Asn
            20                  25                  30

Leu Ala Trp Tyr Gln Gln Lys Pro Gly Gln Ser Pro Arg Leu Leu Ile
        35                  40                  45

Tyr Ala Ala Thr Asn Leu Ala Asp Gly Ile Pro Ala Arg Phe Ser Gly
    50                  55                  60

Ser Gly Ser Gly Thr Glu Tyr Thr Leu Thr Ile Ser Ser Leu Gln Ser
65                  70                  75                  80

Glu Asp Phe Ala Val Tyr Tyr Cys Gln His Phe Trp Gly Thr Pro Trp
                85                  90                  95

Thr Phe Gly Gln Gly Thr Lys Val Glu Ile Lys
            100                 105

<210> SEQ ID NO 85
<211> LENGTH: 321
<212> TYPE: DNA
<213> ORGANISM: Artificial Sequence
<220> FEATURE:
<223> OTHER INFORMATION: synthetic humanized antibody light chain
      variable region sequence

<400> SEQUENCE: 85
gaaatcgtga tgacccagtc tcccgccact ctgtctgtga gtccaggcga gcgggctacc       60
ctgtcttgca gagcaagcga aaacatctac aggaatctgg cctggtatca gcagaagcca      120
ggacagtctc ctcgactgct gatctacgcc gctacaaacc tggcagacgg gattcccgca      180
cgattctcag gaagcggatc cggaaccgag tataccctga caattagctc cctgcagagc      240
gaagatttcg ccgtctacta ttgtcagcat ttctggggaa caccttggac attcgggcag      300
ggaactaaag tggagattaa g                                                321
```